US010316092B2

(12) United States Patent
Yao et al.

(10) Patent No.: US 10,316,092 B2
(45) Date of Patent: Jun. 11, 2019

(54) ANTI-B7-H5 ANTIBODIES AND THEIR USES

(71) Applicants: MEDIMMUNE, LLC, Gaithersburg, MD (US); THE JOHNS HOPKINS UNIVERSITY, Baltimore, MD (US)

(72) Inventors: Sheng Yao, Columbia, MD (US); Lieping Chen, Hampden, CT (US); Linda Liu, Columbia, MD (US); Solomon Langermann, Baltimore, MD (US)

(73) Assignees: THE JOHN HOPKINS UNIVERSITY, Baltimore, MD (US); MEDIMMUNE, LLC, Gaitherburgh, MD (US)

( * ) Notice: Subject to any disclaimer, the term of this patent is extended or adjusted under 35 U.S.C. 154(b) by 454 days.

(21) Appl. No.: 14/893,463

(22) PCT Filed: May 27, 2014

(86) PCT No.: PCT/US2014/039621
§ 371 (c)(1),
(2) Date: Nov. 23, 2015

(87) PCT Pub. No.: WO2014/190356
PCT Pub. Date: Nov. 27, 2014

(65) Prior Publication Data
US 2016/0096891 A1 Apr. 7, 2016

Related U.S. Application Data

(60) Provisional application No. 61/827,216, filed on May 24, 2013.

(51) Int. Cl.
*C07K 16/28* (2006.01)
*A61K 39/395* (2006.01)
*A61K 39/00* (2006.01)

(52) U.S. Cl.
CPC .... *C07K 16/2827* (2013.01); *A61K 2039/505* (2013.01); *C07K 2317/24* (2013.01); *C07K 2317/565* (2013.01); *C07K 2317/76* (2013.01)

(58) Field of Classification Search
None
See application file for complete search history.

(56) References Cited

U.S. PATENT DOCUMENTS

2010/0041074 A1\* 2/2010 Kimura ............ A61K 47/48415
435/7.23
2017/0306024 A1\* 10/2017 Noelle ............... C07K 16/2827

FOREIGN PATENT DOCUMENTS

WO 2011020024 A2 2/2011

OTHER PUBLICATIONS

Ni et al. (2017) Mol Cancer Ther; 16(7): 1203-1211.\*
Zhao et al. Proc Natl Acad Sci U S A. Jun. 11, 2013;110(24):9879-9884.\*
Zhu et al. Nature Communications vol. 4, Article No. 2043 (2013); 12 pages.\*
Wang, L. et al., Vista, a novel mouse Ig superfamily ligand that negatively regulates T cell responses, Nature Reviews Immunology, vol. 8, No. 6, Mar. 14, 2011, pp. 467-492.
Flies, D.B. et al., "Cutting Edge: A Monoclonal Antibody Specific for the Programmed Death-1 Homolog Prevents Graft-versus-Host Disease in Mouse Models," The Journal of Immunology, vol. 187, No. 4, Jul. 18, 2011, pp. 1537-1541.
Moustafa, S. et al., "GI24 enhances tumor invasiveness by regulating cell surface membrane-type 1 matrix metalloproteinase," Cancer Science, vol. 101, No. 11, Jul. 13, 2010, pp. 2368-2374.
Linsley, P. et al., "The clinical utility of inhibiting CD28-mediated costimulation," May 2009, Immunological Reviews, vol. 229, pp. 307-321.
Flajnik et al., "Evolution of the B7 family: co-evolution of B7H6 and NKp30, identification of a new B7 family member, B7H7, and of B7's historical relationship with the MHC", Immunogenetics, Springer, Berlin, DE, vol. 64, No. 8, Apr. 11, 2012, pp. 571-590.
Printed website entry for HHLA2 Gene; from GeneCards Human Gene Database; Weizmann Institute of Science, LifeMap Sciences, printed from <http://www.genecards.org/cgi-bin/carddisp.pl?gene=HHLA2&keywords=B7- H5>; 16 pages.
English translation of second examination report in corresponding Japanese Application No. 2016-515141, dated Dec. 4, 2018, (5 pages).

\* cited by examiner

*Primary Examiner* — Ilia I Ouspenski
(74) *Attorney, Agent, or Firm* — Melissa Hunter-Ensor; Leslie Serunian; Greenberg Traurig, LLP

(57) ABSTRACT

The present invention relates to antibodies and their antigen-binding fragments and to other molecules that are capable of immunospecifically binding to the B7-H5 ligand of the B7-H5:CD28H pathway, and to the uses of such molecules in the treatment and diagnosis of autoimmune disease, transplant rejection and other inflammatory diseases.

12 Claims, 20 Drawing Sheets

Specification includes a Sequence Listing.

☐ PBS
■ Anti-B7-H7 Antibody

☐ PBS
■ Anti-B7-H7 Antibody

Purified Anti-Human
B7-H7 Antibody 2D3

Recombinant
Anti-Human B7-H7
Chimeric Antibody
2D3 (hIgG4)

Recombinant
Anti-Human B7-H7
Chimeric Antibody
18C3 (hIgG4)

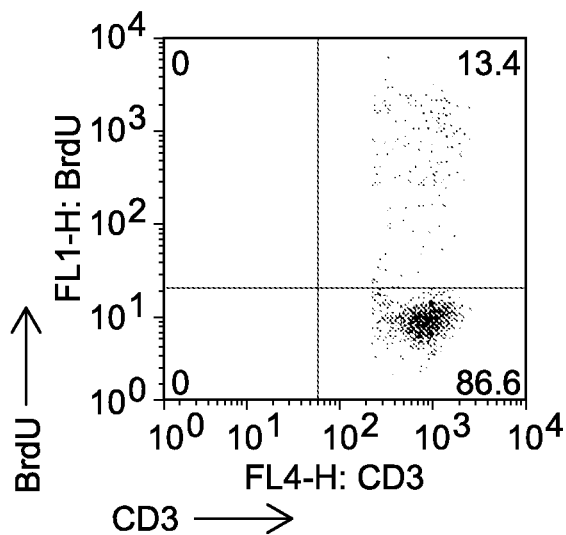
Panel A: Control
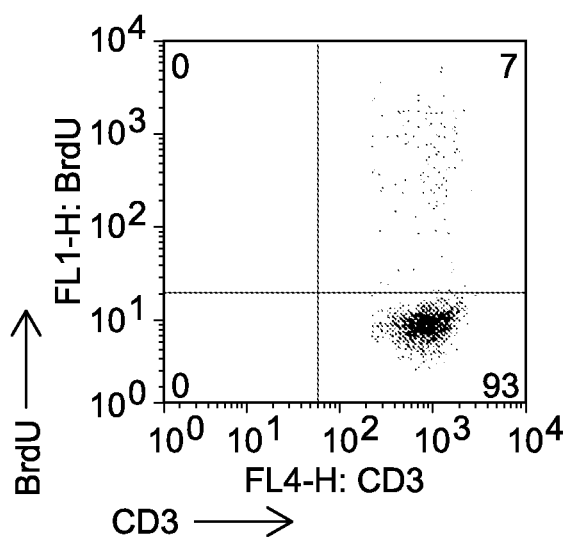
Panel B: Antibody 2D3
FIG. 16A

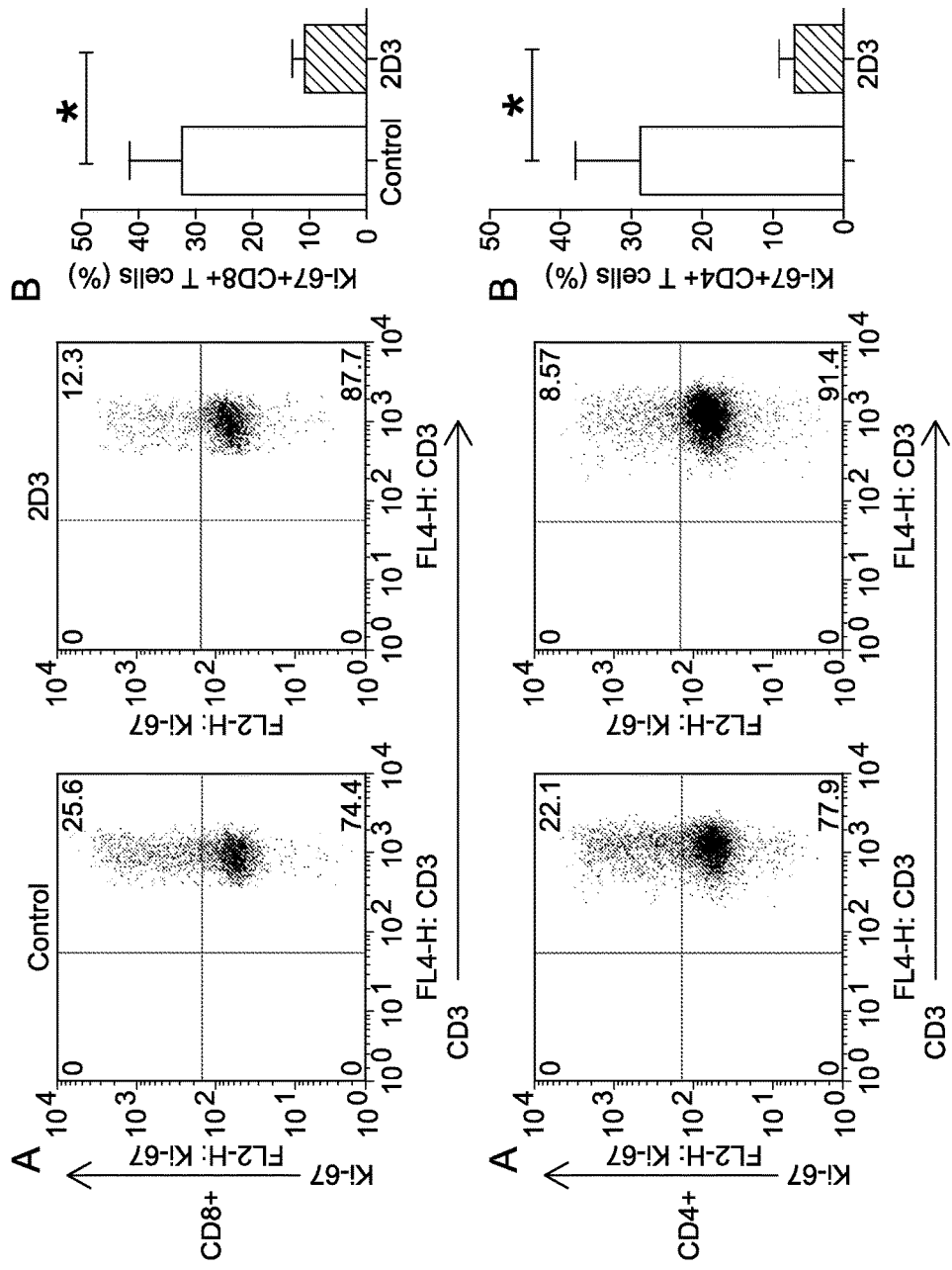
FIG. 17A-B

ANTI-B7-H5 ANTIBODIES AND THEIR USES

CROSS-REFERENCE TO RELATED APPLICATIONS

This application is the U.S. national phase application, pursuant to 35 U.S.C. § 371, of PCT international application Ser. No.: PCT/US2014/039621, filed May 27, 2014, designating the United States and published in English, which claims the benefit of the following U.S. Provisional Application No. 61/827,216, filed May 24, 2013, entitled "Anti-B7-H5 Antibodies and Their Uses," the entire contents of which are incorporated herein by reference.

STATEMENT REGARDING FEDERALLY SPONSORED RESEARCH OR DEVELOPMENT

This invention was made with government support under award numbers RO1 CA97085 and RO1 A172592 by the National Institutes of Health (NIH), and U19 CA113341 by the National Cancer Institute (NCI). The government has certain rights in the invention.

REFERENCE TO SEQUENCE LISTING

This application includes one or more Sequence Listings pursuant to 37 C.F.R. § 1.821 et seq., which are disclosed in both paper and computer-readable media, and which paper and computer-readable disclosures are herein incorporated by reference in their entirety.

FIELD OF THE INVENTION

The present invention relates to antibodies and their antigen-binding fragments and to other molecules that are capable of binding to the B7-H5 ligand of the B7-H5:CD28H pathway, and to the uses of such molecules in the treatment and diagnosis of autoimmune disease, transplant rejection and other inflammatory diseases.

BACKGROUND OF THE INVENTION

The immune system of humans and other mammals is responsible for providing protection against infection and disease. Such protection is provided both by a humoral immune response and by a cell-mediated immune response. The humoral response results in the production of antibodies and other biomolecules that are capable of recognizing and neutralizing foreign targets (antigens). In contrast, the cell-mediated immune response involves the activation of macrophages, natural killer cells (NK), and antigen-specific cytotoxic T-lymphocytes by T cells, and the release of various cytokines in response to the recognition of an antigen (Dong, C. et al. (2003) "*Immune Regulation by Novel Costimulatory Molecules*," Immunolog. Res. 28(1): 39-48).

The ability of T cells to optimally mediate an immune response against an antigen requires two distinct signaling interactions (Viglietta, V. et al. (2007) "*Modulating Co-Stimulation*," Neurotherapeutics 4:666-675; Korman, A. J. et al. (2007) "*Checkpoint Blockade in Cancer Immunotherapy*," Adv. Immunol. 90:297-339). First, antigen that has been arrayed on the surface of antigen-presenting cells (APC) must be presented to an antigen-specific naive CD4+ T cell. Such presentation delivers a signal via the T cell receptor (TCR) that directs the T cell to initiate an immune response that will be specific to the presented antigen. Second, a series of co-stimulatory and co-inhibitory signals, mediated through interactions between the APC and distinct T cell surface molecules, triggers first the activation and proliferation of the T cells and ultimately their inhibition. Thus, the first signal confers specificity to the immune response whereas the second signal serves to determine the nature, magnitude and duration of the response.

The immune system is tightly controlled by co-stimulatory and co-inhibitory ligands and receptors. These molecules provide the second signal for T cell activation and provide a balanced network of positive and negative signals to maximize immune responses against infection while limiting immunity to self (Wang, L. et al. (Mar. 7, 2011) "*VISTA, A Novel Mouse Ig Superfamily Ligand That Negatively Regulates T Cell Responses*," J. Exp. Med. 10.1084/jem.20100619:1-16; Lepenies, B. et al. (2008) "*The Role Of Negative Costimulators During Parasitic Infections*," Endocrine, Metabolic & Immune Disorders—Drug Targets 8:279-288). Of particular importance is binding between the B7.1 (CD80) and B7.2 (CD86) ligands of the Antigen Presenting Cell and the CD28 and CLTA-4 receptors of the CD4+ T-lymphocyte (Sharpe, A. H. et al. (2002) "*The B7-CD28 Superfamily*," Nature Rev. Immunol. 2:116-126; Dong, C. et al. (2003) "*Immune Regulation by Novel Costimulatory Molecules*," Immunolog. Res. 28(1):39-48; Lindley, P. S. et al. (2009) "*The Clinical Utility Of Inhibiting CD28-Mediated Costimulation*," Immunol. Rev. 229:307-321). Binding of B7.1 or of B7.2 to CD28 stimulates T cell activation; binding of B7.1 or B7.2 to CTLA4 inhibits such activation (Dong, C. et al. (2003) "*Immune Regulation by Novel Costimulatory Molecules*," Immunolog. Res. 28(1): 39-48; Lindley, P. S. et al. (2009) "*The Clinical Utility Of Inhibiting CD28-Mediated Costimulation*," Immunol. Rev. 229:307-321; Greenwald, R. J. et al. (2005) "*The B7 Family Revisited*," Ann. Rev. Immunol. 23:515-548). CD28 is constitutively expressed on the surface of T cells (Gross, J., et al. (1992) "*Identification And Distribution Of The Costimulatory Receptor CD28 In The Mouse*," J. Immunol. 149: 380-388), whereas CTLA4 expression is rapidly up-regulated following T-cell activation (Linsley, P. et al. (1996) "*Intracellular Trafficking Of CTLA4 And Focal Localization Towards Sites Of TCR Engagement*," Immunity 4:535-543). Since CTLA4 is the higher affinity receptor (Sharpe, A. H. et al. (2002) "*The B7-CD28 Superfamily*," Nature Rev. Immunol. 2:116-126), binding first initiates T cell proliferation (via CD28) and then inhibits it (via nascent expression of CTLA4), thereby dampening the effect when proliferation is no longer needed.

Further investigations into the ligands of the CD28 receptor have led to the identification and characterization of a set of related B7 molecules (the "B7 Superfamily") (Coyle, A. J. et al. (2001) "*The Expanding B7 Superfamily: Increasing Complexity In Costimulatory Signals Regulating T Cell Function*," Nature Immunol. 2(3):203-209; Sharpe, A. H. et al. (2002) "*The B7-CD28 Superfamily*," Nature Rev. Immunol. 2:116-126; Greenwald, R. J. et al. (2005) "*The B7 Family Revisited*," Ann. Rev. Immunol. 23:515-548; Collins, M. et al. (2005) "*The B7 Family Of Immune-Regulatory Ligands*," Genome Biol. 6:223.1-223.7; Loke, P. et al. (2004) "*Emerging Mechanisms Of Immune Regulation: The Extended B7 Family And Regulatory T Cells*." Arthritis Res. Ther. 6:208-214; Korman, A. J. et al. (2007) "*Checkpoint Blockade in Cancer Immunotherapy*," Adv. Immunol. 90:297-339; Flies, D. B. et al. (2007) "*The New B7s: Playing a Pivotal Role in Tumor Immunity*," J. Immunother. 30(3): 251-260; Agarwal, A. et al. (2008) "*The Role Of Positive Costimulatory Molecules In Transplantation And Toler-* ance," Curr. Opin. Organ Transplant. 13:366-372; Lenschow, D. J. et al. (1996) "*CD28/B7 System of T Cell Costimulation,*" Ann. Rev. Immunol. 14:233-258; Wang, S. et al. (2004) "*Co-Signaling Molecules Of The B7-CD28 Family In Positive And Negative Regulation Of T Lymphocyte Responses,*" Microbes Infect. 6:759-766). There are currently nine known members of the family: B7.1 (CD80), B7.2 (CD86), the inducible co-stimulator ligand (ICOS-L, B7-H2), the programmed death-1 ligand (PD-L1; B7-H1), the programmed death-2 ligand (PD-L2; B7-DC), B7-H3, B7-H4 (also referred to as B7x, B7-H6 and B7S1; Sica, G. L. et al. (2003) "*B7-4, A Molecule Of The B7 Family, Negatively Regulates T Cell Immunity,*" Immunity 18:849-861; Zang, X. et al. (2003) *B7x: A Widely Expressed B7 Family Member That Inhibits T Cell Activation,*" Proc. Natl. Acad. Sci. (USA) 100:10388-10392; Prasad, D. V. et al. (2003) *B7S1, A Novel B7 Family Member That Negatively Regulates T Cell Activation,*" Immunity 18:863-873), B7-H6 (Collins, M. et al. (2005) "*The B7 Family Of Immune-Regulatory Ligands,*" Genome Biol. 6:223.1-223.7) and B7-H5 (Flajnik, M. F. et al. (2012) "*Evolution Of The B7 Family: Co-Evolution Of B7H6 And Nkp30, Identification Of A New B7 Family Member, B7H7, And Of B7's Historical Relationship With The MHC,*" Immunogenetics 64:571-590). The B7 family of genes is essential in the regulation of the adaptive immune system. Most B7 family members contain both variable (V)- and constant (C)-type domains of the immunoglobulin superfamily (IgSF).

B7 ligands are expressed on the cell surface of many different cell types including antigen presenting cells (APCs) and their interaction with receptor molecules on T cells provide activating and/or inhibitory signals that regulate T cell activation and tolerance (Collins, M. et al. (2005) "*The B7 Family Of Immune-Regulatory Ligands,*" Genome Biol. 6:223.1-223.7). Some inhibitory B7 ligands are also expressed on tumor cells, resulting in suppression of immune responses (Keir, M. E. et al. (2008) "*PD-1 And Its Ligands In Tolerance And Immunity,*" Annu. Rev. Immunol. 26:677-704; Zou, W. et al. (2008) "*Inhibitory B7-Family Molecules In The Tumour Microenvironment,*" Nat. Rev. Immunol. 8:467-477). Therefore, stimulating or attenuating the interactions of B7 ligands and their receptors holds therapeutic potential for autoimmune diseases, cancer and infectious disease (WO 2011/020024; Flajnik, M. F. et al. (2012) "*Evolution Of The B7 Family: Co-Evolution Of B7H6 And Nkp30, Identification Of A New B7 Family Member, B7H7, And Of B7's Historical Relationship With The MHC,*" Immunogenetics 64:571-590).

Despite all prior advances in the treatment of inflammatory disease or autoimmune disease, a need remains for compositions capable of providing enhanced immunotherapy for the treatment of such conditions. The present invention is directed to such compositions and their use to treat inflammatory disease, autoimmune disease, and similar diseases and conditions characterized by a hyperactive immune system.

SUMMARY OF THE INVENTION

Antibodies and their antigen-binding fragments and other molecules that are capable of immunospecifically binding to the B7-H5 ligand of the B7-H5:CD28H pathway, and to the uses of such molecules in the treatment and diagnosis of autoimmune disease, transplant rejection and other inflammatory diseases are provided.

One embodiment provides an antibody or other molecule having an antigen-binding fragment of an antibody that immunospecifically binds to a mammalian B7-H5 (and in particular, a human B7-H5). The B7-H5 can be, for example, arrayed on the surface of a live cell.

Exemplary live cells include, but are not limited to macrophage or dendritic cells.

Another embodiment provides a molecule that immunospecifically binds to B7-H5 and is substantially capable of blocking B7-H5's interaction with CD28H. Still another embodiment provides a molecule that immunospecifically binds to B7-H5 and is substantially incapable of blocking B7-H5's interaction with CD28H.

The B7-H5 binding molecules can have antigen-binding fragments that contain six CDRs. The CDRs can include at least one consensus CDR of the CDRs of anti-B7-H5 antibodies: 2D3 and 18C3, with all remaining CDRs selected from:
  (A) the three light chain and the three heavy chain CDRs of anti-B7-H5 antibody 2D3; or
  (B) the three light chain and the three heavy chain CDRs of anti-B7-H5 antibody 18C3.

Another embodiment provides B7-H5 binding molecules wherein the six CDRs are:
  (A) the three light chain and the three heavy chain CDRs of anti-B7-H5 antibody 2D3; or
  (B) the three light chain and the three heavy chain CDRs of anti-B7-H5 antibody 18C3.

In some embodiments, the molecule is a chimeric antibody that includes antigen binding fragments (Fab) from two or more different B7-H5 antibodies.

The B7-H5 binding molecules can be a monoclonal antibody, a human antibody, a chimeric antibody or a humanized antibody and/or is a bispecific, trispecific or multispecific antibody.

The B7-H5 binding molecules can be detectably labeled or include a conjugated toxin, drug, receptor, enzyme, or receptor ligand.

Still another embodiment provides a pharmaceutical composition containing a therapeutically effective amount or a prophylactically effective amount of any of the above-described B7-H5 binding molecules and a physiologically acceptable carrier or excipient.

In other embodiments, a molecule that is substantially capable of blocking B7-H5's interaction with CD28H is an CD28H fusion protein, preferably an CD28H-Ig fusion protein.

Methods of using the pharmaceutical compositions in the treatment of a disease are also provided.

A method for diagnosing a disease in a subject includes assaying cells of the subject for their ability to bind to any of the above-described B7-H5 binding molecules, wherein the method provides a cytologic assay for diagnosing the presence of a disease in the subject.

The disclosed B7-H5 binding molecules can be used to an autoimmune disease or transplant rejection.

BRIEF DESCRIPTION OF THE DRAWINGS

In the Figures and the descriptions thereof as set forth herein, "B7-H5" is also referred to as "B7-H7." In addition, "CD28H" is also referred to as "H7CR." Accordingly, the terms "B7-H5" and "B7-H7" are used interchangeably, and the terms "CD28H" and "H7CR" are used interchangeably, throughout the Figures and descriptions thereof in this disclosure.

FIGS. 12A-12C show the ability of anti-human B7-H5 antibodies (2D3 and 18C3) that had been recombinantly converted from their murine IgG isotype to a human IgG4 isotype to bind human B7-H5 expressed by CHO cells.

FIG. 14A and FIG. 14B show that 2D3 and 18C3 recognize the first IgV domain of B7-H5.

FIGS. 16A-16B show the effect of the endogenous B7-H5:CD28H interaction on the recall of TT-specific memory T cells. FIG. 16A shows TT vaccine-induced T cell proliferation in the presence of the B7-H5:CD28H interaction blocking antibody 2D3 (Panel B) or control Igs (Panel A). FIG. 16B shows the levels of expressed cytokines (Panel A) and the BrdU-positive cells (Panel B) associated with such response.

FIGS. 17A-17B show the blockade of endogenous B7-H5:CD28H interaction by 2D3 inhibits the allogeneic proliferative responses of both CD8+(FIG. 17A, Panels A-B) and CD4+(FIG. 17B, Panels A-B) T cells in humanized NSG mice.

DETAILED DESCRIPTION OF THE INVENTION

The present invention relates to antibodies and their antigen-binding fragments and to other molecules that are capable of immunospecifically binding to the B7-H5 ligand of the B7-H5:CD28H pathway, and to the uses of such molecules in the treatment and diagnosis of autoimmune disease, transplant rejection and other inflammatory diseases.

Figure 1:
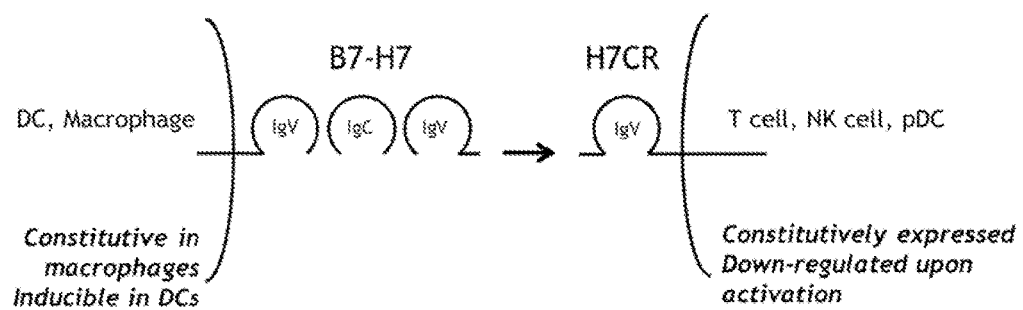
FIG. 1 provides a schematic depiction of B7-H5 and its counter-receptor, CD28H.
Figure 2:
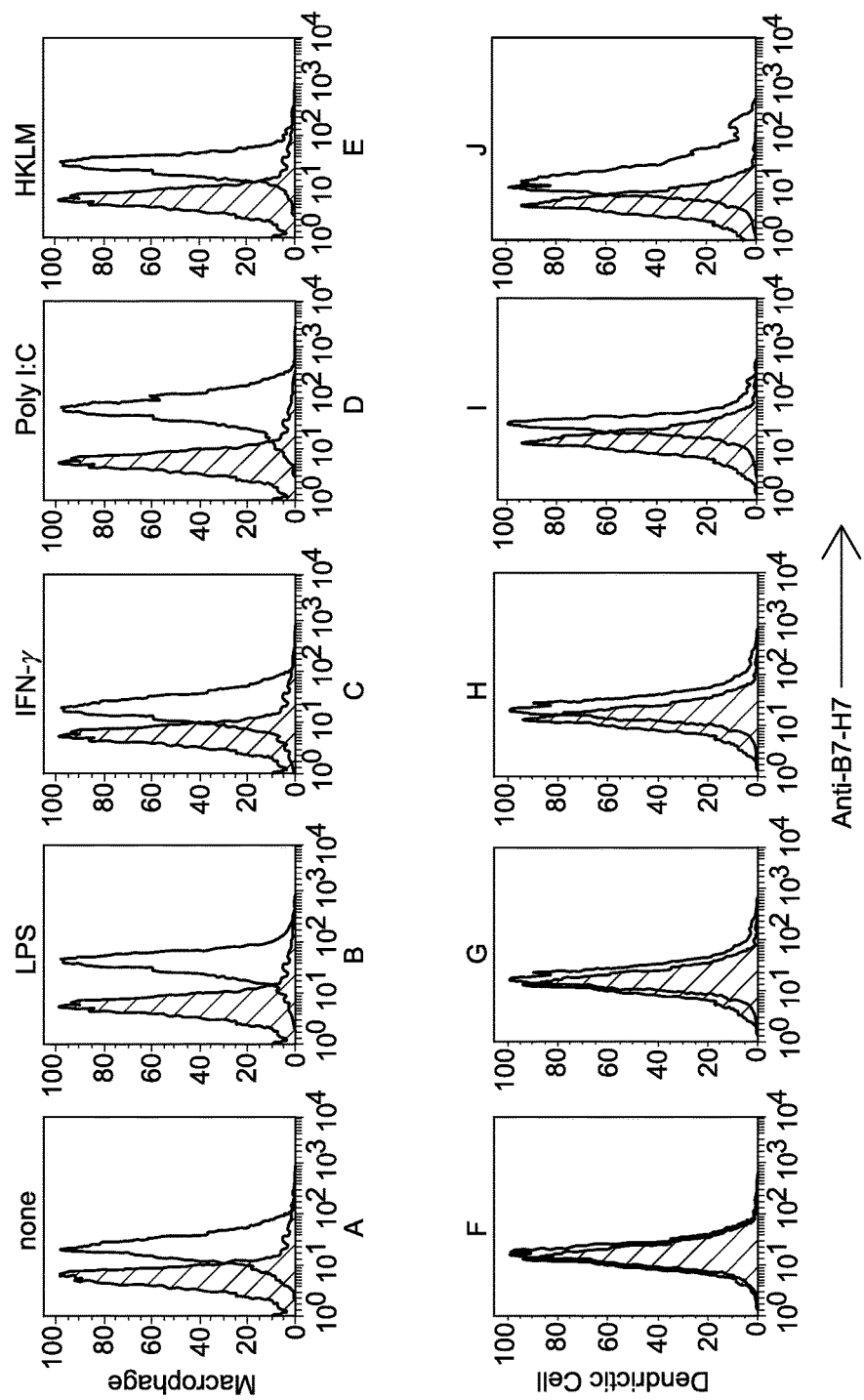
FIG. 2, Panels A-J, show that B7-H5 is constitutively expressed on macrophages and inducible on dendritic cells.
Figure 3A:
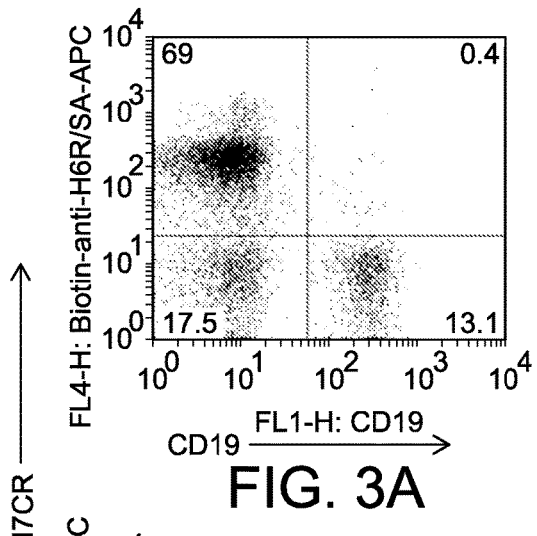
FIG. 3, Panels A-D, show that CD28H is expressed on T cells and natural killer (NK) cells, but not on B cells.
Figure 3B:
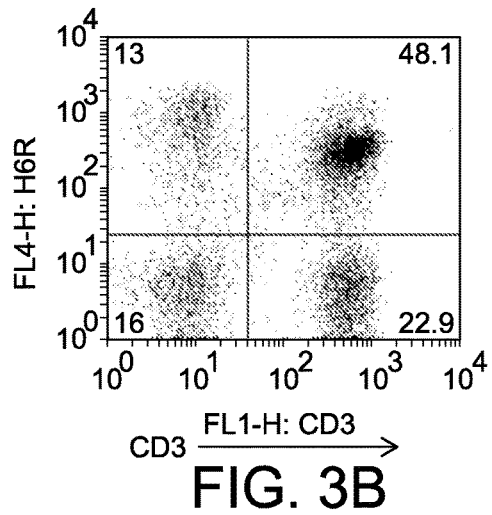
Figure 3C:
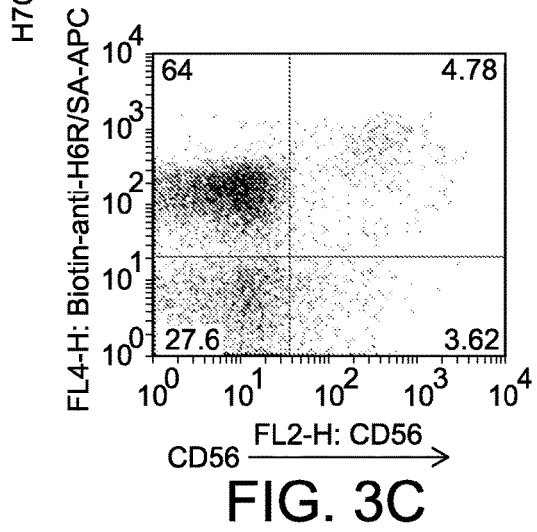
Figure 3D:
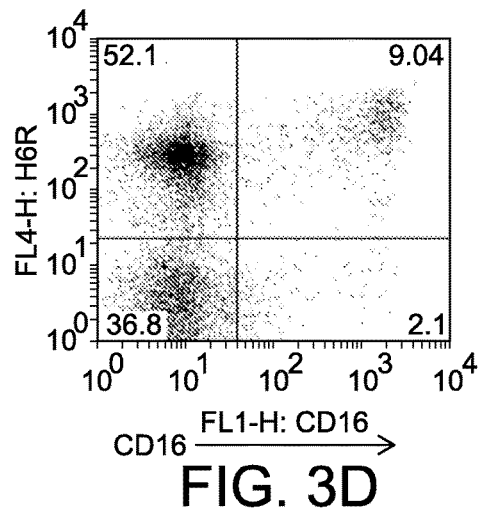

The B7-H5:CD28H pathway is a cellular immunity pathway that involves the ligand B7-H5 and its counter-receptor CD28H (FIG. 1). B7-H5 is expressed on antigen presenting cells; it is constitutively expressed on macrophages and inducible on dendritic cells (FIG. 2, Panels A-J). CD28H is particularly expressed on naïve T cells, NK cells, and plasmacytoid dendritic cells (especially in the spleen, lymph node and *thymus*), and its expression is down-regulated on matured or activated cells. It is not expressed on γδ T cells or B cells (FIG. 3), but is expressed on $T_n$, $T_{CM}$, $T_{EM}$, and $T_{EMRA}$ T cell subsets. Human cord blood T cells express CD28H as do CD4$^+$, CD8$^+$ and CD4$^+$/CD8$^+$ thymocytes. B7-H5 interacts with the CD28H counter-receptor to stimulate the immune system, thereby promoting enhanced immune responses. Down-regulation of CD28H has been found to impair activated/memory T cell survival in vivo. Thus, the interaction between B7-H5 and CD28H is important for native T cell priming and activated/memory T cell survival in vivo. CD28H is also seen to be down-regulated in chronically antigen-exposed/exhausted T cells. CD28H is constitutively expressed on Natural Killer cell (NK). B7-H5-CD28H pathway promotes NK activation and degranulation in the presence of other NK activation signal, such as CD16 crosslinking.

The present invention reflects, in part, the recognition that molecules, such as antibodies and their antigen binding fragments that immunospecifically bind to B7-H5 ("anti-B7-H5 antibodies"), and particularly anti-B7-H5 antibodies or decoy receptor fusion protein CD28HIg that block the B7-H5:CD28H interaction so as to impair (i.e., prevent or attenuate) the ability of B7-H5 to bind to CD28H, are capable of impairing the ability of B7-H5 to promote enhanced immune responses via the CD28H interaction, and thus are capable of serving as antagonists of T cell proliferation and cytokine production and NK activation. Such molecules are capable of mediating a physiological reduction in immune system activation and thus have utility in the treatment of inflammatory disease and autoimmune disease. In particular, such antibodies are capable of reducing the percentage of activated T cells and NK cells in vivo.

A. B7-H5

The B7-H5 amino acid sequence was found to be similar to a previously discovered human gene, HHLA2 (human endogenous retrovirus-H long terminal repeat-associating protein 2 (HHLA2); Mager, D. L. et al. (1999) "*Endogenous Retroviruses Provide The Primary Polyadenylation Signal For Two New Human Genes (HHLA2 And HHLA3*," Genomics 59:255-263), that had no known function (Flajnik, M. F. et al. (2012) "*Evolution Of The B7 Family: Co-Evolution Of B7H6 And Nkp30, Identification Of A New B7 Family Member, B7H7, And Of B7's Historical Relationship With The MHC*," Immunogenetics 64:571-590). B7-H5 is also referred to herein and elsewhere as B7-H7. Accordingly, the terms B7-H5 and B7-H7 are used interchangeably herein.

The human B7-H5 sequence has been found to have homologs in chicken, opossum, hoofed mammals (e.g., horse, pig), salmon, and shark. However, only pseudogenes have been thus far identified in rodents (mouse and rat). The amino acid sequences of such genes reveal a similar domain structures in all species, with conservation of the canonical residues for Ig superfamily domains.

Human B7-H5 polypeptide is 414 amino acids in length and has been reported to contain the following: a signal sequence, an extracellular domain having 3 immunoglobulin-like (Ig-like) domains, a transmembrane domain, and a cytoplasmic domain. In particular, the human B7-H5 polypeptide has been reported to contain an Ig-like V-type 1 domain, an Ig-like C-1 type domain, and an Ig-like V-type 2 domain. Multiple naturally occurring variants of B7-H5 exist (e.g., Accession No. Q9UM44-1 (*homo sapiens*), NP_009003 (GI: 5901964, *homo sapiens*), and AAD48396 (GI: 15726285, *homo sapiens*); see WO 2011/020024).

The term "native-B7-H5" (also "native-B7-H7") refers to any naturally occurring B7-H5 amino acid sequence, including immature or precursor and mature forms. The amino acid sequence of a representative human B7-H5, Accession No. Q9UM44-1, is (SEQ ID NO:1):

```
MKAQTALSFF LILITSLSGS QGIFPLAFFI YVPMNEQIVI

GRLDEDIILP SSFERGSEVV IHWKYQDSYK VHSYYKGSDH

LESQDPRYAN RTSLFYNEIQ NGNASLFFRR VSLLDEGIYT

CYVGTAIQVI TNKVVLKVGV FLTPVMKYEK RNTNSFLICS

VLSVYPRPII TWKMDNTPIS ENNMEETGSL DSFSINSPLN

ITGSNSSYEC TIENSLLKQT WTGRWTMKDG LHKMQSEHVS

LSCQPVNDYF SPNQDFKVTW SRMKSGTFSV LAYYLSSSQN

TIINESRFSW NKELINQSDF SMNLMDLNLS DSGEYLCNIS

SDEYTLLTIH TVHVEPSQET ASHNKGLWIL VPSAILAAFL

LIWSVKCCRA QLEARRSRHP ADGAQQERCC VPPGERCPSA

PDNGEENVPL SGKV
```

The human B7-H5 has been reported to contain the following: a signal sequence at approximately amino acid residues 1 to 22 of SEQ ID NO:1, an Ig-like V-type 1 domain (shown underlined above) at approximately amino acid residues 61 to 131 of SEQ ID NO:1, an Ig-like C-1 type domain at approximately amino acid residues 138 to 222 of SEQ ID NO:1, an Ig-like V-type 2 domain at approximately amino acid residues 235 to 328 of SEQ ID NO:1, and a transmembrane domain at approximately amino acid residues 345 to 365 of SEQ ID NO:1. The predicted dimer interface for human B7-H5 polypeptide is amino acid residues 141-144, 156, 158, 160, 162, 193-196, 198, 200, 201, 224, and 225 of SEQ ID NO:1. The predicted N-linked glycosylation sites for human B7-H5 polypeptide are at amino acid residues 90, 103, and 318 of SEQ ID NO:1. Natural variations of human B7-H5 polypeptide include B0T, N344K, and S346R (UniProt Q9UM44) (see, WO 2011/020024, which reference is herein incorporated by reference in its entirety for its teaching of the structure and sequence of human B7-H5).

A DNA sequence encoding human B7-H5 (SEQ ID NO:1) is (SEQ ID NO:2):

```
atgaaggcac agacagcact gtctttcttc ctcattctca taacatctct gagtggatct caaggcatat tccctttggc tttcttcatt tatgttccta tgaatgaaca aatcgtcatt ggaagacttg atgaagatat aattctccct tcttcatttg agagggatc cgaagtcgta atacactgga agtatcaaga tagctataag gttcatagtt actacaaagg cagtgaccat ttggaaagcc aagatcccag atatgcaaac aggacatccc ttttctataa tgagattcaa aatgggaatg cgtcactatt tttcagaaga gtaagccttc tggacgaagg aatttacacc tgctatgtag gaacagcaat tcaagtgatt acaaacaaag tggtgctaaa ggtgggagtt tttctcacac ccgtgatgaa gtatgaaaag aggaacacaa acagcttctt aatatgcagc gtgttaagtg tttatcctcg tccaattatc acgtggaaaa tggacaacac acctatctct gaaaacaaca tggaagaaac agggtctttg gattcttttt ctattaacag cccactgaat attacaggat caaattcatc ttatgaatgt acaattgaaa attcactgct gaagcaaaca tggacagggc gctggacgat gaaagatggc cttcataaaa tgcaaagtga acacgtttca ctctcatgtc aacctgtaaa tgattatttt tcaccaaacc aagacttcaa agttacttgg tccagaatga aaagtgggac tttctctgtc ctggcttact atctgagctc ctcacaaaat acaattatca atgaatcccg attctcatgg aacaaagagc tgataaacca gagtgacttc tctatgaatt tgatggatct taatctttca gacagtgggg aatatttatg caatatttct tcggatgaat atactttact taccatccac acagtgcatg tagaaccgag ccaagaaaca gcttcccata acaaaggctt atggattttg gtgccctctg cgatttggc agcttttctg ctgatttgga gcgtaaaatg ttgcagagcc cagctagaag
```

```
ccaggaggag cagacaccct gctgatggag cccaacaaga aagatgttgt gtccctcctg gtgagcgctg tcccagtgca cccgataatg gcgaagaaaa tgtgcctctt tcaggaaaag ta
```

The amino acid sequence of a representative human B7-H5 IgV domain human IgG4 fusion protein is (SEQ ID NO:3) (B7-H5 sequences are shown in boldface; IgG4 sequences are shown underlined):

```
IFPLAFFIYV  PMNEQIVIGR  LDEDIILPSS  FERGSEVVIH

WKYQDSYKVH  SYYKGSDHLE  SQDPRYANRT  SLFYNEIQNG

NASLFFRRVS  LLDEGIYTCY  VGTAIQVITN  KVVLKVGVFL

TPVMKYEKES  KYGPPCPPCP  APEFLGGPSV  FLFPPKPKDT

LMISRTPEVT  CVVVDVSQED  PEVQFNWYVD  GVEVHNAKTK

PREEQFNSTY  RVVSVLTVLH  QDWLNGKEYK  CKVSNKGLPS

SIEKTISKAK  GQPREPQVYT  LPPSQEEMTK  NQVSLTCLVK

GFYPSDIAVE  WESNGQPENN  YKTTPPVLDS  DGSFFLYSRL

TVDKSRWQEG  NVFSCSVMHE  ALHNHYTQKS  LSLSPG
```

The fusion protein may additionally comprise an N-terminal leader sequence (such residues 1-22 of SEQ ID NO:1, i.e., the naturally occurring B7-H5 leader sequence (SEQ ID NO:4):

```
        MKAQTALSFF  LILITSLSGS  QG
```

A DNA sequence encoding the naturally occurring B7-H5 leader sequence is (SEQ ID NO:5):

```
atgaaggccc agaccgccct gtccttcttc ctgatcctga tcacctccct gtccggcagc caggga
```

Although the B7-H5 sequences are shown fused to a human IgG4 region, in accordance with the present invention, such sequences can alternatively be fused to any Ig isotype, or indeed to any other protein.

A DNA sequence encoding human B7-H5IgV-hIgG4 (SEQ ID NO:3) is (SEQ ID NO:6):

```
atcttccctc tggccttctt catctacgtg cccatgaacg agcagatcgt gatcggccgg ctggacgagg atattatcct gccctccagc ttcgagcggg gctccgaggt cgtgatccac tggaagtacc aggactccta caaggtgcac tcctactaca agggctccga ccacctggaa tcccaggacc ccagatacgc caaccggacc agcctgttct acaacgagat ccagaacggc aacgcctccc tgttcttccg gcgagtgtcc ctgctggatg agggcatcta cacctgttac gtgggcaccg ccatccaagt gatcaccaac aaggtggtgc tgaaagtggg cgtgttcctg accccgtga tgaagtacga gaaagagtct aagtacggcc
```

```
ctccctgccc cccttgtcct gccctgaat ttctgggcgg accctctgtg ttcctgttcc ccccaaagcc caaggacacc ctgatgatct cccggacccc cgaagtgacc tgcgtggtgg tggatgtgtc ccaggaagat cccgaggtgc agttcaattg gtacgtggac ggcgtggaag tgcacaacgc caagaccaag cccagagagg aacagttcaa ctccacctac cgggtggtgt ccgtgctgac cgtgctgcac caggattggc tgaacggcaa agagtacaag tgcaaggtgt ccaacaaggg cctgcccagc tccatcgaaa agaccatctc caaggccaag gccagcccc gggaacccca ggtgtacaca ctgcctccaa gccaggaaga gatgaccaag aaccaggtgt ccctgacctg tctcgtgaag ggcttctacc cctccgatat cgccgtggaa tgggagtcca acggccagcc tgagaacaac tacaagacca ccccccctgt gctggactcc gacggctctt tcttcctgta ctcccgcctg accgtggaca agtccagatg gcaggaaggc aacgtgttct cctgctccgt gatgcacgag gccctgcaca accactacac ccagaagtcc ctgtccctga gccccggc
```

An amino acid sequence of a representative human B7-H5 human IgG4P fusion protein is including the extracellular domain of B7-H5 is (SEQ ID NO:24) (B7-H5ECD-hIgG4P with B7-H5 ECD aa1-340 underlined, and the Serine 228 to Proline mutation double underline)

IFPLAFFIYVPMNEQIVIGRLDEDIILPSSFERGSEVVIHWKYQDSYKVH

SYYKGSDHLESQDPRYANRTSLFYNEIQNGNASLFERRVSLLDEGIYTCY

VGTAIQVITNKVVLKVGVELTPVMKYEKRNTNSFLICSVLSVYPRPIITW

KMDNTPISENNMEETGSLDSFSINSPLNITGSNSSYECTIENSLLKQTWT

GRWTMKDGLHKMQSEHVSLSCQPVNDYFSPNQDFKVTWSRMKSGTFSVLA

YYLSSSQNTIINESRFSWNKELINQSDFSMNLMDLNLSDSGEYLCNISSD

EYTLLTIHTVHVEPSQETESKYGPPCPPCPAPEFLGGPSVFLEPPKPKDT

LMISRTPEVTCVVVDVSQEDPEVQFNWYVDGVEVHNAKTKPREEQFNSTY

RVVSVLTVLHQDWLNGKEYKCKVSNKGLPSSIEKTISKAKGQPREPQVYT

LPPSQEEMTKNQVSLTCLVKGFYPSDIAVEWESNGQPENNYKTTPPVLDS

DGSFELYSRLTVDKSRWQEGNVESCSVMHEALHNHYTQKSLSLSPG

The signal sequence can be the native signal sequence (SEQ ID NO:29)

```
        MKAQTALSFFLILITSLSGSQG
```

The fusion protein can be encoded by the nucleic acid sequence (SEQ ID NO:25)

```
atgaaggccc agaccgccct gtccttcttc ctgatcctga tcacctccct gtccggcagc cagggaatct tccctctggc cttcttcatc tacgtgccca tgaacgagca gatcgtgatc ggccggctgg acgaggatat tatcctgccc
```

-continued

```
tccagcttcgagcggggctccgaggtcgtgatccactggaagtaccagga
ctcctacaaggtgcactcctactacaagggctccgaccacctggaatccc
aggacccagatacgccaaccggaccagcctgttctacaacgagatccag
aacggcaacgcctccctgttcttccggcgagtgtccctgctggatgaggg
catctacacctgttacgtgggcaccgccatccaagtgatcaccaacaagg
tggtgctgaaagtgggcgtgttcctgaccccgtgatgaagtacgagaag
cggaataccaactctttcctgatctgctccgtgctgtccgtgtaccctcg
gcccatcatcacctggaagatggacaacaccccatctccgagaacaaca
tggaagagacaggctccctggactccttctccatcaactcccccctgaac
attaccggctccaactcctcctacgagtgcaccatcgagaactccctgct
gaagcagacctggaccggcagatggactatgaaggacggcctgcacaaga
tgcagtccgagcacgtgtccctgtcctgccagcccgtgaacgactacttc
agccccaaccaggacttcaaagtgacctggtcccggatgaagtccggcac
cttcagcgtgctggcctactacctgtccagctcccagaacaccatcatca
acgagtcccggttctcctggaacaaagagctgatcaaccagtccgacttc
tccatgaacctgatggacctgaacctgtccgacagcggcgagtacctgtg
caacatctccagcgacgagtacaccctgctgaccatccacaccgtgcacg
tggaaccctcccaggaaaccgagtctaagtacggccctccctgcccacct
tgtcccgcccctgaatttctgggcggaccctctgtgttcctgttccccc
aaagcccaaggacaccctgatgatctcccggaccccgaagtgacatgcg
tggtggtggatgtgtcccaggaagatcccgaggtgcagttcaattggtac
gtggacggcgtggaagtgcacaacgccaagaccaagcccagagaggaaca
gttcaactccacctaccgggtggtgtctgtgctgaccgtgctgcaccagg
actggctgaacggcaaagagtacaagtgcaaggtgtccaacaagggcctg
cccagctccatcgaaaagaccatctccaaggccaagggccagccccggga
accccaggtgtacacactgcctccaagccaggaagagatgaccaagaacc
aggtgtccctgacttgcctcgtgaagggcttctaccctccgatatcgcc
gtggaatgggagtccaacggccagcctgagaacaactacaagaccacccc
ccctgtgctggactccgacggctcttctcctgtactcccgcctgaccg
tggacaagtccagatggcaggaaggcaacgtgttcctcctgcagcgtgatg
cacgaggccctgcacaaccactacacccagaagtccctgagcctgtcccc
cggctga
```

In contrast to human B7-H4 which is widely expressed, human B7-H5 is found to exhibit more limited expression (e.g., expressed in the gut, kidney, lung, epithelial cells and lymphocytes). Human HHLA2 is found on chromosome 3q13.33 near B7.1 and B7.2. B7-H5 is constitutively expressed on macrophages and inducible on dendritic cells (DC).

B. CD28H

CD28H, also referred to herein and elsewhere as H7CR, is the counter-receptor for B7-H5. Accordingly, the terms CD28H and H7CR are used interchangeably herein. As used herein, the term "native CD28H" (also "native H7CR") refers to the naturally occurring counter-receptor of B7-H5, or variations thereof. CD28H is expressed by T cells, NK cells, and plasmacytoid dendritic cells. The human CD28H polypeptide is otherwise referred to as transmembrane and immunoglobulin domain containing 2 (TMIGD2) in the literature/databases (Rahimi, N. et al. (Epub 2012 March 14) "*Identification Of IGPR-1 As A Novel Adhesion Molecule Involved In Angiogenesis*," Molec. Biol. Cell. 23(9):1646-1656) but the function of CD28H was not previously elucidated. Non-limiting examples of Accession Numbers for the amino acid sequence of such native CD28H molecules include: Q96BF3-1 (*homo sapiens*), Q96BF3-2 (*homo sapiens*), NP_653216.1 (GI: 21389429; *homo sapiens*) and NP_653216.2 (GI: 281306838; *homo sapiens*). A representative amino acid sequence (Q96BF3-2) of the native CD28H molecule is provided below as SEQ ID NO:7:

```
MGSPGMVLGL LVQIWALQEA SSLSVQQGPN LLQVRQGSQA
TLVCQVDQAT AWERLRVKWT KDGAILCQPY ITNGSLSLGV
CGPQGRLSWQ APSHLTLQLD PVSLNHSGAY VCWAAVEIPE
LEEAEGNITR LFVDPDDPTQ NRNRIASFPG FLFVLLGVGS
MGVAAIVWGA WFWGRRSCQQ RDSGNSPGNA FYSNVLYRPR
GAPKKSEDCS GEGKDQRGQS IYSTSFPQPA PRQPHLASRP
CPSPRPCPSP RPGHPVSMVR VSPRPSPTQQ PRPKGFPKVG
EE
```

A DNA sequence encoding human CD28H (SEQ ID NO:7) is (SEQ ID NO:8):

```
atgggtccc  cgggcatggt  gctgggcctc  ctggtgcaga
tctgggccct  gcaagaagcc  tcaagcctga  gcgtgcagca
ggggcccaac  ttgctgcagg  tgaggcaggg  cagtcaggcg
acccctggtct  gccaggtgga  ccaggccaca  gcctgggaac
ggctccgtgt  taagtggaca  aaggatgggg  ccatcctgtg
tcaaccgtac  atcaccaacg  gcagcctcag  cctggggtc
tgcgggcccc  agggacggct  ctcctggcag  gcacccagcc
atctcaccct  gcagctggac  cctgtgagcc  tcaaccacag
cggggcgtac  gtgtgctggg  cggccgtaga  gattcctgag
ttggaggagg  ctgagggcaa  cataacaagg  ctctttgtgg
acccagatga  ccccacacag  aacagaaacc  ggatcgcaag
cttcccagga  ttcctcttcg  tgctgctggg  ggtgggaagc
atgggtgtgg  ctgcgatcgt  gtggggtgcc  tggttctggg
gccgccgcag  ctgccagcaa  agggactcag  gtaacagccc
aggaaatgca  ttctacagca  acgtcctata  ccggccccgg
ggggcccaa  agaagagtga  ggactgctct  ggagagggga
aggaccagag  gggccagagc  atttattcaa  cctccttccc
gcaaccggcc  cccgccagc   cgcacctggc  gtcaagaccc
tgcccagcc   cgagaccctg  ccccagcccc  aggcccggcc
accccgtctc  tatggtcagg  gtctctccta  gaccaagccc
```

-continued

```
cacccagcag ccgaggccaa aagggttccc caaagtggga gaggag
```

C. Definitions

As used herein, a molecule is said to be able to "immunospecifically bind" a second molecule if such binding exhibits the specificity and affinity of an antibody to its cognate antigen. Antibodies are said to be capable of "immunospecifically binding" to a target region or conformation ("epitope") of an antigen (and in particular, the antigen B7-H5) if such binding involves the antigen recognition site of the immunoglobulin molecule. An antibody that immunospecifically binds to a particular antigen may bind to other antigens with lower affinity if the other antigen has some sequence or conformational similarity that is recognized by the antigen recognition site as determined by, e.g., immunoassays, BIACORE® assays, or other assays known in the art, but would not bind to a totally unrelated antigen. Preferably, however, antibodies (and their antigen binding fragments) will not cross-react with other antigens. Antibodies may also bind to other molecules in a way that is not immunospecific, such as to FcR receptors, by virtue of binding domains in other regions/domains of the molecule that do not involve the antigen recognition site, such as the Fc region.

The term "substantially," as used in the context of binding or exhibited effect, is intended to denote that the observed effect is physiologically or therapeutically relevant. Thus, for example, a molecule is able to substantially block an activity of B7-H5 if the extent of blockage is physiologically or therapeutically relevant (for example if such extent is greater than 60% complete, greater than 70% complete, greater than 75% complete, greater than 80% complete, greater than 85% complete, greater than 90% complete, greater than 95% complete, or greater than 97% complete). Similarly, a molecule is said to have substantially the same immunospecificity and/or characteristic as another molecule, if such immunospecificities and characteristics are greater than 60% identical, greater than 70% identical, greater than 75% identical, greater than 80% identical, greater than 85% identical, greater than 90% identical, greater than 95% identical, or greater than 97% identical).

As used herein, the term "subject" is intended to denote a mammal such as a non-primate (e.g., cows, pigs, horses, cats, dogs, rats etc.) and a primate (e.g., monkey and human), most preferably a human. The term "patient" is intended to denote a subject receiving a composition of the present invention for a diagnostic, therapeutic or prophylactic purpose.

As used herein, the term "antibody" is intended to denote an immunoglobulin molecule that possesses a "variable region" antigen recognition site. The term "variable region" is intended to distinguish such domain of the immunoglobulin from domains that are broadly shared by antibodies (such as an antibody Fc domain). The variable region comprises a "hypervariable region" whose residues are responsible for antigen binding. The hypervariable region comprises amino acid residues from a "Complementarity Determining Region" or "CDR" (i.e., typically at approximately residues 24-34 (L1), 50-56 (L2) and 89-97 (L3) in the light chain variable domain and at approximately residues 27-35 (H1), 50-65 (H2) and 95-102 (H3) in the heavy chain variable domain; Kabat et al., Sequences of Proteins of Immunological Interest, 5th Ed. Public Health Service, National Institutes of Health, Bethesda, Md. (1991)) and/or those residues from a "hypervariable loop" (i.e., residues 26-32 (L1), 50-52 (L2) and 91-96 (L3) in the light chain variable domain and 26-32 (H1), 53-55 (H2) and 96-101 (H3) in the heavy chain variable domain; Chothia and Lesk, 1987, J. Mol. Biol. 196:901-917). "Framework Region" or "FR" residues are those variable domain residues other than the hypervariable region residues as herein defined. The term antibody includes monoclonal antibodies, multi-specific antibodies, human antibodies, humanized antibodies, synthetic antibodies, chimeric antibodies, camelized antibodies (See e.g., Muyldermans et al., 2001, Trends Biochem. Sci. 26:230; Nuttall et al., 2000, Cur. Pharm. Biotech. 1:253; Reichmann and Muyldermans, 1999, J. Immunol. Meth. 231:25; International Publication Nos. WO 94/04678 and WO 94/25591; U.S. Pat. No. 6,005,079), single-chain Fvs (scFv) (see, e.g., see Pluckthun in The Pharmacology of Monoclonal Antibodies, vol. 113, Rosenburg and Moore eds. Springer-Verlag, New York, pp. 269-315 (1994)), single chain antibodies, disulfide-linked Fvs (sdFv), intrabodies, and anti-idiotypic (anti-Id) antibodies (including, e.g., anti-Id and anti-anti-Id antibodies to the disclosed B7-H5 antibodies). In particular, such antibodies include immunoglobulin molecules of any type (e.g., IgG, IgE, IgM, IgD, IgA and IgY), class (e.g., IgG1, IgG2, IgG3, IgG4, IgA1 and IgA2) or subclass.

As used herein, the term "antigen binding fragment" of an antibody refers to one or more portions of an antibody that contain the antibody's Complementarity Determining Regions ("CDRs") and optionally the framework residues that comprise the antibody's "variable region" antigen recognition site, and exhibit an ability to immunospecifically bind antigen. Such fragments include Fab', F(ab')2, Fv, single chain (ScFv), and mutants thereof, naturally occurring variants, and fusion proteins comprising the antibody's "variable region" antigen recognition site and a heterologous protein (e.g., a toxin, an antigen recognition site for a different antigen, an enzyme, a receptor or receptor ligand, etc.). As used herein, the term "fragment" refers to a peptide or polypeptide comprising an amino acid sequence of at least 5 contiguous amino acid residues, at least 10 contiguous amino acid residues, at least 15 contiguous amino acid residues, at least 20 contiguous amino acid residues, at least 25 contiguous amino acid residues, at least 40 contiguous amino acid residues, at least 50 contiguous amino acid residues, at least 60 contiguous amino residues, at least 70 contiguous amino acid residues, at least 80 contiguous amino acid residues, at least 90 contiguous amino acid residues, at least 100 contiguous amino acid residues, at least 125 contiguous amino acid residues, at least 150 contiguous amino acid residues, at least 175 contiguous amino acid residues, at least 200 contiguous amino acid residues, or at least 250 contiguous amino acid residues.

Human, chimeric or humanized derivatives of anti-human B7-H5 antibodies are particularly preferred for in vivo use in humans, however, murine antibodies or antibodies of other species may be advantageously employed for many uses (for example, in vitro or in situ detection assays, acute in vivo use, etc.). A humanized antibody may comprises amino acid residue substitutions, deletions or additions in one or more non-human CDRs. The humanized antibody derivative may have substantially the same binding, stronger binding or weaker binding when compared to a non-derivative humanized antibody. In specific embodiments, one, two, three, four, or five amino acid residues of the CDR have been substituted, deleted or added (i.e., mutated). Completely human antibodies are particularly desirable for therapeutic treatment of human subjects.

Human antibodies can be made by a variety of methods known in the art including phage display methods described above using antibody libraries derived from human immunoglobulin sequences (see U.S. Pat. Nos. 4,444,887 and 4,716,111; and International Publication Nos. WO 98/46645, WO 98/50433, WO 98/24893, WO 98/16654, WO 96/34096, WO 96/33735, and WO 91/10741). Human antibodies can be produced using transgenic mice which are incapable of expressing functional endogenous immunoglobulins, but which can express human immunoglobulin genes. For example, the human heavy and light chain immunoglobulin gene complexes may be introduced randomly or by homologous recombination into mouse embryonic stem cells. Alternatively, the human variable region, constant region, and diversity region may be introduced into mouse embryonic stem cells in addition to the human heavy and light chain genes. The mouse heavy and light chain immunoglobulin genes may be rendered non-functional separately or simultaneously with the introduction of human immunoglobulin loci by homologous recombination. In particular, homozygous deletion of the JH region prevents endogenous antibody production. The modified embryonic stem cells are expanded and microinjected into blastocysts to produce chimeric mice. The chimeric mice are then bred to produce homozygous offspring which express human antibodies. The transgenic mice are immunized using conventional methodologies with a selected antigen, e.g., all or a portion of a B7-H5 polypeptide. Monoclonal antibodies directed against the antigen can be obtained from the immunized, transgenic mice using conventional hybridoma technology (see, e.g., U.S. Pat. No. 5,916,771). The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies. For an overview of this technology for producing human antibodies, see Lonberg and Huszar (1995, Int. Rev. Immunol. 13:65-93, which is incorporated herein by reference in its entirety). For a detailed discussion of this technology for producing human antibodies and human monoclonal antibodies and protocols for producing such antibodies, see, e.g., International Publication Nos. WO 98/24893, WO 96/34096, and WO 96/33735; and U.S. Pat. Nos. 5,413,923, 5,625,126, 5,633,425, 5,569,825, 5,661,016, 5,545,806, 5,814,318, and 5,939,598, which are incorporated by reference herein in their entirety. In addition, companies such as Abgenix, Inc. (Freemont, Calif.) and Medarex (Princeton, N.J.) can be engaged to provide human antibodies directed against a selected antigen using technology similar to that described above.

A "chimeric antibody" is a molecule in which different portions of the antibody are derived from different immunoglobulin molecules such as antibodies having a variable region derived from a non-human antibody and a human immunoglobulin constant region. Methods for producing chimeric antibodies are known in the art. See e.g., Morrison, 1985, Science 229:1202; Oi et al., 1986, BioTechniques 4:214; Gillies et al., 1989, J. Immunol. Methods 125:191-202; and U.S. Pat. Nos. 6,311,415, 5,807,715, 4,816,567, and 4,816,397. Chimeric antibodies comprising one or more CDRs from a non-human species and framework regions from a human immunoglobulin molecule can be produced using a variety of techniques known in the art including, for example, CDR-grafting (EP 239,400; International Publication No. WO 91/09967; and U.S. Pat. Nos. 5,225,539, 5,530,101, and 5,585,089), veneering or resurfacing (EP 592,106; EP 519,596; Padlan, 1991, Molecular Immunology 28(4/5):489-498; Studnicka et al., 1994, Protein Engineering 7:805; and Roguska et al., 1994, Proc. Natl. Acad. Sci. USA 91:969), and chain shuffling (U.S. Pat. No. 5,565,332).

The invention particularly concerns "humanized antibodies" (see, e.g., European Patent Nos. EP 239,400, EP 592,106, and EP 519,596; International Publication Nos. WO 91/09967 and WO 93/17105; U.S. Pat. Nos. 5,225,539, 5,530,101, 5,565,332, 5,585,089, 5,766,886, and 6,407,213; and Padlan, 1991, Molecular Immunology 28(4/5):489-498; Studnicka et al., 1994, Protein Engineering 7(6):805-814; Roguska et al., 1994, PNAS 91:969-973; Tan et al., 2002, J. Immunol. 169:1119-1125; Caldas et al., 2000, Protein Eng. 13:353-360; Morea et al., 2000, Methods 20:267-79; Baca et al., 1997, J. Biol. Chem. 272:10678-10684; Roguska et al., 1996, Protein Eng. 9:895-904; Couto et al., 1995, Cancer Res. 55 (23 Supp):5973s-5977s; Couto et al., 1995, Cancer Res. 55:1717-22; Sandhu, 1994, Gene 150:409-10; Pedersen et al., 1994, J. Mol. Biol. 235:959-973; Jones et al., 1986, Nature 321:522-525; Reichmann et al., 1988, Nature 332: 323-329; and Presta, 1992, Curr. Op. Struct. Biol. 2:593-596). As used herein, the term "humanized antibody" refers to an immunoglobulin comprising a human framework region and one or more CDR's from a non-human (usually a mouse or rat) immunoglobulin. The non-human immunoglobulin providing the CDR's is called the "donor" and the human immunoglobulin providing the framework is called the "acceptor." Constant regions need not be present, but if they are, they must be substantially identical to human immunoglobulin constant regions, i.e., at least about 85-90%, preferably about 95% or more identical. Hence, all parts of a humanized immunoglobulin, except possibly the CDR's, are substantially identical to corresponding parts of natural human immunoglobulin sequences. A humanized antibody is an antibody comprising a humanized light chain and a humanized heavy chain immunoglobulin. For example, a humanized antibody would not encompass a typical chimeric antibody, because, e.g., the entire variable region of a chimeric antibody is non-human. One says that the donor antibody has been "humanized," by the process of "humanization," because the resultant humanized antibody is expected to bind to the same antigen as the donor antibody that provides the CDR's. For the most part, humanized antibodies are human immunoglobulins (recipient antibody) in which hypervariable region residues of the recipient are replaced by hypervariable region residues from a non-human species (donor antibody) such as mouse, rat, rabbit or a non-human primate having the desired specificity, affinity, and capacity. In some instances, Framework Region (FR) residues of the human immunoglobulin are replaced by corresponding non-human residues. Furthermore, humanized antibodies may comprise residues which are not found in the recipient antibody or in the donor antibody. These modifications are made to further refine antibody performance. In general, the humanized antibody will comprise substantially all of at least one, and typically two, variable domains, in which all or substantially all of the hypervariable regions correspond to those of a non-human immunoglobulin and all or substantially all of the FRs are those of a human immunoglobulin sequence. The humanized antibody optionally also will comprise at least a portion of an immunoglobulin constant region (Fc), typically that of a human immunoglobulin that immunospecifically binds to an Fc RIIB polypeptide, that has been altered by the introduction of amino acid residue substitutions, deletions or additions (i.e., mutations).

DNA sequences coding for preferred human acceptor framework sequences include but are not limited to FR framework segments from the human germline VH segment VH1-18 and JH6 and the human germline VL segment VK-A26 and JK4. In a specific embodiment, one or more of the CDRs are inserted within framework regions using routine recombinant DNA techniques. The framework regions may be naturally occurring or consensus framework regions, and preferably human framework regions (see, e.g., Chothia et al., 1998, "Structural Determinants In The Sequences Of Immunoglobulin Variable Domain," J. Mol. Biol. 278: 457-479 for a listing of human framework regions).

A humanized or chimeric B7-H5 antibody can include substantially all of at least one, and typically two, variable domains in which all or substantially all of the CDR regions correspond to those of a non-human immunoglobulin (i.e., donor antibody) and all or substantially all of the framework regions are those of a human immunoglobulin consensus sequence. Preferably, a B7-H5 antibody also includes at least a portion of an immunoglobulin constant region (Fc), typically that of a human immunoglobulin. The constant domains of the B7-H5 antibodies may be selected with respect to the proposed function of the antibody, in particular the effector function which may be required. In some embodiments, the constant domains of the B7-H5 antibodies are (or comprise) human IgA, IgD, IgE, IgG or IgM domains. In a specific embodiment, human IgG constant domains, especially of the IgG1 and IgG3 isotypes are used, when the humanized B7-H5 antibodies is intended for therapeutic uses and antibody effector functions such as antibody-dependent cell-mediated cytotoxicity (ADCC) and complement-dependent cytotoxicity (CDC) activity are needed. In alternative embodiments, IgG2 and IgG4 isotypes are used when the B7-H5 antibody is intended for therapeutic purposes and antibody effector function is not required. The invention encompasses Fc constant domains comprising one or more amino acid modifications which alter antibody effector functions such as those disclosed in U.S. Patent Application Publication Nos. 2005/0037000 and 2005/0064514.

In some embodiments, the B7-H5 antibody contains both the light chain as well as at least the variable domain of a heavy chain. In other embodiments, the B7-H5 antibody may further include one or more of the CH1, hinge, CH2, CH3, and CH4 regions of the heavy chain. The antibody can be selected from any class of immunoglobulins, including IgM, IgG, IgD, IgA and IgE, and any isotype, including IgG1, IgG2, IgG3 and IgG4. In some embodiments, the constant domain is a complement fixing constant domain where it is desired that the antibody exhibit cytotoxic activity, and the class is typically IgG1. In other embodiments, where such cytotoxic activity is not desirable, the constant domain may be of the IgG2 class. The B7-H5 antibody may comprise sequences from more than one class or isotype, and selecting particular constant domains to optimize desired effector functions is within the ordinary skill in the art.

The framework and CDR regions of a humanized antibody need not correspond precisely to the parental sequences, e.g., the donor CDR or the consensus framework may be mutagenized by substitution, insertion or deletion of at least one residue so that the CDR or framework residue at that site does not correspond to either the consensus or the donor antibody. Such mutations, however, are preferably not extensive. Usually, at least 75% of the humanized antibody residues will correspond to those of the parental framework region (FR) and CDR sequences, more often 90%, and most preferably greater than 95%. Humanized antibodies can be produced using variety of techniques known in the art, including, but not limited to, CDR-grafting (European Patent No. EP 239,400; International Publication No. WO 91/09967; and U.S. Pat. Nos. 5,225,539, 5,530,101, and 5,585,089), veneering or resurfacing (European Patent Nos. EP 592,106 and EP 519,596; Padlan, 1991, Molecular Immunology 28(4/5):489-498; Studnicka et al., 1994, Protein Engineering 7(6):805-814; and Roguska et al., 1994, Proc. Natl. Acad. Sci. 91:969-973), chain shuffling (U.S. Pat. No. 5,565,332), and techniques disclosed in, e.g., U.S. Pat. Nos. 6,407,213, 5,766,886, 5,585,089, International Publication No. WO 9317105, Tan et al., 2002, J. Immunol. 169:1119-25, Caldas et al., 2000, Protein Eng. 13:353-60, Morea et al., 2000, Methods 20:267-79, Baca et al., 1997, J. Biol. Chem. 272:10678-84, Roguska et al., 1996, Protein Eng. 9:895-904, Couto et al., 1995, Cancer Res. 55 (23 Supp):5973s-5977s, Couto et al., 1995, Cancer Res. 55:1717-22, Sandhu, 1994, Gene 150:409-10, Pedersen et al., 1994, J. Mol. Biol. 235:959-73, Jones et al., 1986, Nature 321:522-525, Riechmann et al., 1988, Nature 332:323, and Presta, 1992, Curr. Op. Struct. Biol. 2:593-596. Often, framework residues in the framework regions will be substituted with the corresponding residue from the CDR donor antibody to alter, preferably improve, antigen binding. These framework substitutions are identified by methods well known in the art, e.g., by modeling of the interactions of the CDR and framework residues to identify framework residues important for antigen binding and sequence comparison to identify unusual framework residues at particular positions. (See, e.g., Queen et al., U.S. Pat. No. 5,585,089; U.S. Publication Nos. 2004/0049014 and 2003/0229208; U.S. Pat. Nos. 6,350,861; 6,180,370; 5,693,762; 5,693,761; 5,585,089; and 5,530,101 and Riechmann et al., 1988, Nature 332:323).

The antibodies used in the methods of the present invention may be monospecific. Also of interest are bispecific antibodies, trispecific antibodies or antibodies of greater multispecificity that exhibit specificity to different targets in addition to B7-H5, such as other molecules of the immune system. For example, such antibodies may bind to both B7-H5 and to an antigen that is important for targeting the antibody to a particular cell type or tissue (for example, to an antigen associated with a cancer antigen of a tumor being treated). In another embodiment, such multispecific antibody binds to molecules (receptors or ligands) involved in alternative or supplemental immunomodulatory pathways, such as CTLA4, TIM3, TIM4, OX40, CD40, GITR, 4-1-BB, CD27/CD70, ICOS, B7-H4, LIGHT, PD-1 or LAG3, in order to diminish further modulate the immunomodulatory effects. Furthermore, the multispecific antibody may bind to effector molecules such as cytokines (e.g., IL-7, IL-15, IL-12, IL-4 TGF-beta, IL-10, IL-17, IFNg, Flt3, BLys) and chemokines (e.g., CCL21), which may be particularly relevant for down-modulating both acute and chronic immune responses.

The antibodies of the present invention may be produced by any method known in the art useful for the production of polypeptides, e.g., in vitro synthesis, recombinant DNA production, and the like. Preferably, the antibodies are produced by recombinant DNA technology. The B7-H5 antibodies may be produced using recombinant immunoglobulin expression technology. The recombinant production of immunoglobulin molecules, including humanized antibodies are described in U.S. Pat. No. 4,816,397 (Boss et al.), U.S. Pat. Nos. 6,331,415 and 4,816,567 (both to Cabilly et al.), U.K. patent GB 2,188,638 (Winter et al.), and U.K. patent GB 2,209,757. Techniques for the recombinant expression of immunoglobulins, including humanized immunoglobulins, can also be found, in Goeddel et al., Gene Expression Technology Methods in Enzymology Vol. 185 Academic Press (1991), and Borreback, Antibody Engineering, W. H. Freeman (1992). Additional information concerning the generation, design and expression of recombinant antibodies can be found in Mayforth, Designing Antibodies, Academic Press, San Diego (1993).

An exemplary process for the production of the recombinant chimeric B7-H5 antibodies can include the following: a) constructing, by conventional molecular biology methods, an expression vector that encodes and expresses an antibody heavy chain in which the CDRs and variable region of a murine anti-human B7-H5 monoclonal antibody are fused to an Fc region derived from a human immunoglobulin, thereby producing a vector for the expression of a chimeric antibody heavy chain; b) constructing, by conventional molecular biology methods, an expression vector that encodes and expresses an antibody light chain of the murine anti-human B7-H5 monoclonal antibody, thereby producing a vector for the expression of chimeric antibody light chain; c) transferring the expression vectors to a host cell by conventional molecular biology methods to produce a transfected host cell for the expression of chimeric antibodies; and d) culturing the transfected cell by conventional cell culture techniques so as to produce chimeric antibodies.

An exemplary process for the production of the recombinant humanized B7-H5 antibodies can include the following: a) constructing, by conventional molecular biology methods, an expression vector that encodes and expresses an anti-human B7-H5 heavy chain in which the CDRs and a minimal portion of the variable region framework that are required to retain donor antibody binding specificity are derived from a non-human immunoglobulin, such as a murine anti-human B7-H5 monoclonal antibody, and the remainder of the antibody is derived from a human immunoglobulin, thereby producing a vector for the expression of a humanized antibody heavy chain; b) constructing, by conventional molecular biology methods, an expression vector that encodes and expresses an antibody light chain in which the CDRs and a minimal portion of the variable region framework that are required to retain donor antibody binding specificity are derived from a non-human immunoglobulin, such as a murine anti-human B7-H5 monoclonal antibody, and the remainder of the antibody is derived from a human immunoglobulin, thereby producing a vector for the expression of humanized antibody light chain; c) transferring the expression vectors to a host cell by conventional molecular biology methods to produce a transfected host cell for the expression of humanized antibodies; and d) culturing the transfected cell by conventional cell culture techniques so as to produce humanized antibodies.

With respect to either exemplary method, host cells may be co-transfected with such expression vectors, which may contain different selectable markers but, with the exception of the heavy and light chain coding sequences, are preferably identical. This procedure provides for equal expression of heavy and light chain polypeptides. Alternatively, a single vector may be used which encodes both heavy and light chain polypeptides. The coding sequences for the heavy and light chains may comprise cDNA or genomic DNA or both. The host cell used to express the recombinant B7-H5 antibody can be either a bacterial cell such as *Escherichia coli*, or more preferably a eukaryotic cell (e.g., a Chinese hamster ovary (CHO) cell or a HEK-293 cell). The choice of expression vector is dependent upon the choice of host cell, and may be selected so as to have the desired expression and regulatory characteristics in the selected host cell. Other cell lines that may be used include, but are not limited to, CHO-K1, NSO, and PER.C6 (Crucell, Leiden, Netherlands).

Any of the above-described antibodies can be used to generate antiidiotype antibodies using techniques well known to those skilled in the art (see, e.g., Greenspan, N. S. et al. (1989) "*Idiotypes: Structure And Immunogenicity,*" FASEB J. 7:437-444; and Nisinoff, A. (1991) "*Idiotypes: Concepts And Applications,*" J. Immunol. 147(8):2429-2438).

The binding properties of any of the above antibodies can, if desired, be further improved by screening for variants that exhibit such desired characteristics. For example, such antibodies can be generated using various phage display methods known in the art. In phage display methods, functional antibody domains are displayed on the surface of phage particles which carry the polynucleotide sequences encoding them. In a particular embodiment, such phage can be utilized to display antigen binding domains, such as Fab and Fv or disulfide-bond stabilized Fv, expressed from a repertoire or combinatorial antibody library (e.g., human or murine). Phage expressing an antigen binding domain that binds the antigen of interest can be selected or identified with antigen, e.g., using labeled antigen or antigen bound or captured to a solid surface or bead. Phage used in these methods are typically filamentous phage, including fd and M13. The antigen binding domains are expressed as a recombinantly fused protein to either the phage gene III or gene VIII protein. Examples of phage display methods that can be used to make the immunoglobulins, or fragments thereof, of the present invention include those disclosed in Brinkman, U. et al. (1995) "*Phage Display Of Disulfide-Stabilized Fv Fragments,*" J. Immunol. Methods, 182:41-50, 1995; Ames, R. S. et al. (1995) "*Conversion Of Murine Fabs Isolated From A Combinatorial Phage Display Library To Full Length Immunoglobulins,*" J. Immunol. Methods, 184:177-186; Kettleborough, C. A. et al. (1994) "*Isolation Of Tumor Cell-Specific Single-Chain Fv From Immunized Mice Using Phage-Antibody Libraries And The Re-Construction Of Whole Antibodies From These Antibody Fragments,*" Eur. J. Immunol., 24:952-958, 1994; Persic, L. et al. (1997) "*An Integrated Vector System For The Eukaryotic Expression Of Antibodies Or Their Fragments After Selection From Phage Display Libraries,*" Gene, 187:9-18; Burton, D. R. et al. (1994) "*Human Antibodies From Combinatorial Libraries,*" Adv. Immunol. 57:191-280; PCT Publications WO 92/001047; WO 90/02809; WO 91/10737; WO 92/01047; WO 92/18619; WO 93/11236; WO 95/15982; WO 95/20401; and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743 and 5,969,108.

As described in the above references, after phage selection, the antibody coding regions from the phage can be isolated and used to generate whole antibodies, including humanized antibodies, or any other desired fragments, and expressed in any desired host, including mammalian cells, insect cells, plant cells, yeast, and bacteria, e.g., as described in detail below. For example, techniques to recombinantly produce Fab, Fab' and F(ab')2 fragments can also be employed using methods known in the art (such as those disclosed in PCT Publication WO 92/22324; Mullinax, R. L.

et al. (1992) "*Expression Of A Heterodimeric Fab Antibody Protein In One Cloning Step,*" *BioTechniques,* 12(6):864-869; and Sawai et al. (1995) "*Direct Production Of The Fab Fragment Derived From The Sperm Immobilizing Antibody Using Polymerase Chain Reaction And cDNA Expression Vectors,*" *Am. J. Reprod. Immunol.* 34:26-34; and Better, M. et al. (1988) "*Escherichia coli Secretion Of An Active Chimeric Antibody Fragment,*" *Science* 240:1041-1043). Examples of techniques which can be used to produce single-chain Fvs and antibodies include those described in U.S. Pat. Nos. 4,946,778 and 5,258,498; Huston, J. S. et al. (1991) "*Protein Engineering Of Single-Chain Fv Analogs And Fusion Proteins,*" *Methods in Enzymology* 203:46-88; Shu, L. et al., "*Secretion Of A Single-Gene-Encoded Immunoglobulin From Myeloma Cells,*" *Proc. Natl. Acad. Sci.* (USA) 90:7995-7999; and Skerra. A. et al. (1988) "*Assembly Of A Functional Immunoglobulin Fv Fragment In Escherichia coli,*" *Science* 240:1038-1040.

Phage display technology can be used to increase the affinity of an antibody for B7-H5. This technique would be useful in obtaining high affinity antibodies that could be used in the disclosed combinatorial methods. This technology, referred to as affinity maturation, employs mutagenesis or CDR walking and re-selection using such receptors or ligands (or their extracellular domains) or an antigenic fragment thereof to identify antibodies that bind with higher affinity to the antigen when compared with the initial or parental antibody (See, e.g., Glaser, S. M. et al. (1992) "*Antibody Engineering By Codon-Based Mutagenesis In A Filamentous Phage Vector System,*" *J. Immunol.* 149:3903-3913). Mutagenizing entire codons rather than single nucleotides results in a semi-randomized repertoire of amino acid mutations. Libraries can be constructed consisting of a pool of variant clones each of which differs by a single amino acid alteration in a single CDR and which contain variants representing each possible amino acid substitution for each CDR residue. Mutants with increased binding affinity for the antigen can be screened by contacting the immobilized mutants with labeled antigen. Any screening method known in the art can be used to identify mutant antibodies with increased avidity to the antigen (e.g., ELISA) (see, e.g., Wu, H. et al. (1998) "*Stepwise In Vitro Affinity Maturation Of Vitaxin, An Alphav Beta3-Specific Humanized Mab,*" *Proc. Natl. Acad. Sci.* (USA) 95(11): 6037-6042; Yelton, D. E. et al. (1995) "*Affinity Maturation Of The BR96 Anti-Carcinoma Antibody By Codon-Based Mutagenesis,*" *J. Immunol.* 155:1994-2004). CDR walking which randomizes the light chain may be used possible (see, Schier et al. (1996) "*Isolation Of Picomolar Affinity Anti-C-Erbb-2 Single-Chain Fv By Molecular Evolution Of The Complementarity Determining Regions In The Center Of The Antibody Binding Site,*" *J. Mol. Biol.* 263:551-567).

The invention thus contemplates the use of random mutagenesis to identify improved CDRs. Phage display technology can alternatively be used to increase (or decrease) CDR affinity. This technology, referred to as affinity maturation, employs mutagenesis or "CDR walking" and re-selection uses the target antigen or an antigenic fragment thereof to identify antibodies having CDRs that bind with higher (or lower) affinity to the antigen when compared with the initial or parental antibody (see, e.g., Glaser, S. M. et al. (1992) "*Antibody Engineering By Codon-Based Mutagenesis In A Filamentous Phage Vector System,*" *J. Immunol.* 149:3903-3913). Mutagenizing entire codons rather than single nucleotides results in a semi-randomized repertoire of amino acid mutations. Libraries can be constructed consisting of a pool of variant clones each of which differs by a single amino acid alteration in a single CDR and which contain variants representing each possible amino acid substitution for each CDR residue. Mutants with increased (or decreased) binding affinity for the antigen can be screened by contacting the immobilized mutants with labeled antigen. Any screening method known in the art can be used to identify mutant antibodies with increased (or decreased) avidity to the antigen (e.g., ELISA) (see, Wu, H. et al. (1998) "*Stepwise In Vitro Affinity Maturation Of Vitaxin, An Alphav Beta3-Specific Humanized Mab,*" *Proc. Natl. Acad. Sci.* (USA) 95(11):6037-6042; Yelton, D. E. et al. (1995) "*Affinity Maturation Of The BR96 Anti-Carcinoma Antibody By Codon-Based Mutagenesis,*" *J. Immunol.* 155:1994-2004). CDR walking which randomizes the light chain may be used possible (see, Schier et al. (1996) "*Isolation Of Picomolar Affinity Anti-C-Erbb-2 Single-Chain Fv By Molecular Evolution Of The Complementarity Determining Regions In The Center Of The Antibody Binding Site,*" *J. Mol. Biol.* 263: 551-567).

Methods for accomplishing such affinity maturation are described for example in: Krause, J. C. et al. (2011) "*An Insertion Mutation That Distorts Antibody Binding Site Architecture Enhances Function Of A Human Antibody,*" MBio. 2(1) pii: e00345-10. doi: 10.1128/mBio.00345-10; Kuan, C. T. et al. (2010) "*Affinity-Matured Anti-Glycoprotein NMB Recombinant Immunotoxins Targeting Malignant Gliomas And Melanomas,*" *Int. J. Cancer* 10.1002/ijc.25645; Hackel, B. J. et al. (2010) "*Stability And CDR Composition Biases Enrich Binder Functionality Landscapes,*" *J. Mol. Biol.* 401(1):84-96; Montgomery, D. L. et al. (2009) "*Affinity Maturation And Characterization Of A Human Monoclonal Antibody Against HIV-1 gp41,*" *MAbs* 1(5):462-474; Gustchina, E. et al. (2009) "*Affinity Maturation By Targeted Diversification Of The CDR-H2 Loop Of A Monoclonal Fab Derived From A Synthetic Naïve Human Antibody Library And Directed Against The Internal Trimeric Coiled-Coil Of Gp41 Yields A Set Of Fabs With Improved HIV-1 Neutralization Potency And Breadth,*" *Virology* 393(1):112-119; Finlay, W. J. et al. (2009) "*Affinity Maturation Of A Humanized Rat Antibody For Anti-RAGE Therapy: Comprehensive Mutagenesis Reveals A High Level Of Mutational Plasticity Both Inside And Outside The Complementarity-Determining Regions,*" *J. Mol. Biol.* 388(3):541-558; Bostrom, J. et al. (2009) "*Improving Antibody Binding Affinity And Specificity For Therapeutic Development,*" *Methods Mol. Biol.* 525: 353-376; Steidl, S. et al. (2008) "*In Vitro Affinity Maturation Of Human GM-CSF Antibodies By Targeted CDR-Diversification,*" *Mol. Immunol.* 46(1):135-144; and Barderas, R. et al. (2008) "Affinity maturation of antibodies assisted by in silico modeling," *Proc. Natl. Acad. Sci.* (USA) 105(26): 9029-9034.

The invention particularly contemplates the production and use of "derivatives" of any of the above-described antibodies and their antigen-binding fragments.

The term "derivative" refers to an antibody or antigen-binding fragment thereof that immunospecifically binds to an antigen but which comprises, one, two, three, four, five or more amino acid substitutions, additions, deletions or modifications relative to a "parental" (or wild-type) molecule. Such amino acid substitutions or additions may introduce naturally occurring (i.e., DNA-encoded) or non-naturally occurring amino acid residues. The term "derivative" encompasses, for example, chimeric or humanized variants of any of antibodies 1.3, 4.5 or 7.8, as well as variants having altered CH1, hinge, CH2, CH3 or CH4 regions, so as to form, for example antibodies, etc., having variant Fc regions that exhibit enhanced or impaired effector or binding characteristics. The term "derivative" additionally encompasses non-amino acid modifications, for example, amino acids that may be glycosylated (e.g., have altered mannose, 2-N-acetylglucosamine, galactose, fucose, glucose, sialic acid, 5-N-acetylneuraminic acid, 5-glycolneuraminic acid, etc. content), acetylated, pegylated, phosphorylated, amidated, derivatized by known protecting/blocking groups, proteolytic cleavage, linked to a cellular ligand or other protein, etc. In some embodiments, the altered carbohydrate modifications modulate one or more of the following: solubilization of the antibody, facilitation of subcellular transport and secretion of the antibody, promotion of antibody assembly, conformational integrity, and antibody-mediated effector function. In a specific embodiment the altered carbohydrate modifications enhance antibody mediated effector function relative to the antibody lacking the carbohydrate modification. Carbohydrate modifications that lead to altered antibody mediated effector function are well known in the art (for example, see Shields, R. L. et al. (2002) "*Lack Of Fucose On Human IgG N-Linked Oligosaccharide Improves Binding To Human Fcgamma RIII And Antibody-Dependent Cellular Toxicity*," J. Biol. Chem. 277(30): 26733-26740; Davies J. et al. (2001) "*Expression Of GnTIII In A Recombinant Anti-CD20 CHO Production Cell Line: Expression Of Antibodies With Altered Glycoforms Leads To An Increase In ADCC Through Higher Affinity For FC Gamma RIII*," Biotechnology & Bioengineering 74(4): 288-294). Methods of altering carbohydrate contents are known to those skilled in the art, see, e.g., Wallick, S. C. et al. (1988) "*Glycosylation Of A VH Residue Of A Monoclonal Antibody Against Alpha (1----6) Dextran Increases Its Affinity For Antigen*," J. Exp. Med. 168(3): 1099-1109; Tao, M. H. et al. (1989) "*Studies Of Aglycosylated Chimeric Mouse-Human IgG. Role Of Carbohydrate In The Structure And Effector Functions Mediated By The Human IgG Constant Region*," J. Immunol. 143(8): 2595-2601; Routledge, E. G. et al. (1995) "*The Effect Of Aglycosylation On The Immunogenicity Of A Humanized Therapeutic CD3 Monoclonal Antibody*," Transplantation 60(8):847-53; Elliott, S. et al. (2003) "*Enhancement Of Therapeutic Protein In Vivo Activities Through Glycoengineering*," Nature Biotechnol. 21:414-21; Shields, R. L. et al. (2002) "*Lack Of Fucose On Human IgG N-Linked Oligosaccharide Improves Binding To Human Fcgamma RIII And Antibody-Dependent Cellular Toxicity*," J. Biol. Chem. 277(30): 26733-26740).

In some embodiments, a humanized antibody is a derivative. Such a humanized antibody comprises amino acid residue substitutions, deletions or additions in one or more non-human CDRs. The humanized antibody derivative may have substantially the same binding, better binding, or worse binding when compared to a non-derivative humanized antibody. In specific embodiments, one, two, three, four, or five amino acid residues of the CDR have been substituted, deleted or added (i.e., mutated).

A derivative antibody or antibody fragment may be modified by chemical modifications using techniques known to those of skill in the art, including, but not limited to, specific chemical cleavage, acetylation, formulation, metabolic synthesis of tunicamycin, etc. In one embodiment, an antibody derivative will possess a similar or identical function as the parental antibody. In another embodiment, an antibody derivative will exhibit an altered activity relative to the parental antibody. For example, a derivative antibody (or fragment thereof) can bind to its epitope more tightly or be more resistant to proteolysis than the parental antibody.

Derivatized antibodies may be used to alter the half-lives (e.g., serum half-lives) of parental antibodies in a mammal, preferably a human. Preferably such alteration will result in a half-life of greater than 15 days, preferably greater than 20 days, greater than 25 days, greater than 30 days, greater than 35 days, greater than 40 days, greater than 45 days, greater than 2 months, greater than 3 months, greater than 4 months, or greater than 5 months. The increased half-lives of the humanized antibodies of the present invention or fragments thereof in a mammal, preferably a human, results in a higher serum titer of said antibodies or antibody fragments in the mammal, and thus, reduces the frequency of the administration of said antibodies or antibody fragments and/or reduces the concentration of said antibodies or antibody fragments to be administered. Antibodies or fragments thereof having increased in vivo half-lives can be generated by techniques known to those of skill in the art. For example, antibodies or fragments thereof with increased in vivo half-lives can be generated by modifying (e.g., substituting, deleting or adding) amino acid residues identified as involved in the interaction between the Fc domain and the FcRn receptor. The humanized B7-H5 antibodies can be engineered to increase biological half-lives (see, e.g. U.S. Pat. No. 6,277,375). For example, humanized B7-H5 antibodies can be engineered in the Fc-hinge domain to have increased in vivo or serum half-lives.

Antibodies or fragments thereof with increased in vivo half-lives can be generated by attaching to said antibodies or antibody fragments polymer molecules such as high molecular weight polyethyleneglycol (PEG). PEG can be attached to said antibodies or antibody fragments with or without a multifunctional linker either through site-specific conjugation of the PEG to the N- or C-terminus of said antibodies or antibody fragments or via epsilon-amino groups present on lysine residues. Linear or branched polymer derivatization that results in minimal loss of biological activity will be used. The degree of conjugation will be closely monitored by SDS-PAGE and mass spectrometry to ensure proper conjugation of PEG molecules to the antibodies. Unreacted PEG can be separated from antibody-PEG conjugates by, e.g., size exclusion or ion-exchange chromatography.

The B7-H5 antibodies may also be modified by the methods and coupling agents described by Davis et al. (See U.S. Pat. No. 4,179,337) in order to provide compositions that can be injected into the mammalian circulatory system with substantially no immunogenic response.

One embodiment encompasses modification of framework residues of the humanized B7-H5 antibodies. Framework residues in the framework regions may be substituted with the corresponding residue from the CDR donor antibody to alter, preferably improve, antigen binding. These framework substitutions are identified by methods well known in the art, e.g., by modeling of the interactions of the CDR and framework residues to identify framework residues important for antigen binding and sequence comparison to identify unusual framework residues at particular positions. (See, e.g., U.S. Pat. No. 5,585,089; and Riechmann, L. et al. (1988) "*Reshaping Human Antibodies For Therapy*," Nature 332:323-327).

Yet another embodiment encompasses anti-human B7-H5 antibodies (and more preferably, humanized antibodies) and antigen-binding fragments thereof that are recombinantly fused or chemically conjugated (including both covalently and non-covalently conjugations) to a heterologous molecule (i.e., an unrelated molecule). The fusion does not necessarily need to be direct, but may occur through linker sequences.

In one embodiment such heterologous molecules are polypeptides having at least 10, at least 20, at least 30, at least 40, at least 50, at least 60, at least 70, at least 80, at least 90 or at least 100 amino acids. Such heterologous molecules may alternatively be enzymes, hormones, cell surface receptors, drug moieties, such as: toxins (such as abrin, ricin A, pseudomonas exotoxin (i.e., PE-40), diphtheria toxin, ricin, gelonin, or pokeweed antiviral protein), proteins (such as tumor necrosis factor, interferon (e.g., α-interferon, β-interferon), nerve growth factor, platelet derived growth factor, tissue plasminogen activator, or an apoptotic agent (e.g., tumor necrosis factor-α, tumor necrosis factor-β)), biological response modifiers (such as, for example, a lymphokine (e.g., interleukin-1 ("IL-1"), interleukin-2 ("IL-2"), interleukin-6 ("IL-6")), granulocyte macrophage colony stimulating factor ("GM-CSF"), granulocyte colony stimulating factor ("G-CSF"), or macrophage colony stimulating factor, ("M-CSF")), or growth factors (e.g., growth hormone ("GH"))), cytotoxins (e.g., a cytostatic or cytocidal agent, such as paclitaxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof), antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, BiCNU® (carmustine; BSNU) and lomustine (CCNU), cyclothosphamide, busulfan, dibromomannitol, streptozotocin, mitomycin C, and cisdichlorodiamine platinum (II) (DDP) cisplatin, anthracyclines (e.g., daunorubicin (formerly daunomycin) and doxorubicin), antibiotics (e.g., dactinomycin (formerly actinomycin), bleomycin, mithramycin, and anthramycin (AMC)), or anti-mitotic agents (e.g., vincristine and vinblastine).

Techniques for conjugating such therapeutic moieties to antibodies are well known; see, e.g., Arnon et al., "*Monoclonal Antibodies For Immunotargeting Of Drugs In Cancer Therapy*", in MONOCLONAL ANTIBODIES AND CANCER THERAPY, Reisfeld et al. (eds.), 1985, pp. 243-56, Alan R. Liss, Inc.); Hellstrom et al., "*Antibodies For Drug Delivery*", in CONTROLLED DRUG DELIVERY (2nd Ed.), Robinson et al. (eds.), 1987, pp. 623-53, Marcel Dekker, Inc.); Thorpe, "*Antibody Carriers Of Cytotoxic Agents In Cancer Therapy: A Review*", in MONOCLONAL ANTIBODIES '84: BIOLOGICAL AND CLINICAL APPLICATIONS, Pinchera et al. (eds.), 1985, pp. 475-506); "*Analysis, Results, And Future Prospective Of The Therapeutic Use Of Radiolabeled Antibody In Cancer Therapy*", in MONOCLONAL ANTIBODIES FOR CANCER DETECTION AND THERAPY, Baldwin et al. (eds.), 1985, pp. 303-16, Academic Press; and Thorpe et al. (1982) "*The Preparation And Cytotoxic Properties Of Antibody-Toxin Conjugates*," Immunol. Rev. 62:119-158.

In one embodiment, the B7-H5 antibodies or B7-H5 fusion molecules include an Fc portion. The Fc portion of such molecules may be varied by isotype or subclass, may be a chimeric or hybrid, and/or may be modified, for example to improve effector functions, control of half-life, tissue accessibility, augment biophysical characteristics such as stability, and improve efficiency of production (and less costly). Many modifications useful in construction of disclosed fusion proteins and methods for making them are known in the art, see for example Mueller, J. P. et al. (1997) "*Humanized Porcine VCAM-Specific Monoclonal Antibodies With Chimeric IgG2/G4 Constant Regions Block Human Leukocyte Binding To Porcine Endothelial Cells*," Mol. Immun 34(6):441-452, Swann, P. G. (2008) "*Considerations For The Development Of Therapeutic Monoclonal Antibodies*," Curr. Opin. Immun. 20:493-499 (2008), and Presta, L. G. (2008) "*Molecular Engineering And Design Of Therapeutic Antibodies*," Curr. Opin. Immun 20:460-470. In some embodiments the Fc region is the native IgG1, IgG2, or IgG4 Fc region. In some embodiments the Fc region is a hybrid, for example a chimeric consisting of IgG2/IgG4 Fc constant regions. Modifications to the Fc region include, but are not limited to, IgG4 modified to prevent binding to Fc gamma receptors and complement, IgG1 modified to improve binding to one or more Fc gamma receptors, IgG1 modified to minimize effector function (amino acid changes), IgG1 with altered/no glycan (typically by changing expression host), and IgG1 with altered pH-dependent binding to FcRn, and IgG4 with serine at amino acid resident #228 in the hinge region changed to proline (S228P) to enhance stability. The Fc region may include the entire hinge region, or less than the entire hinge region.

The therapeutic outcome in patients treated with rituximab (a chimeric mouse/human IgG1 monoclonal antibody against CD20) for non-Hodgkin's lymphoma or Waldenstrom's macroglobulinemia correlated with the individual's expression of allelic variants of Fcγ receptors with distinct intrinsic affinities for the Fc domain of human IgG1. In particular, patients with high affinity alleles of the low affinity activating Fc receptor CD16A (FcγRIIIA) showed higher response rates and, in the cases of non-Hodgkin's lymphoma, improved progression-free survival. In another embodiment, the Fc domain may contain one or more amino acid insertions, deletions or substitutions that reduce binding to the low affinity inhibitory Fc receptor CD32B (FcγRIIB) and retain wild-type levels of binding to or enhance binding to the low affinity activating Fc receptor CD16A (FcγRIIIA).

Another embodiment includes $IgG_{2-4}$ hybrids and $IgG4$ mutants that have reduce binding to FcR which increase their half-life. Representative $IG_{2-4}$ hybrids and IgG4 mutants are described in Angal, S. et al. (1993) "*A Single Amino Acid Substitution Abolishes The Heterogeneity Of Chimeric Mouse/Human (Igg4) Antibody*," Molec. Immunol. 30(1):105-108; Mueller, J. P. et al. (1997) "*Humanized Porcine VCAM-Specific Monoclonal Antibodies With Chimeric Igg2/G4 Constant Regions Block Human Leukocyte Binding To Porcine Endothelial Cells*," Mol. Immun 34(6): 441-452; and U.S. Pat. No. 6,982,323. In some embodiments the $IgG_1$ and/or $IgG_2$ domain is deleted for example, Angal, s. et al. describe $IgG_1$ and $IgG_2$ having serine 241 replaced with a proline.

Substitutions, additions or deletions in the derivatized antibodies may be in the Fc region of the antibody and may thereby serve to modify the binding affinity of the antibody to one or more Fc R. Methods for modifying antibodies with modified binding to one or more Fc R are known in the art, see, e.g., PCT Publication Nos. WO 04/029207, WO 04/029092, WO 04/028564, WO 99/58572, WO 99/51642, WO 98/23289, WO 89/07142, WO 88/07089, and U.S. Pat. Nos. 5,843,597 and 5,642,821. In one particular embodiment, the modification of the Fc region results in an antibody with an altered antibody-mediated effector function, an altered binding to other Fc receptors (e.g., Fc activation receptors), an altered antibody-dependent cell-mediated cytotoxicity (ADCC) activity, an altered C1 q binding activity, an altered complement-dependent cytotoxicity activity (CDC), a phagocytic activity, or any combination thereof.

In some embodiments, the invention encompasses antibodies whose Fc region will have been modified so that the molecule will exhibit altered Fc receptor (FcR) binding activity, for example to exhibit decreased activity toward activating receptors such as FcγRIIA or FcγRIIIA, or increased activity toward inhibitory receptors such as FcγRIIB. Preferably, such antibodies will exhibit decreased antibody-dependent cell-mediated cytotoxicity (ADCC) or complement dependent cytotoxicity (CDC) activities (relative to a wild-type Fc receptor).

Modifications that affect Fc-mediated effector function are well known in the art (see U.S. Pat. No. 6,194,551, and WO 00/42072; Stavenhagen, J. B. et al. (2007) "*Fc Optimization Of Therapeutic Antibodies Enhances Their Ability To Kill Tumor Cells In Vitro And Controls Tumor Expansion In Vivo Via Low-Affinity Activating Fcgamma Receptors*," Cancer Res. 57(18):8882-8890; Shields, R. L. et al. (2001) "*High Resolution Mapping of the Binding Site on Human IgG1 for FcγRI, FcγRII, FcγRIII, and FcRn and Design of IgG1 Variants with Improved Binding to the FcγR*," J. Biol. Chem. 276(9):6591-6604). Exemplary variants of human IgG1 Fc domains with reduced binding to FcγRIIA or FcγRIIIA, but unchanged or enhanced binding to FcγRIIB, include S239A, H268A, S267G, E269A, E293A, E293D, Y296F, R301A, V303A, A327G, K322A, E333A, K334A, K338A, A339A, D376A.

In some embodiments, the invention encompasses antibodies whose Fc region will have been deleted (for example, an Fab or F(ab)$_2$, etc.).

Any of the molecules of the present invention can be fused to marker sequences, such as a peptide, to facilitate purification. In preferred embodiments, the marker amino acid sequence is a hexa-histidine peptide, the hemagglutinin "HA" tag, which corresponds to an epitope derived from the influenza hemagglutinin protein (Wilson, I. A. et al. (1984) "*The Structure Of An Antigenic Determinant In A Protein*," Cell, 37:767-778) and the "flag" tag (Knappik, A. et al. (1994) "*An Improved Affinity Tag Based On The FLAG Peptide For The Detection And Purification Of Recombinant Antibody Fragments*," Biotechniques 17(4):754-761).

The present invention also encompasses antibodies or their antigen-binding fragments that are conjugated to a diagnostic or therapeutic agent or any other molecule for which serum half-life is desired to be increased. The antibodies can be used diagnostically (in vivo, in situ or in vitro) to, for example, monitor the development or progression of a disease, disorder or infection as part of a clinical testing procedure to, e.g., determine the efficacy of a given treatment regimen. Detection can be facilitated by coupling the antibody to a detectable substance. Examples of detectable substances include various enzymes, prosthetic groups, fluorescent materials, luminescent materials, bioluminescent materials, radioactive materials, positron emitting metals, and nonradioactive paramagnetic metal ions. The detectable substance may be coupled or conjugated either directly to the antibody or indirectly, through an intermediate (such as, for example, a linker known in the art) using techniques known in the art. See, for example, U.S. Pat. No. 4,741,900 for metal ions which can be conjugated to antibodies for use as diagnostics according to the present invention. Such diagnosis and detection can be accomplished by coupling the antibody to detectable substances including, but not limited to, various enzymes, enzymes including, but not limited to, horseradish peroxidase, alkaline phosphatase, beta-galactosidase, or acetylcholinesterase; prosthetic group complexes such as, but not limited to, streptavidin/biotin and avidin/biotin; fluorescent materials such as, but not limited to, umbelliferone, fluorescein, fluorescein isothiocyanate, rhodamine, dichlorotriazinylamine fluorescein, dansyl chloride or phycoerythrin; luminescent material such as, but not limited to, luminol; bioluminescent materials such as, but not limited to, luciferase, luciferin, and aequorin; radioactive material such as, but not limited to, bismuth ($^{213}$Bi), carbon ($^{14}$C), chromium ($^{51}$Cr), cobalt ($^{57}$Co), fluorine ($^{18}$F), gadolinium ($^{153}$Gd, $^{159}$Gd), gallium ($^{68}$Ga, $^{67}$Ga), germanium ($^{68}$Ge), holmium ($^{166}$Ho), indium ($^{115}$In, $^{113}$In, $^{112}$In, $^{111}$In), iodine ($^{131}$I, $^{125}$I, $^{123}$I, $^{121}$I), lanthanium ($^{140}$La), lutetium ($^{177}$Lu), manganese ($^{54}$Mn), molybdenum ($^{99}$Mo), palladium ($^{103}$Pd), phosphorous ($^{32}$P), praseodymium ($^{142}$Pr), promethium, ($^{149}$Pm), rhenium ($^{186}$Re, $^{188}$Re), rhodium ($^{105}$Rh), ruthemium ($^{97}$Ru), samarium ($^{153}$Sm), scandium ($^{47}$Sc), selenium ($^{75}$Se), strontium ($^{85}$Sr), sulfur ($^{35}$S), technetium ($^{99}$Tc), thallium ($^{201}$Ti), tin ($^{113}$Sn, $^{117}$Sn), tritium ($^{3}$H), xenon ($^{133}$Xe), ytterbium ($^{169}$YB, $^{175}$Yb) yttrium ($^{90}$Y), zinc ($^{65}$Zn); positron emitting metals using various positron emission tomographies, and nonradioactive paramagnetic metal ions.

The molecules of the present invention can be conjugated to a second antibody to form an antibody heteroconjugate as described by Segal in U.S. Pat. No. 4,676,980. Such heteroconjugate antibodies may additionally bind to haptens (such as fluorescein, etc.), or to cellular markers (e.g., PD-1, 4-1-BB, B7-H4, B7-H5, CD4, CD8, CD14, CD25, CD27, CD40, CD68, CD163, CTLA4, GITR, LAG-3, OX40, TIM3, TIM4, TLR2, LIGHT, etc.) or to cytokines (e.g., IL-7, IL-15, IL-12, IL-4 TGF-beta, IL-10, IL-17, IFNg, Flt3, BLys) or chemokines (e.g., CCL21), etc.

The molecules of the present invention may be attached to solid supports, which are particularly useful for immunoassays or purification of the target antigen or of other molecules that are capable of binding to target antigen that has been immobilized to the support via binding to an antibody or antigen-binding fragment of the present invention. Such solid supports include, but are not limited to, glass, cellulose, polyacrylamide, nylon, polystyrene, polyvinyl chloride or polypropylene.

The present invention additionally includes nucleic acid molecules (DNA or RNA) that encode any such antibodies, fusion proteins or fragments, as well as vector molecules (such as plasmids) that are capable of transmitting or of replication such nucleic acid molecules and expressing such antibodies, fusion proteins or fragments in a cell line. The nucleic acids can be single-stranded, double-stranded, may contain both single-stranded and double-stranded portions.

D. Preferred Modulator Compositions of the Present Invention

As used herein the term "modulate" relates to a capacity to alter an effect or result. In particular, the invention relates to polypeptides that comprise an anti-human B7-H5 antibody or any of its antigen-binding fragments that immunospecifically binds human B7-H5 or molecules that physiospecifically bind B7-H5 that are capable of modulating the binding between B7-H5 and its cognate ligands and/or of modulating the signal transduction that occurs as a consequence of B7-H5—cognate counter-receptor binding. Additionally, multi-specific anti-B7-H5 antibodies, anti-B7-H5 antigen-binding fragments and their respective fusion products that have the added ability to bind CD28H or other cellular ligands or receptors have particular utility in facilitating the co-localization of cells expressing such ligands or receptors to cells that express CD28H.

The invention concerns antibodies, or fragments thereof, or fusion molecules that comprise such antibodies or fragments, that immunospecifically bind to B7-H5 and are capable of substantially blocking B7-H5's interaction with CD28H in vitro, or in a recipient subject or patient. As used herein, a molecule that is "capable of substantially blocking B7-H5's interaction with CD28H" denotes that the provision of such molecule attenuates B7-H5-CD28H interactions by more than 50%, more preferably by more than 60%, more than 70%, more than 80%, more than 90%, more than 95%, more than 99% or most preferably completely attenuates such interaction, as measured by any of the assays disclosed herein. Such antibodies, fragments and fusion molecules have particular utility in attenuating the biological effects of B7-H5-CD28H interactions.

The invention thus particularly relates to the molecules of such embodiments involving humanized antibodies and fragments or human antibodies and fragments.

Most preferably, such molecules will possess sufficient affinity and avidity to be able to bind to B7-H5 when expressed at an endogenous concentration and arrayed on the surface of a subject's cells. The term "endogenous concentration" refers to the level at which a molecule is natively expressed (i.e., in the absence of expression vectors or recombinant promoters) in a normal, cancer or pathogen-infected cell.

(1) Preferred Anti-Human B7-H5 Antibodies and their CDRs

In accordance with the present invention, such molecules can be produced by screening hybridoma lines for those that produce antibody that are immunospecific for human B7-H5, and then optionally screening amongst such lines for those exhibiting modulating activity (e.g., neutralizing activity, agonizing activity, altered signal transducing activity, etc.). The invention particularly provides hamster anti-human B7-H5 clones: 2D3 and 18C3. Antibodies 2D3 and 18C3 are capable of binding to human B7-H5 and are substantially capable of blocking B7-H5's interaction with CD28H. Antibodies that are substantially capable of blocking B7-H5's interaction with CD28H have particular use in the treatment of inflammatory disease and autoimmune disease. Antibodies that are substantially incapable of blocking B7-H5's interaction with CD28H have particular use in diagnostics, since such antibodies can be used to detect the presence, location and prevalence of B7-H5:CD28H interactions.

Antibodies expressed by the anti-human B7-H5 clones which were capable of blocking B7-H5's interaction with CD28H were sequenced to reveal their variable domains. CDR sequences of the variable domains are shown in bold and underlined:

```
Anti-Human B7-H5 Clone 2D3
Heavy Chain Variable Region (SEQ ID NO: 9):
QVQLQQSGAE LVKPGASVKL SCKASGYTFT SHDINWVRQR

PELGLEWIGW IFPGDGSTKF NEKFKGKATL TTDKSSSTAY

IQLSRLTSED SAVYFCARNS FYSMDYWGQG TSVTVSS

Polynucleotide Encoding Heavy Chain
Variable Region (SEQ ID NO: 10):
caggttcaac tgcaacagtc tggagctgaa ctggtaaagc ctggggcttc agtgaagttg tcctgcaagg cttctggcta caccttcaca agccatgata taaactgggt gaggcagagg cctgaactgg gacttgagtg gattggatgg attttttcctg gggatggtag tactaagttc aatgagaagt tcaagggcaa ggccacactg actacagaca aatcctccag cacagcctac atacagctca gcaggctgac gtctgaggac tctgctgtct atttctgtgc aagaaactcc ttctactcta tggactattg gggtcaagga acctcagtca ccgtctcctc a Light Chain Variable Region (SEQ ID NO: 11):
DIVMSQSPSS LAVSAGEKVT MSCKSSQSLL NSRTRKNQLA

WYQQKPGQSP KLLIYWAFIR ESGVPDRFTG SGSGTDFTLT

ISSVQAEDLA VYYCKQSYNL RTFGGGIKLE IK

Polynucleotide Encoding Light
Chain Variable Region (SEQ ID NO: 12):
gacattgtga tgtcacagtc tccatcctcc ctggctgtgt cagcaggaga gaaggtcact atgagctgca aatccagtca gagtctgctc aacagtagaa cccgaaagaa ccagttggct tggtaccagc agaaaccagg acagtctcct aaattactga tctactgggc attcattagg gaatctgggg tccctgatcg cttcacaggc agtggatctg gacagatttc cactctcacc atcagcagtg tgcaggctga agacctggca gtttattact gcaagcaatc ttataatctt cggacgttcg gtggaggcac caagctggaa atcaaac Anti-Human B7-H5 Clone 18C3
Heavy Chain Variable Region (SEQ ID NO: 13):
QVQLQQSGAE LVKPGASVKL SCKASGYTFT SHDINWVRQR

PEQGLEWIGW IFPGDGSTKF NEKFKGKATL TTDKSSSTAY

IQLSRLTSED SAVYFCARNS FYSMDYWGQG TSVTVSS

Polynucleotide Encoding Heavy
Chain Variable Region (SEQ ID NO: 14):
caggttcaac tgcagcagtc tggagctgaa ctggtaaagc ctggggcttc agtgaagttg tcctgcaagg cttctggcta caccttcaca agccatgata taaactgggt gaggcagagg cctgaacagg gacttgagtg gattggatgg attttttcctg gggatggtag tactaagttc aatgagaagt tcaagggcaa ggccacactg actacagaca aatcctccag cacagcctac atacagctca gcaggctgac atctgaggac tctgctgtct atttctgtgc aagaaactcc ttctattcta tggactactg gggtcaagga acctcagtca ccgtctcctc a Light Chain Variable Region (SEQ ID NO: 15):
DIVMSQSPSS LAVSAGEKVT MSCKSSQSLL NSRTRKNQLA

WYQQKPGQSP KLLIYWASTR ESGVPDRFTG SGSGTDFTLT

ISSVQAEDLA VYYCKQSYNL RTFGGGTKLE IK

Polynucleotide Encoding Light Chain
Variable Region (SEQ ID NO: 28):
gacattgtga tgtcacagtc tccatcctcc ctggctgtgt
```

-continued

```
cagcaggaga gaaggtcact atgagctgca aatccagtca gagtctgctc aacagtagaa cccgaaagaa ccagttggct tggtaccagc agaaaccagg gcagtctcct aaactgctga tctactgggc atccactagg gaatctgggg tccctgatcg cttcacaggc agtggatctg ggacagattt cactctcacc atcagcagtg tgcaggctga agacctggca gtttattact gcaagcaatc ttataatctt cggacgttcg gtggaggcac caagctggaa atcaaac
```

(2) Consensus CDRs of the Anti-Human B7-H3 Antibodies of the Present Invention that Block B7-H5:CD28H Interaction Analyses of the CDRs of the identified antibodies were conducted in order to identify consensus CDR sequences and likely variant CDR sequences that would provide similar binding attributes. Such variant CDRs were computed using Blosum62.iij analysis according to Table 1. Table 1 presents the Blosum62.iij substitution scores. The higher the score the more conservative the substitution and thus the more likely the substitution will not affect function.

TABLE 1

|   | A  | R  | N  | D  | C  | Q  | E  | G  | H  | I  | L  | K  | M  | F  | P  | S  | T  | W   | Y  | V  |
|---|----|----|----|----|----|----|----|----|----|----|----|----|----|----|----|----|----|-----|----|----|
| A | +4 | -1 | -2 | -2 |  0 | -1 | -1 |  0 | -2 | -1 | -1 | -1 | -1 | -2 | -1 | +1 |  0 | -3  | -2 |  0 |
| R | -1 | +5 |  0 | -2 | -3 | +1 |  0 | -2 |  0 | -3 | -2 | +2 | -1 | -3 | -2 | -1 | -1 | -3  | -2 | -3 |
| N | -2 |  0 | +6 | +1 | -3 |  0 |  0 |  0 | +1 | -3 | -3 |  0 | -2 | -3 | -2 | +1 |  0 | -4  | -2 | -3 |
| D | -2 | -2 | +1 | +6 | -3 |  0 | +2 | -1 | -1 | -3 | -4 | -1 | -3 | -3 | -1 |  0 | -1 | -4  | -3 | -3 |
| C |  0 | -3 | -3 | -3 | +9 | -3 | -4 | -3 | -3 | -1 | -1 | -3 | -1 | -2 | -3 | -1 | -1 | -2  | -2 | -1 |
| Q | -1 | +1 |  0 |  0 | -3 | +5 | +2 | -2 |  0 | -3 | -2 | +1 |  0 | -3 | -1 |  0 | -1 | -2  | -1 | -2 |
| E | -1 |  0 |  0 | +2 | -4 | +2 | +5 | -2 |  0 | -3 | -3 | +1 | -2 | -3 | -1 |  0 | -1 | -3  | -2 | -2 |
| G |  0 | -2 |  0 | -1 | -3 | -2 | -2 | +6 | -2 | -4 | -4 | -2 | -3 | -3 | -2 |  0 | -2 | -2  | -3 | -3 |
| H | -2 |  0 | +1 | -1 | -3 |  0 |  0 | -2 | +8 | -3 | -3 | -1 | -2 | -1 | -2 | -1 | -2 | -2  | +2 | -3 |
| I | -1 | -3 | -3 | -3 | -1 | -3 | -3 | -4 | -3 | +4 | +2 | -3 | +1 |  0 | -3 | -2 | -1 | -3  | -1 | +3 |
| L | -1 | -2 | -3 | -4 | -1 | -2 | -3 | -4 | -3 | +2 | +4 | -2 | +2 |  0 | -3 | -2 | -1 | -2  | -1 | +1 |
| K | -1 | +2 |  0 | -1 | -3 | +1 | +1 | -2 | -1 | -3 | -2 | +5 | -1 | -3 | -1 |  0 | -1 | -3  | -2 | -2 |
| M | -1 | -1 | -2 | -3 | -1 |  0 | -2 | -3 | -2 | +1 | +2 | -1 | +5 |  0 | -2 | -1 | -1 | -1  | -1 | +1 |
| F | -2 | -3 | -3 | -3 | -2 | -3 | -3 | -3 | -1 |  0 |  0 | -3 |  0 | +6 | -4 | -2 | -2 | +1  | +3 | -1 |
| P | -1 | -2 | -2 | -1 | -3 | -1 | -1 | -2 | -2 | -3 | -3 | -1 | -2 | -4 | +7 | -1 | -1 | -4  | -3 | -2 |
| S | +1 | -1 | +1 |  0 | -1 |  0 |  0 |  0 | -1 | -2 | -2 |  0 | -1 | -2 | -1 | +4 | +1 | -3  | -2 | -2 |
| T |  0 | -1 |  0 | -1 | -1 | -1 | -1 | -2 | -2 | -1 | -1 | -1 | -1 | -2 | -1 | +1 | +5 | -2  | -2 |  0 |
| W | -3 | -3 | -4 | -4 | -2 | -2 | -3 | -2 | -2 | -3 | -2 | -3 | -1 | +1 | -4 | -3 | -2 | +11 | +2 | -3 |
| Y | -2 | -2 | -2 | -3 | -2 | -1 | -2 | -3 | +2 | -1 | -1 | -2 | -1 | +3 | -3 | -2 | -2 | +2  | +7 | -1 |
| V |  0 | -3 | -3 | -3 | -1 | -2 | -2 | -3 | -3 | +3 | +1 | -2 | +1 | -1 | -2 | -2 |  0 | -3  | -1 | +4 |

The present invention permits the formation of novel antibodies and antigen-binding fragments having 1, 2, 3, 4, 5 or 6 variant CDRs. Because the methods of the present invention have identified a substantial number of distinct CDRs, the invention permits a recognition of CDR residues that are likely to be required in any variant of a particular identified CDR. Such residues are shown in boldface in Table 2 and Table 3. For those residues that are found to vary among the compared CDRs, the substitution scores of Table 1 provide a means for determining the identities of permitted substitutions. For example, if a particular residue of a particular CDR is found to vary as R or S, then since R and S have a substitution score of −1, any substitution of R or S having a substitution score of −1 or greater are as likely as the observed variants (R or S) (or are more likely than R or S) to create a variant CDR having binding attributes that are sufficiently similar to those of the particular CDR to permit the variant CDR to be employed in lieu thereof so as to form a functional anti-B7-H5 antibody or antigen-binding fragment. For each position, the selection of a residue having a higher substitution score is preferred over the selection of a residue having a lower substitution score.

Table 2 presents an analysis of the heavy chain CDRs of the anti-B7-H5 antibodies and provides the consensus sequence of the observed and preferred variant light chain ("LC") anti-B7-H5 CDRs of the present invention.

TABLE 2

| Anti-B7-H5 Heavy Chain CDRs | | |
|---|---|---|
| Antibody | Sequence | SEQ ID NO |
| Heavy Chain CDR1 | | |
| 2D3 | G Y T F T S H D | 16 |
| 18C3 | G Y T F T S H D | 16 |
| HC CDR1 Consensus Sequence: | G Y T F T S H D | 16 |
| Heavy Chain CDR2 | | |
| 2D3 | I F P G D G S T | 17 |
| 18C3 | I F P G D G S T | 17 |
| HC CDR2 Consensus Sequence: | I F P G D G S T | 17 |

TABLE 2-continued

| Anti-B7-H5 Heavy Chain CDRs | | |
|---|---|---|
| Antibody | Sequence | SEQ ID NO |
| Heavy Chain CDR3 | | |
| 2D3 | A R N S F Y S M D Y | 18 |
| 18C3 | A R N S F Y S M D Y | 18 |
| HC CDR3 Consensus Sequence: | A R N S F Y S M D Y | 18 |

Table 3 presents an analysis of the light chain CDRs of the anti-B7-H5 antibodies and provides the consensus sequence of the observed and preferred variant anti-B7-H5 heavy chain ("HC") CDRs of the present invention.

TABLE 3

Anti-B7-H5 Light Chain CDRs

| Antibody | Sequence | SEQ ID NO |
|---|---|---|
| *Light Chain CDR1* | | |
| 2D3 | Q S L L N S R T R K NQ | 19 |
| 18C3 | Q S L L N S R T R K NQ | 19 |
| HC CDR1 Consensus Sequence: | Q S L L N S R T T K NQ | 19 |
| *Light Chain CDR2* | | |
| 2D3 | W A F | 20 |
| 18C3 | W A S | 21 |
| LC CDR2 Consensus Sequence: | W A X$_1$ | 22 |
| *Light Chain CDR3* | | |
| 2D3 | K Q S Y N L R T | 23 |
| 18C3 | K Q S Y N L R T | 23 |
| LC CDR3 Consensus Sequence: | K Q S Y N L R T | 23 |

X$_1$ is F or S or a substitution having an equal or greater substitution score (i.e., ≥-2): A, C, H, I, L, M, F, S, T, W, Y, or V Thus, in addition to antibodies and antigen-binding fragments thereof that possess the CDRs of the anti-B7-H5 antibodies: 2D3 and 13C3, the invention additionally provides antibodies and antigen-binding fragments thereof that possess CDRs having the above-described light and/or heavy chain consensus sequences.

The present invention encompasses antibodies or fragments thereof comprising an amino acid sequence of a variable heavy chain and/or variable light chain that is at least 45%, at least 50%, at least 55%, at least 60%, at least 65%, at least 70%, at least 75%, at least 80%, at least 85%, at least 90%, at least 95%, or at least 99% identical to the amino acid sequence of the variable heavy chain and/or light chain of the hamster monoclonal antibody produced by any of the above clones, and which exhibit immunospecific binding to B7-H5. The present invention further encompasses antibodies or fragments thereof that comprise a CDR that is at least 45%, at least 50%, at least 55%, at least 60%, at least 65%, at least 70%, at least 75%, at least 80%, at least 85%, at least 90%, at least 95%, or at least 99% identical to the amino acid sequence of a CDR of the above-listed clones and which exhibit immunospecific binding to B7-H5. The determination of percent identity of two amino acid sequences can be determined by BLAST protein comparison.

In a preferred embodiment, the antibody is a immunoglobulin molecule (e.g., an antibody, diabody, fusion protein, etc.) that comprises one, two or three light chain CDRs and one, two or three heavy chain CDRs (most preferably three light chain CDRs and three heavy chain CDRs), wherein the light chain CDRs include:
  (1) the light chain CDR1 of anti-human B7-H5 antibodies 2D3/18C3;
  (2) a light chain CDR2 of anti-human B7-H5 antibody 2D3 or anti-human B7-H5 antibody 18C3 or a consensus sequence of the CDR2s of such antibodies; and
  (3) the light chain CDR3 of anti-human B7-H5 antibodies 2D3/18C3;

In an alternative preferred embodiment, the immunoglobulin molecule comprises one, two or three light chain CDRs and one, two or three heavy chain CDRs (most preferably three light chain CDRs and three heavy chain CDRs), wherein the heavy chain CDRs include:
  (1) the heavy chain CDR1 of anti-human B7-H5 antibodies 2D3/18C3;
  (2) the heavy chain CDR2 of anti-human B7-H5 antibodies 2D3/18C3; and
  (2) the heavy chain CDR3 of anti-human B7-H5 antibodies 2D3/18C3.

In a specific embodiment, an antibody or an antigen-binding fragment thereof of the present invention will comprise one, two, three, four, five, or more preferably, all 6 CDRs of the above-described preferred antibodies and will exhibit the ability to bind to human B7-H5.

(3) CD28H Fusion Proteins

It has been discovered that CD28H fusion proteins can be antagonists of signal transduction between B7-H5 and CD28H. Therefore, CD28H fusion proteins and methods of use thereof to down-modulate the immune system are also disclosed. Therefore, receptor fusion polypeptides typically block the ability of ligands to bind to transmembrane CD28H, and induce or maintain B7-H5:CD28H mediated signal transduction.

CD28H fusion polypeptides disclosed herein have a first fusion partner including all or a part of a CD28H polypeptide fused (i) directly to a second polypeptide or, (ii) optionally, fused to a linker peptide sequence that is fused to the second polypeptide. Such fusion proteins may form dimers or multimers. The peptide/polypeptide linker domain can either be a separate domain, or alternatively can be contained within one of the other domains (CD28H polypeptide or second polypeptide) of the fusion protein. Similarly, the domain that functions to dimerize or multimerize the fusion protein can either be a separate domain, or alternatively can be contained within one of the other domains (CD28H polypeptide, second polypeptide or peptide/polypeptide linker domain) of the fusion protein. In one embodiment, the dimerization/multimerization domain and the peptide/polypeptide linker domain are the same.

Fusion proteins disclosed herein are of formula I: N—R$_1$-R$_2$-R$_3$-C, wherein "N" represents the N-terminus of the fusion protein, "C" represents the C-terminus of the fusion protein. In the preferred embodiment, "R$_1$" is a CD28H polypeptide, "R$_2$" is an optional peptide/polypeptide linker domain, and "R$_3$" is a second polypeptide. Alternatively, R$_3$ may be a CD28H polypeptide and R$_1$ may be a second polypeptide.

a. First Fusion Partner

The receptor fusion proteins can include a full-length CD28H polypeptide, or can contain a fragment or variant of a full length a CD28H. In preferred embodiment the first fusion partner is a soluble fragment of CD28H, for example, part or all of the extracellular domain of CD28H, or a variant thereof. Any mammalian sequence CD28H can be used. As an example, human sequences, as well as known isoforms and variants thereof, are provided in the sequences above. In some embodiments, other mammalian sequences, such as mouse sequences, are known in the art and can be used. Human CD28H polypeptides useful in the disclosed fusion proteins can have an amino acid sequence least 60%, 65%, 70%, 75%, 80%, 85%, 90%, 95%, 99%, or 100% sequence identity to SEQ ID NO:7, or preferably 60%, 65%, 70%, 75%, 80%, 85%, 90%, 95%, 99%, or 100% sequence identity to the extracellular domain of SEQ ID NO:7. Human CD28H polypeptides useful in the disclosed fusion proteins can be encoded by a nucleic acid sequence least 60%, 65%, 70%, 75%, 80%, 85%, 90%, 95%, 99%, or 100% sequence identity to SEQ ID NO:8, or preferably 60%, 65%, 70%, 75%, 80%, 85%, 90%, 95%, 99%, or 100% sequence identity to the extracellular domain encoded by the nucleic acid sequence of SEQ ID NO:8.

b. Second Fusion Partner

The CD28H polypeptide may be fused to a second polypeptide. The presence of the second polypeptide can alter the solubility, stability, affinity and/or valency of the fusion polypeptide. As used herein, "valency" refers to the number of binding sites available per molecule. In one embodiment the second polypeptide is a polypeptide from a different source or different protein.

In one embodiment, the second polypeptide contains one or more domains of an immunoglobulin heavy chain constant region, preferably having an amino acid sequence corresponding to the hinge, $C_H2$ and $C_H3$ regions of a human immunoglobulin Cγ1 chain or to the hinge, $C_H2$ and $C_H3$ regions of a murine immunoglobulin Cγ2a chain.

In a preferred dimeric fusion protein, the dimer results from the covalent bonding of Cys residue in the hinge region of two of the Ig heavy chains that are the same Cys residues that are disulfide linked in dimerized normal Ig heavy chains. Such proteins can be referred to as CD28H-Ig.

In one embodiment, the immunoglobulin constant domain may contain one or more amino acid insertions, deletions or substitutions that enhance binding to specific cell types, increase the bioavailablity, or increase the stability of the CD28H polypeptides, fusion proteins, or fragments thereof. Suitable amino acid substitutions include conservative and non-conservative substitutions, as described above.

In another embodiment the second polypeptide may have a conjugation domain through which additional molecules can be bound to the CD28H fusion proteins. In one such embodiment, the conjugated molecule is capable of targeting the fusion protein to a particular organ or tissue. In another such embodiment the conjugated molecule is another immunomodulatory agent that can enhance or augment the effects of the CD28H fusion protein. In another embodiment the conjugated molecule is Polyethylene Glycol (PEG).

The Fc portion of the fusion protein may be varied by isotype or subclass, may be a chimeric or hybrid, and/or may be modified, for example to improve effector functions, control of half-life, tissue accessibility, augment biophysical characteristics such as stability, and improve efficiency of production (and less costly). Many modifications useful in construction of disclosed fusion proteins and methods for making them are known in the art, see for example Mueller, et al., *Mol. Immun.*, 34(6):441-452 (1997), Swann, et al., *Cur. Opin. Immun.*, 20:493-499 (2008), and Presta, *Cur. Opin. Immun.* 20:460-470 (2008). In some embodiments the Fc region is the native IgG1, IgG2, or IgG4 Fc region. In some embodiments the Fc region is a hybrid, for example a chimeric consisting of IgG2/IgG4 Fc constant regions. Medications to the Fc region include, but are not limited to, IgG4 modified to prevent binding to Fc gamma receptors and complement, IgG1 modified to improve binding to one or more Fc gamma receptors, IgG1 modified to minimize effector function (amino acid changes), IgG1 with altered/no glycan (typically by changing expression host), and IgG1 with altered pH-dependent binding to FcRn. The Fc region may include the entire hinge region, or less than the entire hinge region.

The therapeutic outcome in patients treated with rituximab (a chimeric mouse/human IgG1 monoclonal antibody against CD20) for non-Hodgkin's lymphoma or Waldenstrom's macroglobulinemia correlated with the individual's expression of allelic variants of Fcγ receptors with distinct intrinsic affinities for the Fc domain of human IgG1. In particular, patients with high affinity alleles of the low affinity activating Fc receptor CD16A (FcγRIIIA) showed higher response rates and, in the cases of non-Hodgkin's lymphoma, improved progression-free survival. In another embodiment, the Fc domain may contain one or more amino acid insertions, deletions or substitutions that reduce binding to the low affinity inhibitory Fc receptor CD32B (FcγRIIB) and retain wild-type levels of binding to or enhance binding to the low affinity activating Fc receptor CD16A (FcγRIIIA).

Another embodiment includes IgG2-4 hybrids and IgG4 mutants that have reduce binding to FcR which increase their half life. Representative IG2-4 hybrids and IgG4 mutants are described in Angal, S. et al., *Molecular Immunology*, 30(1):105-108 (1993); Mueller, J. et al., *Molecular Immunology*, 34(6): 441-452 (1997); and U.S. Pat. No. 6,982,323 to Wang et al. In some embodiments the IgG1 and/or IgG2 domain is deleted for example, Angal et al. describe IgG1 and IgG2 having serine 241 replaced with a proline.

In a preferred embodiment, the Fc domain contains amino acid insertions, deletions or substitutions that enhance binding to CD16A. A large number of substitutions in the Fc domain of human IgG1 that increase binding to CD16A and reduce binding to CD32B are known in the art and are described in Stavenhagen, et al., *Cancer Res.*, 57(18):8882-90 (2007). Exemplary variants of human IgG1 Fc domains with reduced binding to CD32B and/or increased binding to CD16A contain F243L, R929P, Y300L, V3051 or P296L substitutions. These amino acid substitutions may be present in a human IgG1 Fc domain in any combination. In one embodiment, the human IgG1 Fc domain variant contains a F243L, R929P and Y300L substitution. In another embodiment, the human IgG1 Fc domain variant contains a F243L, R929P, Y300L, V3051 and P296L substitution. In another embodiment, the human IgG1 Fc domain variant contains an N297Q substitution, as this mutation abolishes FcR binding.

c. Peptide or Polypeptide Linker Domain

The disclosed CD28H fusion proteins optionally contain a peptide or polypeptide linker domain that separates the CD28H polypeptide from the second polypeptide.

1. Hinge Region of Antibodies

In one embodiment, the linker domain contains the hinge region of an immunoglobulin. In a preferred embodiment, the hinge region is derived from a human immunoglobulin. Suitable human immunoglobulins that the hinge can be derived from include IgG, IgD and IgA. In a preferred embodiment, the hinge region is derived from human IgG. Amino acid sequences of immunoglobulin hinge regions and other domains are well known in the art.

2. Other Peptide/Polypeptide Linker Domains

Other suitable peptide/polypeptide linker domains include naturally occurring or non-naturally occurring peptides or polypeptides. Peptide linker sequences are at least 2 amino acids in length. Preferably the peptide or polypeptide domains are flexible peptides or polypeptides. A "flexible linker" herein refers to a peptide or polypeptide containing two or more amino acid residues joined by peptide bond(s) that provides increased rotational freedom for two polypeptides linked thereby than the two linked polypeptides would have in the absence of the flexible linker. Such rotational freedom allows two or more antigen binding sites joined by the flexible linker to each access target antigen(s) more efficiently. Exemplary flexible peptides/polypeptides include, but are not limited to, the amino acid sequences Gly-Ser, Gly-Ser-Gly-Ser (SEQ ID NO:16), Ala-Ser, Gly- Gly-Gly-Ser (SEQ ID NO:17), (Gly₄-Ser)₃ (SEQ ID NO:18) and (Gly₄-Ser)₄ (SEQ ID NO:19). Additional flexible peptide/polypeptide sequences are well known in the art.

In one embodiment, the first fusion partner is a fragment of CD28H. In a preferred embodiment, the fusion protein includes the extracellular domain of CD28H, or a fragment thereof, fused to an Ig Fc region. Recombinant CD28H-Ig fusion proteins can be prepared by fusing the coding region of the extracellular domain of a neuropilin or a plexin or a fragment thereof to the Fc region of human IgG1 or mouse IgG2a, or other suitable Ig domain, as described previously (Chapoval, et al., *Methods Mol. Med.,* 45:247-255 (2000)).

d. Exemplary Fusion Protein

The amino acid sequence of a representative human CD28H-Ig fusion protein is (SEQ ID NO:20), a CD28H-hIgG4 (CD28H ECD aa23-140, light chain kappa signal peptide: CD28H sequences are shown in boldface; mutated human IgG4 Fc sequences are shown underlined, with Serine 228 to Proline mutation double underline):

LSVQQGPNLLQVRQGSQATLVCQVDQATAWERLRVKWTKDGAILCQPYIT

NGSLSLGVCGPQGRLSWQAPSHLTLQLDPVSLNHSGAYVCWAAVEIPELE

EAEGNITRLFVDPDDPTQESKYGPPCP<u>P</u>CPAPEFLGGPSVFLFPPKPKDT

LMISRTPEVTCVVVDVSQEDPEVQFNWYVDGVEVHNAKTKPREEQFNSTY

RVVSVLTVLHQDWLNGKEYKCKVSNKGLPSSIEKTISKAKGQPREPQVYT

LPPSQEEMTKNQVSLTCLVKGFYPSDIAVEWESNGQPENNYKTTPPVLDS

DGSFFLYSRLTVDKSRWQEGNVFSCSVMHEALHNHYTQKSLSLSPGK

The fusion protein may additionally comprise an N-terminal leader sequence (light chain kappa leader sequence) (such residues 1-20 of SEQ ID NO:21),

MSVPTQVLGLLLLWLTDARC or a naturally occurring CD28H leader sequence such as (SEQ ID NO:22):

MGSPGMVLGLLVQIWALQEASS

Although the CD28H sequences are shown fused to a human IgG4 region, in accordance with the present invention, such sequences can alternatively be fused to any Ig isotype, or indeed to any other protein.

A DNA sequence encoding human CD28H-Ig of SEQ ID NO:20 including the signal sequence of SEQ ID NO:21 is (SEQ ID NO:23):

ATGTCCGTGCCCACCCAGGTGCTGGGATTGCTGCTGCTGTGGCTGACCG

ACGCCAGATGCCTGTCTGTGCAGCAGGGCCCTAACCTGCTGCAAGTGCG

GCAGGGCTCTCAGGCTACACTCGTGTGTCAGGTGGACCAGGCCACCGCC

TGGGAGAGACTGAGAGTGAAGTGGACCAAGGACGGCGCCATCCTGTGCC

AGCCCTACATCACCAACGGCTCCCTGTCCCTGGGCGTGTGTGGACCTCA

GGGCAGACTGTCTTGGCAGGCCCCTTCTCACCTGACCCTGCAGCTGGAC

CCTGTGTCCCTGAATCACTCCGGCGCCTACGTGTGTTGGGCCGCTGTGG

AAATCCCCGAGCTGGAAGAGGCCGAGGGCAACATCACCCGGCTGTTCGT

GGACCCTGACGACCCTACCCAGGAATCTAAGTACGGCCCTCCCTGCCCT

CCTTGCCCAGCCCCTGAATTTCTGGGCGGACCCTCCGTGTTCCTGTTCC

CCCCAAAGCCCAAGGACACCCTGATGATCTCCCGGACCCCCGAAGTGAC

CTGCGTGGTGGTGGATGTGTCCCAGGAAGATCCCGAGGTGCAGTTCAAT

TGGTACGTGGACGGCGTGGAAGTGCACAACGCCAAGACCAAGCCCAGAG

AGGAACAGTTCAACTCCACCTACCGGGTGGTGTCCGTGCTGACCGTGCT

GCACCAGGATTGGCTGAACGGCAAAGAGTACAAGTGCAAGGTGTCCAAC

AAGGGCCTGCCCAGCTCCATCGAAAAGACCATCTCCAAGGCCAAGGGCC

AGCCCCGGGAACCCCAGGTGTACACACTGCCTCCAAGCCAGGAAGAGAT

GACCAAGAACCAGGTGTCACTGACCTGTCTCGTGAAGGGCTTCTACCCC

TCCGATATCGCCGTGGAATGGGAGTCCAACGGCCAGCCTGAGAACAACT

ACAAGACCACCCCCCCTGTGCTGGACTCCGACGGCTCCTTCTTCCTGTA

CTCCCGCCTGACCGTGGACAAGTCCAGATGGCAGGAAGGCAACGTGTTC

TCCTGCTCCGTGATGCACGAGGCCCTGCACAACCACTACACCCAGAAGT

CCCTGAGCCTGTCCCCCGGCAAGTGA

E. Therapeutic and Prophylactic Uses of the Preferred Compositions of the Present Invention As used herein, the terms "treat," "treating," "treatment" and "therapeutic use" refer to the elimination, reduction or amelioration of one or more symptoms of a disease or disorder that would benefit from an increased or decreased immune response. As used herein, a "therapeutically effective amount" refers to that amount of a therapeutic agent sufficient to mediate an altered immune response, and more preferably, a clinically relevant altered immune response, sufficient to mediate a reduction or amelioration of a symptom of a disease or condition. An effect is clinically relevant if its magnitude is sufficient to impact the health or prognosis of a recipient subject. A therapeutically effective amount may refer to the amount of therapeutic agent sufficient to reduce or minimize disease progression, e.g., delay or minimize an autoimmune response or an inflammatory response or a transplant rejection. A therapeutically effective amount may also refer to the amount of the therapeutic agent that provides a therapeutic benefit in the treatment or management of a disease. Further, a therapeutically effective amount with respect to a therapeutic agent, B7-H5 antibody or B7-H5 fusion protein or CD28H fusion protein, means that amount of therapeutic agent alone, or in combination with other therapies, that provides a therapeutic benefit in the treatment or management of a disease, e.g., sufficient to enhance the therapeutic efficacy of a therapeutic antibody sufficient to treat or manage a disease.

As used herein, the term "prophylactic agent" refers to an agent that can be used in the prevention of a disorder or disease prior to the detection of any symptoms of such disorder or disease. A "prophylactically effective" amount is the amount of prophylactic agent sufficient to mediate such protection. A prophylactically effective amount may also refer to the amount of the prophylactic agent that provides a prophylactic benefit in the prevention of disease. Further, a prophylactically effective amount with respect to a prophylactic agent means that amount of prophylactic agent alone, or in combination with other agents, that provides a prophylactic benefit in the prevention of disease.

The dosage amounts and frequencies of administration provided herein are encompassed by the terms therapeutically effective and prophylactically effective. The dosage and frequency further will typically vary according to factors specific for each patient depending on the specific therapeutic or prophylactic agents administered, the severity and type of cancer, the route of administration, as well as age, body weight, response, and the past medical history of the patient. Suitable regimens can be selected by one skilled in the art by considering such factors and by following, for example, dosages reported in the literature and recommended in the *Physician's Desk Reference* (56$^{th}$ Ed., 2002).

The present invention relates to molecules, such as anti-B7-H5 antibodies (and fragments of such antibodies that bind to B7-H5) or CD28H Ig that, by binding to B7-H5 antagonize (i.e., attenuate or impair) B7-H5 function and/or binding to CD28H and thus attenuate or impair T cell proliferation and/or cytokine production. The administration of such molecules to a subject down-modulates the immune system of the subject.

Such down-modulation of the immune system is desirable in the treatment of inflammatory and auto-immune diseases and transplant rejection. Examples of autoimmune disorders that may be treated by administering the antibodies of the present invention include, but are not limited to, alopecia areata, ankylosing spondylitis, antiphospholipid syndrome, autoimmune Addison's disease, autoimmune diseases of the adrenal gland, autoimmune hemolytic anemia, autoimmune hepatitis, autoimmune oophoritis and orchitis, autoimmune thrombocytopenia, Behcet's disease, bullous pemphigoid, cardiomyopathy, celiac sprue-dermatitis, chronic fatigue immune dysfunction syndrome (CFIDS), chronic inflammatory demyelinating polyneuropathy, Churg-Strauss syndrome, cicatrical pemphigoid, CREST syndrome, cold agglutinin disease, Crohn's disease, discoid lupus, essential mixed cryoglobulinemia, fibromyalgia-fibromyositis, glomerulonephritis, Graves' disease, Guillain-Barre, Hashimoto's thyroiditis, idiopathic pulmonary fibrosis, idiopathic thrombocytopenia purpura (ITP), IgA neuropathy, juvenile arthritis, lichen planus, lupus erthematosus, Ménière's disease, mixed connective tissue disease, multiple sclerosis, Neuromyelitis optica (NMO), type 1 or immune-mediated diabetes mellitus, myasthenia gravis, pemphigus vulgaris, pernicious anemia, polyarteritis *nodosa*, polychrondritis, polyglandular syndromes, polymyalgia rheumatica, polymyositis and dermatomyositis, primary agammaglobulinemia, primary biliary cirrhosis, psoriasis, psoriatic arthritis, Raynauld's phenomenon, Reiter's syndrome, Rheumatoid arthritis, sarcoidosis, scleroderma, Sjögren's syndrome, stiff-man syndrome, systemic lupus erythematosus, lupus erythematosus, takayasu arteritis, temporal arteristis/giant cell arteritis, ulcerative colitis, uveitis, vasculitides such as dermatitis herpetiformis vasculitis, vitiligo, and Wegener's granulomatosis.

Examples of inflammatory diseases which can be prevented, treated or managed with the disclosed anti-B7-H5 antibodies and antigen binding fragments and CD28H fusion proteins, particularly CD28H-Ig fusion proteins, thereof include, but are not limited to, asthma, encephilitis, inflammatory bowel disease, chronic obstructive pulmonary disease (COPD), allergic disorders, septic shock, pulmonary fibrosis, undifferentiated spondyloarthropathy, undifferentiated arthropathy, arthritis, inflammatory osteolysis, and chronic inflammation resulting from chronic viral or bacterial infections.

The anti-B7-H5 antibodies can be employed to produce anti-idiotypic peptides or antibodies (Wallmann, J. et al. (2010) "*Anti-Ids in Allergy: Timeliness of a Classic Concept,*" World Allergy Organiz. J. 3(6):195-201; Nardi, M. et al. (2000) "*Antiidiotype Antibody Against Platelet Anti-GpIIIa Contributes To The Regulation Of Thrombocytopenia In HIV-1-ITP Patients,*" J. Exp. Med. 191(12):2093-2100) or mimetics (Zang, Y. C. et al. (2003) "*Human Anti-Idiotypic T Cells Induced By TCR Peptides Corresponding To A Common CDR3 Sequence Motif In Myelin Basic Protein-Reactive T Cells,*" Int. Immunol. 15(9):1073-1080; Loiarro, M. et al. (Epub 2010 Apr. 8) "*Targeting TLR/IL-1R Signalling In Human Diseases,*" Mediators Inflamm. 2010:674363) of B7-H5. Such molecules serve as surrogates for B7-H5, and thus their administration to a subject down-modulates the immune system of such subject by engaging the CD28H counter-receptor and preventing it from binding to endogenous B7-H5 receptor. Such molecules have utility in the treatment of graft vs. host disease, inflammatory, and auto-immune diseases.

Thus, the antibodies and antigen-binding fragments and fusion proteins of the present invention have utility in the treatment of graft vs. host disease, inflammatory and auto-immune diseases.

Similarly, agonist antibodies that enhance binding between such antibodies and such receptor/ligand, and other receptor agonists such a B7-H5 fusion proteins have utility as agonists of B7-H5 signaling, and therefore have utility in the treatment of cancer and infectious disease. Accordingly, the present invention also relates to CD28H agonist molecules, such as B7-H5-Ig fusion proteins that, by binding to CD28H agonize CD28H function (i.e. signal transduction) and/or binding to B7-H5 and thus augment or stimulate T cell proliferation and/or cytokine production. The administration of such molecules to a subject up-modulates the immune system of the subject and can be used to treat subjects with cancer or an infectious disease. As the B7-H5 pathway is involved in T cell activation, such molecules are particularly useful in combination with vaccines.

The CD28H agonists provided herein are generally useful in vivo and ex vivo as immune response-stimulating therapeutics. For example, the CD28H agonists are useful for stimulating or enhancing an immune response in host for treating cancer by administering to subject an amount of CD28H agonists. The types of cancer that may be treated with the provided compositions and methods include, but are not limited to, the following: bladder, brain, breast, cervical, colo-rectal, esophageal, kidney, liver, lung, nasopharangeal, pancreatic, prostate, skin, stomach, uterine, ovarian, testicular and hematologic.

Malignant tumors which may be treated are classified herein according to the embryonic origin of the tissue from which the tumor is derived. Carcinomas are tumors arising from endodermal or ectodermal tissues such as skin or the epithelial lining of internal organs and glands. Sarcomas, which arise less frequently, are derived from mesodermal connective tissues such as bone, fat, and cartilage. The leukemias and lymphomas are malignant tumors of hematopoietic cells of the bone marrow. Leukemias proliferate as single cells, whereas lymphomas tend to grow as tumor masses. Malignant tumors may show up at numerous organs or tissues of the body to establish a cancer.

The CD28H agonists can be administered for the treatment of local or systemic viral infections, including, but not limited to, immunodeficiency (e.g., HIV), papilloma (e.g., HPV), herpes (e.g., HSV), encephalitis, influenza (e.g., human influenza virus A), and common cold (e.g., human rhinovirus) viral infections. For example, pharmaceutical formulations including the CD28H agonist compositions can be administered topically to treat viral skin diseases such as herpes lesions or shingles, or genital warts. Pharmaceutical formulations of CD28H agonist compositions can also be administered to treat systemic viral diseases, including, but not limited to, AIDS, influenza, the common cold, or encephalitis.

Representative infections that can be treated, include but are not limited to infections cause by microorganisms including, but not limited to, *Actinomyces, Anabaena, Bacillus, Bacteroides, Bdellovibrio, Bordetella, Borrelia, Campylobacter, Caulobacter, Chlamydia, Chlorobium, Chromatium, Clostridium, Corynebacterium, Cytophaga, Deinococcus, Escherichia, Francisella, Halobacterium, Heliobacter, Haemophilus,* Hemophilus influenza type B (HIB), *Histoplasma, Hyphomicrobium, Legionella, Leishmania, Leptspirosis, Listeria,* Meningococcus A, B and C, *Methanobacterium, Micrococcus, Myobacterium, Mycoplasma, Myxococcus, Neisseria, Nitrobacter, Oscillatoria, Prochloron, Proteus, Pseudomonas, Phodospirillum, Rickettsia, Salmonella, Shigella, Spirillum, Spirochaeta, Staphylococcus, Streptococcus, Streptomyces, Sulfolobus, Thermoplasma, Thiobacillus,* and *Treponema, Vibrio, Yersinia, Cryptococcus neoformans, Histoplasma capsulatum, Candida albicans, Candida tropicalis, Nocardia asteroides, Rickettsia ricketsii, Rickettsia typhi, Mycoplasma pneumoniae, Chlamydial psittaci, Chlamydial trachomatis, Plasmodium falciparum, Plasmodium vivax, Trypanosoma brucei, Entamoeba histolytica, Toxoplasma gondii, Trichomonas vaginalis* and *Schistosoma mansoni.*

The disclosed CD28H agonists or nucleic acids encoding the same may be administered alone or in combination with any other suitable treatment. In one embodiment the CD28H agonists can be administered in conjunction with, or as a component of, a vaccine composition. Suitable components of vaccine compositions antigens and/or adjuvants. The disclosed CD28H agonists can be administered prior to, concurrently with, or after the administration of a vaccine. In one embodiment the CD28H agonist composition is administered at the same time as administration of a vaccine.

The disclosed CD28H agonist compositions may be administered in conjunction with prophylactic vaccines, or therapeutic vaccines, which can be used to initiate or enhance a subject's immune response to a pre-existing antigen, such as a tumor antigen in a subject with cancer.

The desired outcome of a prophylactic, therapeutic or de-sensitized immune response may vary according to the disease, according to principles well known in the art. Similarly, immune responses against cancer, allergens or infectious agents may completely treat a disease, may alleviate symptoms, or may be one facet in an overall therapeutic intervention against a disease. For example, the stimulation of an immune response against a cancer may be coupled with surgical, chemotherapeutic, radiologic, hormonal and other immunologic approaches in order to affect treatment.

F. Methods of Administration

Various delivery systems are known and can be used to administer the therapeutic or prophylactic compositions, e.g., encapsulation in liposomes, microparticles, microcapsules, recombinant cells capable of expressing the antibody or fusion protein, receptor-mediated endocytosis (see, e.g., Wu and Wu, 1987, *J. Biol. Chem.* 262:4429-4432), construction of a nucleic acid as part of a retroviral or other vector, etc.

Methods of administering antibodies and fusion proteins include, but are not limited to, parenteral administration (e.g., intradermal, intramuscular, intraperitoneal, intravenous and subcutaneous), epidural, and mucosal (e.g., intranasal and oral routes). In a specific embodiment, the antibodies or fusion proteins are administered intramuscularly, intravenously, or subcutaneously. The compositions may be administered by any convenient route, for example, by infusion or bolus injection, by absorption through epithelial or mucocutaneous linings (e.g., oral mucosa, rectal and intestinal mucosa, etc.) and may be administered together with other biologically active agents. Administration can be systemic or local. In addition, pulmonary administration can also be employed, e.g., by use of an inhaler or nebulizer, and formulation with an aerosolizing agent. See, e.g., U.S. Pat. Nos. 6,019,968; 5,985, 20; 5,985,309; 5,934,272; 5,874,064; 5,855,913; 5,290,540; and 4,880,078; and PCT Publication Nos. WO 92/19244; WO 97/32572; WO 97/44013; WO 98/31346; and WO 99/66903. In a specific embodiment, it may be desirable to administer the pharmaceutical compositions locally to the area in need of treatment; this may be achieved by, for example, and not by way of limitation, local infusion, by injection, or by means of an implant, said implant being of a porous, non-porous, or gelatinous material, including membranes, such as sialastic membranes, or fibers. Preferably, when administering an antibody or fusion protein, care must be taken to use materials to which the antibody or the fusion protein does not absorb.

In some embodiments, the antibodies or fusions proteins are formulated in liposomes for targeted delivery of the antibodies or fusion proteins. Liposomes are vesicles comprised of concentrically ordered phospholipid bilayers which encapsulate an aqueous phase. Liposomes typically comprise various types of lipids, phospholipids, and/or surfactants. The components of liposomes are arranged in a bilayer configuration, similar to the lipid arrangement of biological membranes. Liposomes are particularly preferred delivery vehicles due, in part, to their biocompatibility, low immunogenicity, and low toxicity. Methods for preparation of liposomes are known in the art and are encompassed within the invention, see, e.g., Epstein et al., 1985, *Proc. Natl. Acad. Sci. USA,* 82: 3688; Hwang et al., 1980 *Proc. Natl. Acad. Sci. USA,* 77: 4030-4; U.S. Pat. Nos. 4,485,045 and 4,544,545.

Methods of preparing liposomes with a prolonged serum half-life, i.e., enhanced circulation time, such as those disclosed in U.S. Pat. No. 5,013,556 can be used to make liposomes-antibody compositions. Preferred liposomes are not rapidly cleared from circulation, i.e., are not taken up into the mononuclear phagocyte system (MPS). The invention encompasses sterically stabilized liposomes which are prepared using common methods known to one skilled in the art. Although not intending to be bound by a particular mechanism of action, sterically stabilized liposomes contain lipid components with bulky and highly flexible hydrophilic moieties, which reduces the unwanted reaction of liposomes with serum proteins, reduces oposonization with serum components and reduces recognition by MPS. Sterically stabilized liposomes are preferably prepared using polyethylene glycol. For preparation of liposomes and sterically stabilized liposome, see, e.g., Bendas et al., 2001 *BioDrugs,* 15(4): 215-224; Allen et al., 1987 *FEBS Lett.* 223: 42-6; Klibanov et al., 1990 *FEBS Lett.,* 268: 235-7; Blum et al., 1990, *Biochim. Biophys. Acta.,* 1029: 91-7; Torchilin et al., 1996, *J. Liposome Res.* 6: 99-116; Litzinger et al., 1994, *Biochim. Biophys. Acta,* 1190: 99-107; Maruyama et al., 1991, *Chem. Pharm. Bull.,* 39: 1620-2; Klibanov et al., 1991, *Biochim Biophys Acta*, 1062; 142-8; Allen et al., 1994, *Adv. Drug Deliv. Rev*, 13: 285-309. The invention also encompasses liposomes that are adapted for specific organ targeting, see, e.g., U.S. Pat. No. 4,544,545, or specific cell targeting, see, e.g., U.S. Patent Application Publication No. 2005/0074403. Particularly useful liposomes for use in the disclosed compositions and methods can be generated by reverse phase evaporation method with a lipid composition comprising phosphatidylcholine, cholesterol, and PEG derivatized phosphatidylethanolamine (PEG-PE). Liposomes are extruded through filters of defined pore size to yield liposomes with the desired diameter. In some embodiments, a fragment of an antibody, e.g., F(ab'), may be conjugated to the liposomes using previously described methods, see, e.g., Martin et al., 1982, *J. Biol. Chem.* 257: 286-288.

The B7-H5 antibodies, or B7-H5 or CD28H fusion proteins may also be formulated as immunoliposomes. Immunoliposomes refer to a liposomal composition, wherein an antibody or a fragment thereof is linked, covalently or non-covalently to the liposomal surface. The chemistry of linking an antibody to the liposomal surface is known in the art and encompassed within the invention, see, e.g., U.S. Pat. No. 6,787,153; Allen et al., 1995, Stealth Liposomes, Boca Rotan: CRC Press, 233-44; Hansen et al., 1995, *Biochim. Biophys. Acta*, 1239: 133-144. In most preferred embodiments, immunoliposomes for use in the disclosed methods and compositions are further sterically stabilized. Preferably, the antibodies or fusion proteins are linked covalently or non-covalently to a hydrophobic anchor, which is stably rooted in the lipid bilayer of the liposome. Examples of hydrophobic anchors include, but are not limited to, phospholipids, e.g., phosoatidylethanolamine (PE), phosphatidylinositol (PI). To achieve a covalent linkage between an antibody and a hydrophobic anchor, any of the known biochemical strategies in the art may be used, see, e.g., J. Thomas August, ed., 1997, Gene Therapy: Advances in Pharmacology, Volume 40, Academic Press, San Diego, Calif., p. 399-435. For example, a functional group on an antibody molecule may react with an active group on a liposome associated hydrophobic anchor, e.g., an amino group of a lysine side chain on an antibody may be coupled to liposome associated N-glutaryl-phosphatidylethanolamine activated with water-soluble carbodiimide; or a thiol group of a reduced antibody can be coupled to liposomes via thiol reactive anchors, such as pyridylthiopropionylphosphatidylethanolamine. See, e.g., Dietrich et al., 1996, *Biochemistry*, 35: 1100-1105; Loughrey et al., 1987, *Biochim. Biophys. Acta*, 901: 157-160; Martin et al., 1982, *J. Biol. Chem.* 257: 286-288; Martin et al., 1981, *Biochemistry*, 20: 4429-38. Although not intending to be bound by a particular mechanism of action, immunoliposomal formulations including an antibody or fusion protein are particularly effective as therapeutic agents, since they deliver the antibody or fusion protein to the cytoplasm of the target cell, i.e., the cell comprising the receptor to which the antibody or fusion protein binds. The immunoliposomes preferably have an increased half-life in blood, specifically target cells, and can be internalized into the cytoplasm of the target cells thereby avoiding loss of the therapeutic agent or degradation by the endolysosomal pathway.

The immunoliposomal compositions include one or more vesicle forming lipids, an antibody or a fragment or derivative thereof or a fusion protein, and, optionally, a hydrophilic polymer. A vesicle forming lipid is preferably a lipid with two hydrocarbon chains, such as acyl chains and a polar head group. Examples of vesicle forming lipids include phospholipids, e.g., phosphatidylcholine, phosphatidylethanolamine, phosphatidic acid, phosphatidylinositol, sphingomyelin, and glycolipids, e.g., cerebrosides, gangliosides. Additional lipids useful in the formulations are known to one skilled in the art and encompassed within the invention. In some embodiments, the immunoliposomal compositions further comprise a hydrophilic polymer, e.g., polyethylene glycol, and ganglioside GM1, which increases the serum half-life of the liposome. Methods of conjugating hydrophilic polymers to liposomes are well known in the art and encompassed within the invention. For a review of immunoliposomes and methods of preparing them, see, e.g., U.S. Patent Application Publication No. 2003/0044407; PCT International Publication No. WO 97/38731, Vingerhoeads et al., 1994, *Immunomethods*, 4: 259-72; Maruyama, 2000, *Biol. Pharm. Bull.* 23(7): 791-799; Abra et al., 2002, *Journal of Liposome Research*, 12(1&2): 1-3; Park, 2002, *Bioscience Reports*, 22(2): 267-281; Bendas et al., 2001 *BioDrugs*, 14(4): 215-224, J. Thomas August, ed., 1997, Gene Therapy: Advances in Pharmacology, Volume 40, Academic Press, San Diego, Calif., p. 399-435.

The antibodies and fusion proteins can be packaged in a hermetically sealed container, such as an ampoule or sachette, indicating the quantity of antibody. In one embodiment, the antibodies are supplied as a dry sterilized lyophilized powder or water free concentrate in a hermetically sealed container and can be reconstituted, e.g., with water or saline to the appropriate concentration for administration to a subject. Preferably, the antibodies or fusion proteins are supplied as a dry sterile lyophilized powder in a hermetically sealed container at a unit dosage of at least 5 mg, more preferably at least 10 mg, at least 15 mg, at least 25 mg, at least 35 mg, at least 45 mg, at least 50 mg, or at least 75 mg. The lyophilized antibodies or fusion proteins should be stored at between 2 and 8° C. in their original container and the antibodies should be administered within 12 hours, preferably within 6 hours, within 5 hours, within 3 hours, or within 1 hour after being reconstituted. In an alternative embodiment, antibodies or fusion proteins are supplied in liquid form in a hermetically sealed container indicating the quantity and concentration of the antibody, fusion protein, or conjugated molecule. Preferably, the liquid form of the antibodies or fusion proteins are supplied in a hermetically sealed container at least 1 mg/ml, more preferably at least 2.5 mg/ml, at least 5 mg/ml, at least 8 mg/ml, at least 10 mg/ml, at least 15 mg/kg, at least 25 mg/ml, at least 50 mg/ml, at least 100 mg/ml, at least 150 mg/ml, at least 200 mg/ml of the antibodies of fusion proteins.

The precise dose to be employed in the formulation will also depend on the route of administration, and the seriousness of the condition, and should be decided according to the judgment of the practitioner and each patient's circumstances. Effective doses may be extrapolated from dose-response curves derived from in vitro or animal model test systems. For antibodies and fusion proteins, the dosage administered to a patient is typically 0.0001 mg/kg to 100 mg/kg of the patient's body weight. Preferably, the dosage administered to a patient is between 0.0001 mg/kg and 20 mg/kg, 0.0001 mg/kg and 10 mg/kg, 0.0001 mg/kg and 5 mg/kg, 0.0001 and 2 mg/kg, 0.0001 and 1 mg/kg, 0.0001 mg/kg and 0.75 mg/kg, 0.0001 mg/kg and 0.5 mg/kg, 0.0001 mg/kg to 0.25 mg/kg, 0.0001 to 0.15 mg/kg, 0.0001 to 0.10 mg/kg, 0.001 to 0.5 mg/kg, 0.01 to 0.25 mg/kg or 0.01 to 0.10 mg/kg of the patient's body weight. Generally, human antibodies have a longer half-life within the human body than antibodies from other species due to the immune response to the foreign polypeptides. Thus, lower dosages of human antibodies and less frequent administration is often possible. Further, the dosage and frequency of administration of antibodies or fragments thereof, or fusion proteins may be reduced by enhancing uptake and tissue penetration of the antibodies or fusion proteins by modifications such as, for example, lipidation.

In yet another embodiment, the compositions can be delivered in a controlled release or sustained release system. Any technique known to one of skill in the art can be used to produce sustained release formulations comprising one or more antibodies or fusion proteins. See, e.g., U.S. Pat. No. 4,526,938; PCT publication WO 91/05548; PCT publication WO 96/20698; Ning et al., 1996, "Intratumoral Radioimmunotheraphy of a Human Colon Cancer Xenograft Using a Sustained-Release Gel," *Radiotherapy & Oncology* 39:179-189, Song et al., 1995, "Antibody Mediated Lung Targeting of Long-Circulating Emulsions," *PDA Journal of Pharmaceutical Science & Technology* 50:372-397; Cleek et al., 1997, "Biodegradable Polymeric Carriers for a bFGF Antibody for Cardiovascular Application," *Pro. Int'l. Symp. Control. Rel. Bioact. Mater.* 24:853-854; and Lam et al., 1997, "Microencapsulation of Recombinant Humanized Monoclonal Antibody for Local Delivery," *Proc. Int'l. Symp. Control Rel. Bioact. Mater.* 24:759-760. In one embodiment, a pump may be used in a controlled release system (See Langer, supra; Sefton, 1987, *CRC Crit. Ref Biomed. Eng.* 14:20; Buchwald et al., 1980, Surgery 88:507; and Saudek et al., 1989, *N. Engl. J. Med.* 321:574). In another embodiment, polymeric materials can be used to achieve controlled release of antibodies (see e.g., Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, 1983, J., *Macromol. Sci. Rev. Macromol. Chem.* 23:61; See also Levy et al., 1985, *Science* 228:190; During et al., 1989, Ann. Neurol. 25:351; Howard et al., 1989, *J. Neurosurg.* 7 1:105); U.S. Pat. Nos. 5,679,377; 5,916,597; 5,912,015; 5,989,463; 5,128,326; PCT Publication No. WO 99/15154; and PCT Publication No. WO 99/20253). Examples of polymers used in sustained release formulations include, but are not limited to, poly(2-hydroxy ethyl methacrylate), poly(methyl methacrylate), poly(acrylic acid), poly(ethylene-co-vinyl acetate), poly(methacrylic acid), polyglycolides (PLG), polyanhydrides, poly(N-vinyl pyrrolidone), poly(vinyl alcohol), polyacrylamide, poly(ethylene glycol), polylactides (PLA), poly(lactide-co-glycolides) (PLGA), and polyorthoesters. In yet another embodiment, a controlled release system can be placed in proximity of the therapeutic target (e.g., the lungs), thus requiring only a fraction of the systemic dose (see, e.g., Goodson, in Medical Applications of Controlled Release, supra, vol. 2, pp. 115-138 (1984)). In another embodiment, polymeric compositions useful as controlled release implants are used according to Dunn et al. (See U.S. Pat. No. 5,945,155). This particular method is based upon the therapeutic effect of the in situ controlled release of the bioactive material from the polymer system. The implantation can generally occur anywhere within the body of the patient in need of therapeutic treatment. In another embodiment, a non-polymeric sustained delivery system is used, whereby a non-polymeric implant in the body of the subject is used as a drug delivery system. Upon implantation in the body, the organic solvent of the implant will dissipate, disperse, or leach from the composition into surrounding tissue fluid, and the non-polymeric material will gradually coagulate or precipitate to form a solid, microporous matrix (See U.S. Pat. No. 5,888,533). Controlled release systems are discussed in the review by Langer (1990, *Science* 249:1527-1533). Any technique known to one of skill in the art can be used to produce sustained release formulations comprising one or more therapeutic agents, i.e., B7-H5 antibodies or CD28H fusion proteins. See, e.g., U.S. Pat. No. 4,526,938; International Publication Nos. WO 91/05548 and WO 96/20698; Ning et al., 1996, *Radiotherapy & Oncology* 39:179-189; Song et al., 1995, *PDA Journal of Pharmaceutical Science & Technology* 50:372-397; Cleek et al., 1997, *Pro. Int'l. Symp. Control. Rel. Bioact. Mater.* 24:853-854; and Lam et al., 1997, *Proc. Int'l. Symp. Control Rel. Bioact. Mater.* 24:759-760.

In a specific embodiment wherein the therapeutic or prophylactic composition is a nucleic acid encoding a B7-H5 antibody or an antigen-binding fragment thereof, or a nucleic acid encoding a CD28H fusion protein, for example, CD28H-Ig fusion protein, the nucleic acid can be administered in vivo to promote expression of its encoded antibody or fusion, by constructing it as part of an appropriate nucleic acid expression vector and administering it so that it becomes intracellular, e.g., by use of a retroviral vector (See U.S. Pat. No. 4,980,286), or by direct injection, or by use of microparticle bombardment (e.g., a gene gun; Biolistic, Dupont), or coating with lipids or cell-surface receptors or transfecting agents, or by administering it in linkage to a homeobox-like peptide which is known to enter the nucleus (See e.g., Joliot et al., 1991, *Proc. Natl. Acad. Sci. USA* 88:1864-1868), etc. Alternatively, a nucleic acid can be introduced intracellularly and incorporated within host cell DNA for expression by homologous recombination.

Treatment of a subject with a therapeutically or prophylactically effective amount of antibody or fusion protein can include a single treatment or, preferably, can include a series of treatments.

G. Pharmaceutical Compositions

The compositions include bulk drug compositions useful in the manufacture of pharmaceutical compositions (e.g., impure or non-sterile compositions) and pharmaceutical compositions (i.e., compositions that are suitable for administration to a subject or patient) which can be used in the preparation of unit dosage forms. Such compositions comprise a prophylactically or therapeutically effective amount of a prophylactic and/or therapeutic agent disclosed herein or a combination of those agents and a pharmaceutically acceptable carrier. Preferably, the disclosed compositions include a prophylactically or therapeutically effective amount of antibody or fusion protein and a pharmaceutically acceptable carrier.

In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant (e.g., Freund's adjuvant (complete and incomplete), excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like.

Generally, the ingredients of compositions are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The compositions can be formulated as neutral or salt forms. Pharmaceutically acceptable salts include, but are not limited to, those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

H. Kits

One embodiment provides a pharmaceutical pack or kit comprising one or more containers filled with antibody or fusion protein. Additionally, one or more other prophylactic or therapeutic agents useful for the treatment of a disease can also be included in the pharmaceutical pack or kit. One embodiment provides a pharmaceutical pack or kit including one or more containers filled with one or more of the ingredients of the pharmaceutical compositions. Optionally associated with such container(s) can be a notice in the form prescribed by a governmental agency regulating the manufacture, use or sale of pharmaceuticals or biological products, which notice reflects approval by the agency of manufacture, use or sale for human administration.

The present invention provides kits that can be used in the above methods. In one embodiment, a kit comprises one or more antibodies or fusion proteins. In another embodiment, a kit further comprises one or more other prophylactic or therapeutic agents useful for the treatment of cancer, in one or more containers. In another embodiment, a kit further comprises one or more cytotoxic antibodies that bind one or more cancer antigens associated with cancer. In certain embodiments, the other prophylactic or therapeutic agent is a chemotherapeutic. In other embodiments, the prophylactic or therapeutic agent is a biological or hormonal therapeutic.

I. Diagnostic Methods

The B7-H5 antibodies and their antigen-binding fragments can be used for diagnostic purposes, such as to detect, diagnose, or monitor diseases, disorders or infections associated with B7-H5 expression. The invention provides for the detection or diagnosis of a disease, disorder or infection, particularly an autoimmune disease comprising: (a) assaying the expression of B7-H5 in cells or in a tissue sample of a subject using one or more antibodies (or fragments thereof) that immunospecifically bind to such antigens; and (b) comparing the level of the antigen with a control level, e.g., levels in normal tissue samples, whereby an increase or decrease in the assayed level of antigen compared to the control level of the antigen is indicative of the disease, disorder or infection. Such antibodies and fragments are preferably employed in immunoassays, such as the enzyme linked immunosorbent assay (ELISA), the radioimmunoassay (RIA) and fluorescence-activated cell sorting (FACS).

One embodiment relates to the use of such antibodies and fragments, and particularly such antibodies and fragments that bind to human B7-H5, as reagents for IHC analysis in cells of an in vitro or in situ tissue sample or in vivo. Thus, the antibodies and fragments of the present invention have utility in the detection and diagnosis of a disease, disorder, or infection in a human. In one embodiment, such diagnosis comprises: a) administering to a subject (for example, parenterally, subcutaneously, or intraperitoneally) an effective amount of a labeled antibody or antigen-binding fragment that immunospecifically binds to B7-H5; b) waiting for a time interval following the administration for permitting the labeled molecule to preferentially concentrate at sites in the subject where B7-H5 is expressed (and for unbound labeled molecule to be cleared to background level); c) determining background level; and d) detecting the labeled antibody in the subject, such that detection of labeled antibody above the background level indicates that the subject has the disease, disorder, or infection. In accordance with this embodiment, the antibody is labeled with an imaging moiety which is detectable using an imaging system known to one of skill in the art. Background level can be determined by various methods including, comparing the amount of labeled molecule detected to a standard value previously determined for a particular system.

It will be understood in the art that the size of the subject and the imaging system used will determine the quantity of imaging moiety needed to produce diagnostic images. In vivo tumor imaging is described in S. W. Burchiel et al., "*Immunopharmacokinetics of Radiolabeled Antibodies and Their Fragments*," (Chapter 13 in TUMOR IMAGING: THE RADIOCHEMICAL DETECTION OF CANCER, S. W. Burchiel and B. A. Rhodes, eds., Masson Publishing Inc. (1982).

Depending on several variables, including the type of label used and the mode of administration, the time interval following the administration for permitting the labeled molecule to preferentially concentrate at sites in the subject and for unbound labeled molecule to be cleared to background level is 6 to 48 hours or 6 to 24 hours or 6 to 12 hours. In another embodiment the time interval following administration is 5 to 20 days or 5 to 10 days.

In one embodiment, monitoring of a disease, disorder or infection is carried out by repeating the method for diagnosing the disease, disorder or infection, for example, one month after initial diagnosis, six months after initial diagnosis, one year after initial diagnosis, etc.

Presence of the labeled molecule can be detected in the subject using methods known in the art for in vivo scanning. These methods depend upon the type of label used. Skilled artisans will be able to determine the appropriate method for detecting a particular label. Methods and devices that may be used in the disclosed diagnostic methods include, but are not limited to, computed tomography (CT), whole body scan such as position emission tomography (PET), magnetic resonance imaging (MRI), and sonography.

In a specific embodiment, the molecule is labeled with a radioisotope and is detected in the patient using a radiation responsive surgical instrument (Thurston et al., U.S. Pat. No. 5,441,050). In another embodiment, the molecule is labeled with a fluorescent compound and is detected in the patient using a fluorescence responsive scanning instrument. In another embodiment, the molecule is labeled with a positron emitting metal and is detected in the patient using positron emission-tomography. In yet another embodiment, the molecule is labeled with a paramagnetic label and is detected in a patient using magnetic resonance imaging (MRI).

Having now generally described the invention, the same will be more readily understood through reference to the following examples, which are provided by way of illustration and are not intended to be limiting of the present invention unless specified.

Example 1

Isolation and Characterization of Anti-Human B7-H5 Antibodies

Figure 4A:
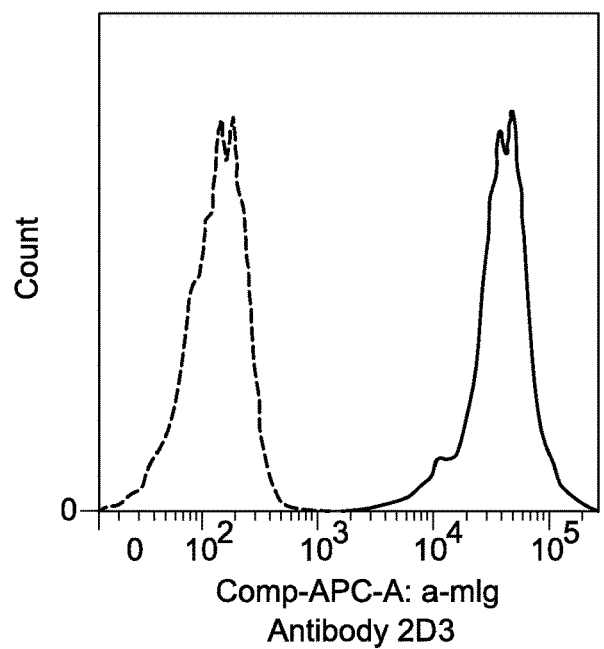
FIGS. 4A-4B show the ability of the antibodies produced by clones 2D3 and 18C3 to bind human B7-H5 expressed by a CHO transfectants.
Figure 4B:
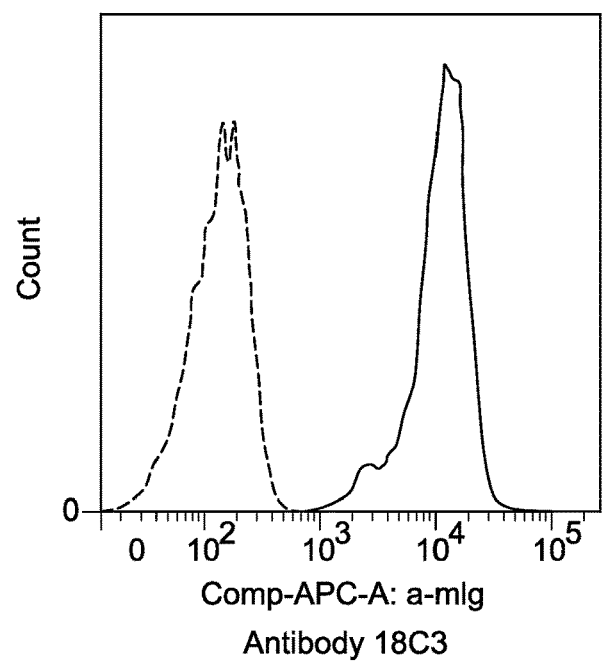

Anti-human B7-H5 antibodies were obtained by immunizing hamsters with B7-H5, and isolating hybridomas that express B7-H5-immunoreactive antibodies. Antibody-producing clones 2D3 and 18C3 were isolated. FIGS. 4A-4B show the ability of the antibodies produced by clones 2D3 and 18C3 to bind human B7-H5 expressed by a CHO transfectants.

The ability of the isolated antibodies to block B7-H5:CD28H interaction was determined by incubating the human B7-H5-expressing CHO transfectants in the presence of such antibodies and increasing concentrations of CD28H Ig (SEQ ID NO:20) and anti-human Ig PE.

Figure 5A:
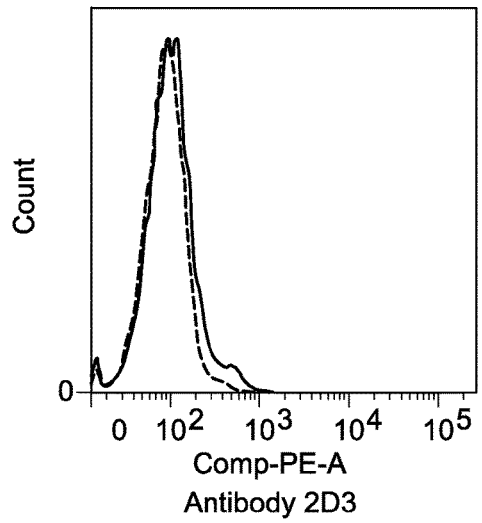
FIGS. 5A-5C show the abilities of the isolated antibodies and control Ig to block the B7-H5:CD28H interaction.
Figure 5B:
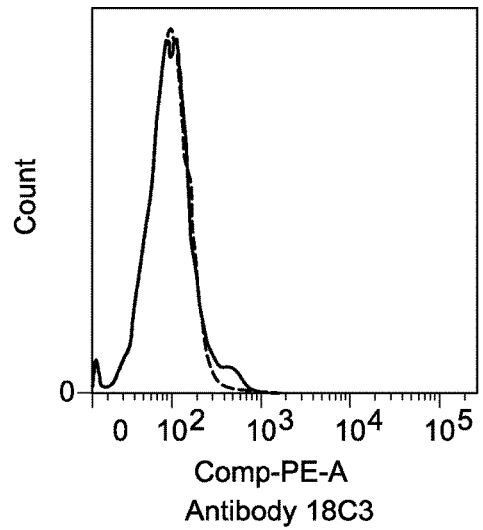
Figure 5C:
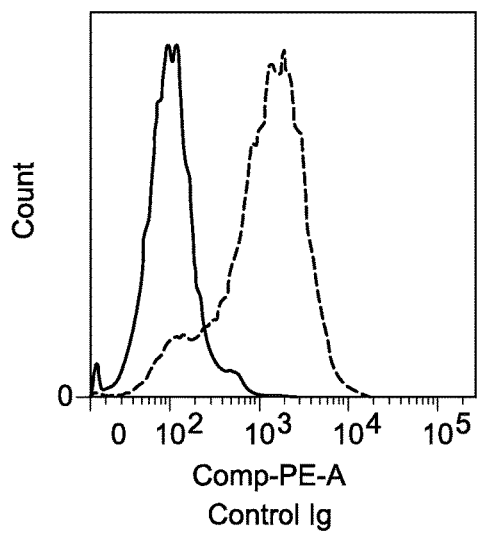

In such an experiment, cells incubated in the presence of non-blocking antibodies are capable of binding the CD28H Ig (seen as a second migration peak) (FIGS. 5A-5B). Antibodies 2D3 and 18C3 were found to block the B7-H5:CD28H interaction.

Figure 6:
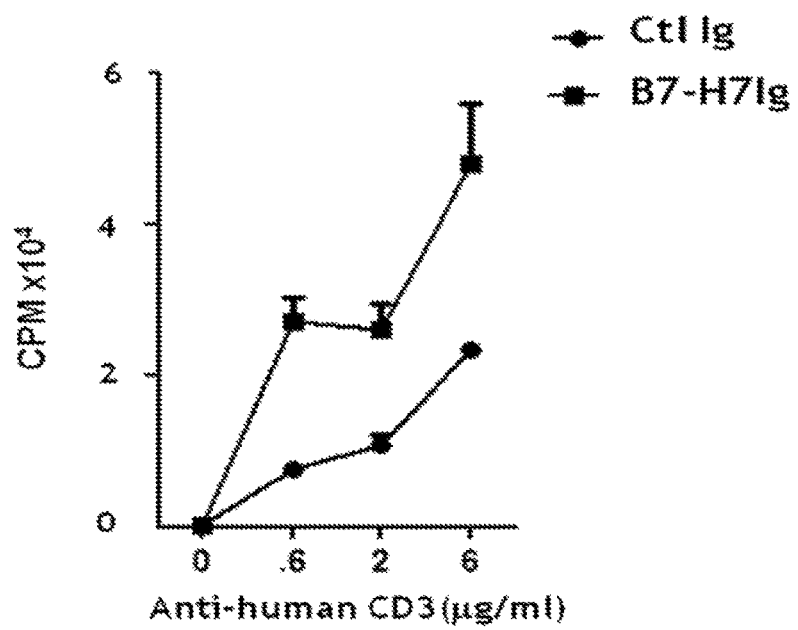
FIG. 6 shows the ability of a B7-H5 Ig fusion to stimulate a T cell response.

An anti-B7-H5 antibody of the present invention (2D3) was tested for its ability to block the B7-H5:CD28H interaction. A B7-H5 Ig fusion was prepared and found to be capable of binding to CD28H and of thereby stimulating a T cell response (FIG. 6). The fusion protein is the extracellular domain of B7-H5 (SEQ ID NO:26)

IFPLAFFIYVPMNEQIVIGRLDEDIILPSSFFRGSEVVIHWKYQDSYKVH

SYYKGSDHLESQDPRYANRTSLFYNEIQNGNASLFERRVSLLDEGIYTCY

VGTAIQVITNKVVLKVGVFLTPVMKYEKRNTNSFLICSVLSVYPRPIITW

KMDNTPISENNMEETGSLDSFSINSPLNITGSNSSYECTIENSLLKQTWT

GRWTMKDGLHKMQSEHVSLSCQPVNDYFSPNQDFKVTWSRMKSGTFSVLA

YYLSSSQNTIINESRFSWNKELINQSDFSMNLMDLNLSDSGEYLCNISSD

EYTLLTIHTVHVEPSQET fused to a murine IgG2a sequence.
An IgG2a sequence can be (SEQ ID NO:27)

EPRGPTIKPCPPCKCPAPNLLGGPSVFIFPPKIKDVLMISLSPIVTCVVV

DVSEDDPDVQISWFVNNVEVHTAQTQTHREDYNSTLRVVSALPIQHQDWM

SGKEFKCKVNNKDLPAPIERTISKPKGSVRAPQVYVLPPPEEEMTKKQVT

LTCMVTDFMPEDIYVEWTNNGKTELNYKNTEPVLDSDGSYFMYSKLRVEK

KNWVERNSYSCSVVHEGLHNHHTTKSFSRTPGK mIgG2a does not require the S→P modification (discussed in more detail below and as shown in SEQ ID NO:20) to stabilize the Fab arm or deletion of the C-terminal Lys. Fusion proteins can also be made with other Ig sequences, for example, human IgG4. For human IgG4 it can be preferred to include the S→P modification and/or deletion of the final Lys residue, as illustrated in the exemplary hIgG4 proteins discussed above.

The fusion protein was expressed from a vector encoding the CD33 signal peptide (not the native signal peptide).

Figure 7:
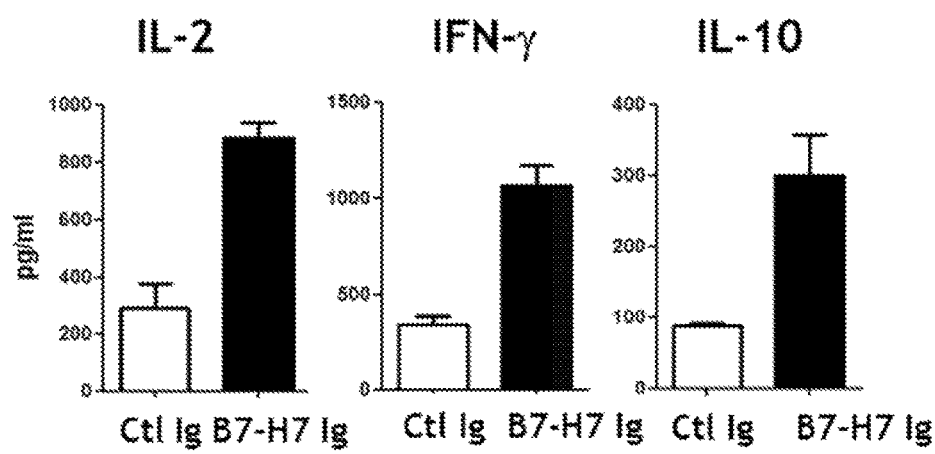
FIG. 7 shows the ability of the B7-H5 Ig to induce the expression of cytokines: IL-2, IFN-γ and IL-10.
Figure 8:
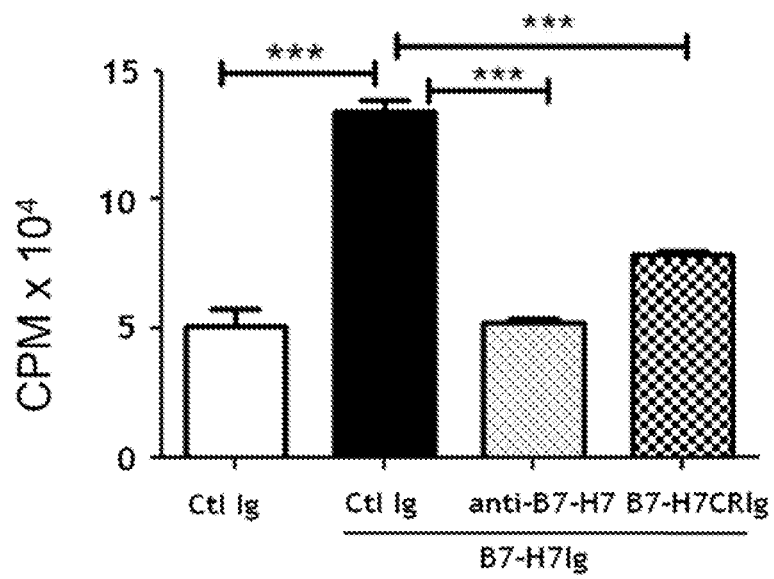
FIG. 8 shows that the anti-B7-H5 antibody 2D3 of the present invention is capable of binding to B7-H5 so as to block the capacity of B7-H5 to interact with its CD28H counter-receptor.
Figure 9:
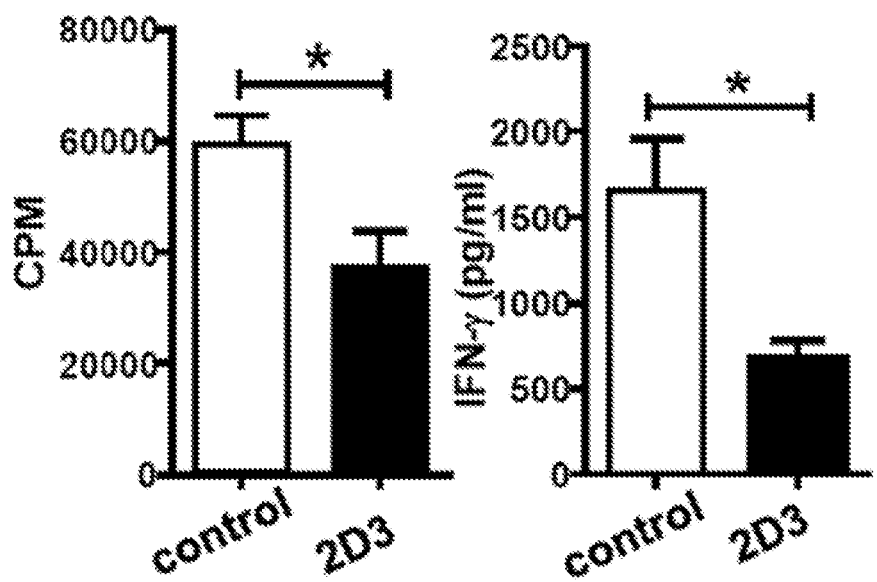
FIG. 9 shows the ability of anti-B7-H5 antibody 2D3 to inhibit an allogeneic T cell response.

FIG. 7 shows the ability of the B7-H5 Ig to induce the expression of cytokines (IL-2, IFN-γ and IL-10), thereby confirming the ability of the molecule to stimulate the immune system. The provision of the anti-B7-H5 antibody 2D3 inhibited such stimulation (FIG. 8). The antibody was also found to be capable of inhibiting an allogeneic T cell response (FIG. 9). These results indicate that those antibodies of the present invention that are capable of binding to B7-H5 so as to block the capacity of B7-H5 to interact with its CD28H counter-receptor are capable of mediating a physiological reduction in immune system activation.

Example 2

Anti-Human B7-H5 Antibodies Reduce the Percentage of Activated T Cells In Vivo

In order to investigate the in vivo effect of the anti-human B7-H5 antibodies, 20 million peripheral blood mononuclear cells (PBMCs) were injected into the peritoneal cavity of NOD scid IL2 receptor gamma chain knockout (NSG) mice (see, e.g., Toms, E. et al. (Epub 2012 Oct. 31) "A New Mouse Model For The Study Of Human Breast Cancer Metastasis," PLoS One 7(10):e47995; Misharin, A. V. et al. (2012) "*Development Of A New Humanized Mouse Model To Study Acute Inflammatory Arthritis,*" J. Transl. Med. 10:190; Waldron-Lynch, F. et al. (Epub 2012 Aug. 17) "*Analysis Of Human Biologics With A Mouse Skin Transplant Model In Humanized Mice,*" Amer. J. Transplant. 12(10):2652-2662; Volk, A. et al. (2012) "*Comparison Of Three Humanized Mouse Models For Adoptive T Cell Transfer,*" J. Gene Med. 14(8):540-548; Racki, W. J. et al. (2010) "*NOD-scid IL2rgamma(null) Mouse Model Of Human Skin Transplantation And Allograft Rejection,*" Transplantation 89(5):527-536). Phosphate buffered saline (PBS) or anti-human B7-H5 antibody (2D3) was injected into the tail vein of the animals and the percentage of CD28H+ cells among CD45RO+ cells was determined.

Figure 10A:
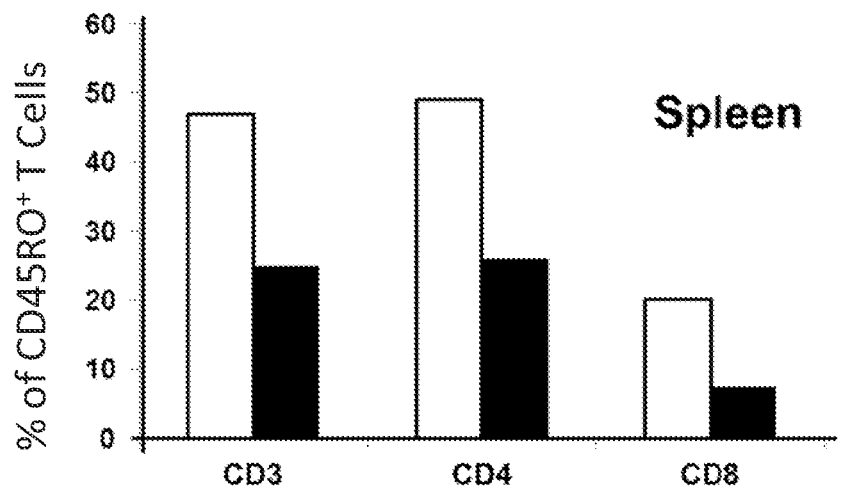
FIG. 10A and FIG. 10B show the effect of anti-human B7-H5 antibody on the percentage of CD28H$^+$ cells among activated (CD45RO$^+$) human T cells in the spleen (FIG. 10A) and peripheral blood (FIG. 10B) in NSG mice implanted with human PBMC.
Figure 10B:
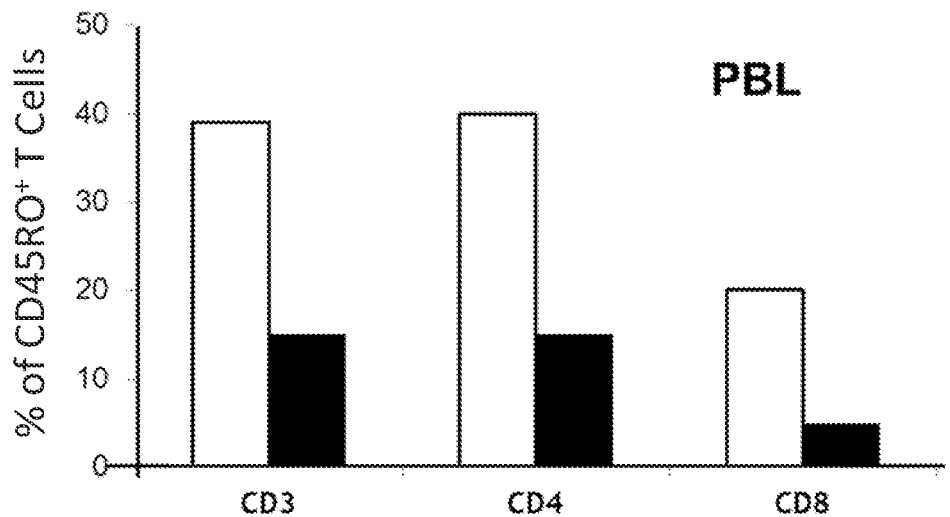
Figure 11A:
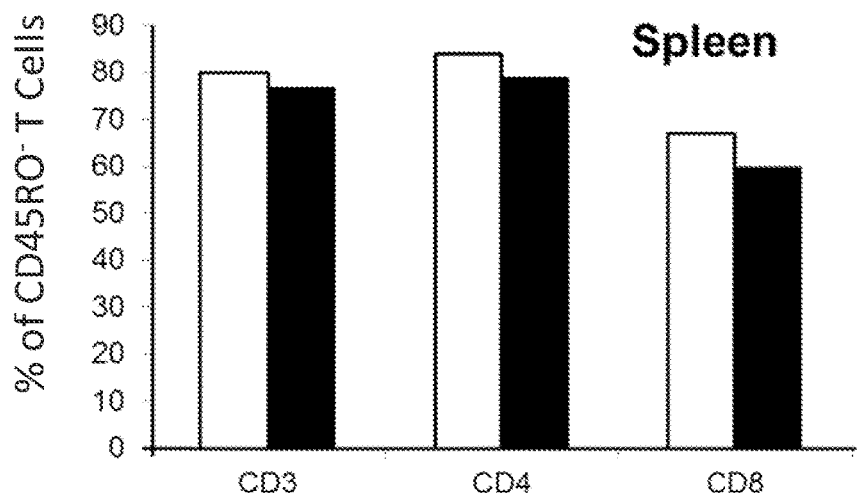
FIG. 11A and FIG. 11B show the effect of anti-human B7-H5 antibody on the percentage of CD28H$^+$ cells among naïve (CD45RO$^-$) human T cells in the spleen (FIG. 11A) and peripheral blood (FIG. 11B) in NSG mice implanted with human PBMC.
Figure 11B:
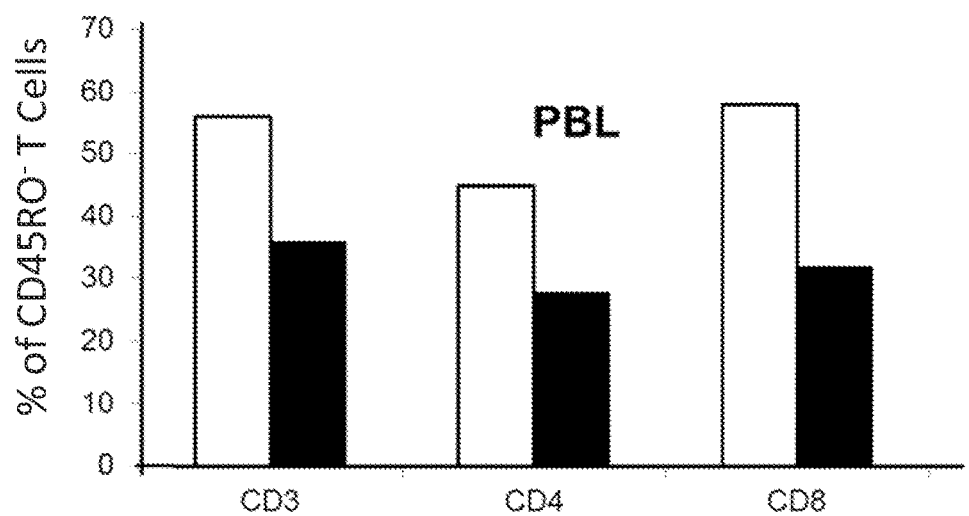

As shown in FIG. 10A and FIG. 10B, the percentage of CD28H+ cells among activated (CD45RO+) human T cells in the spleen (FIG. 10A) and peripheral blood (FIG. 10B) was reduced upon treatment with the anti-human B7-H5 antibody. Treatment with B7-H5 antibodies thus reduces the percentage of activated T cells in vivo. In contrast, such treatment had only a limited effect on naïve (CD45RO−) T cell populations (FIG. 11A and FIG. 11B).

Example 3

Recombinant Anti-Human B7-H5 Antibodies Retain Antigen Specificity

IgG4 antibodies have unique structural and functional properties and undergo "half-antibody exchange" in vivo, resulting in recombined antibodies composed of two different binding specificities (Nirula, A. et al. (2011) *"What Is Igg4? A Review Of The Biology Of A Unique Immunoglobulin Subtype,"* Curr. Opin. Rheumatol. 23(1): 119-124; Aalberse, R. C. et al. (2009) *"Immunoglobulin G4: An Odd Antibody,"* Clin. Exp. Allergy 39(4):469-477). Ser228 is mutated to Pro to stabilize the arm. A chimeric hIgG4P does not do "half-antibody exchange".

Figure 12A:
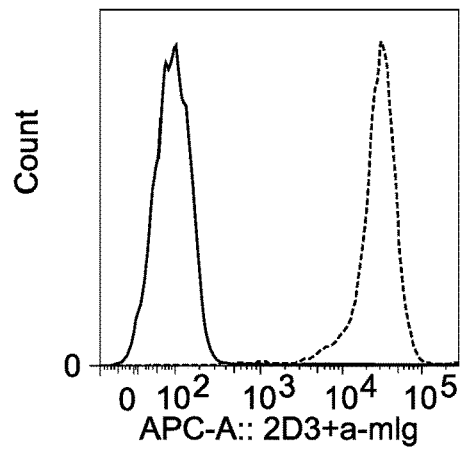
FIGS. 12A-12C show binding properties of recombinant anti-human B7-H5 chimeric antibodies (2D3 and 18C3).
Figure 12B:
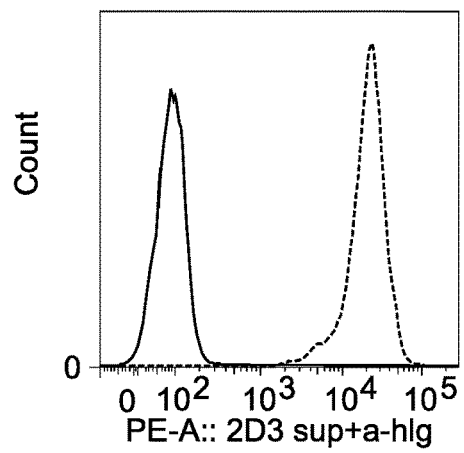
Figure 12C:
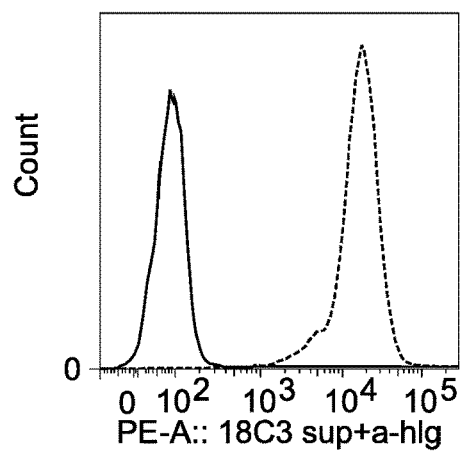
Figure 13:
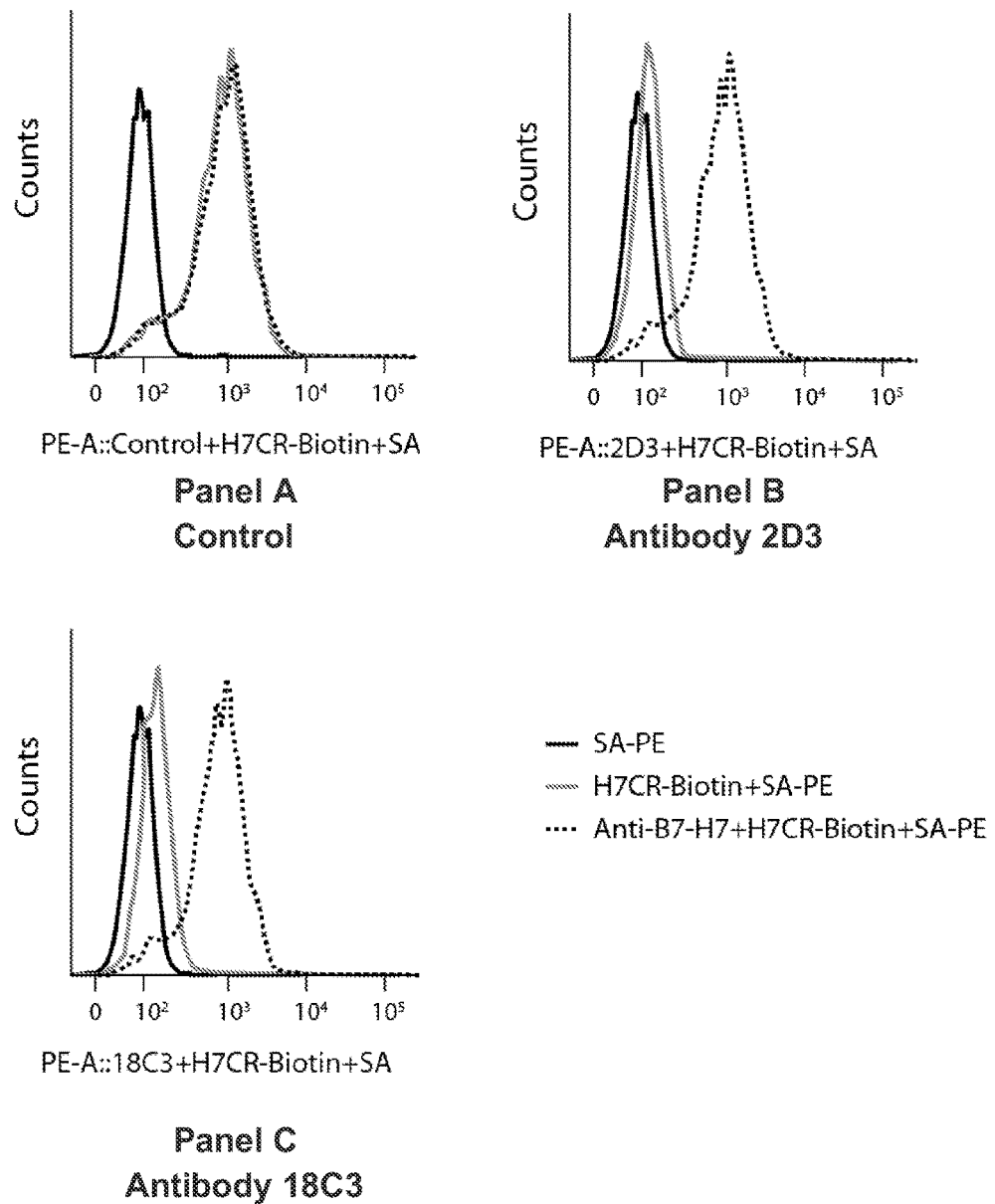
FIG. 13 (Panels A-C) shows the ability of recombinant anti-human B7-H5 chimeric antibodies (2D3 and 18C3) to completely block the binding of CD28H fusion protein to CHO B7-H5 transfectants. Human B7-H5 FL CHO transfectants were pre-incubated with control supernatant (Panel A) or recombinant chimeric 2D3 (Panel B) and 18C3 supernatants (Panel C), and subsequently stained with biotinylated CD28HhIg fusion protein.
Figure 14A:
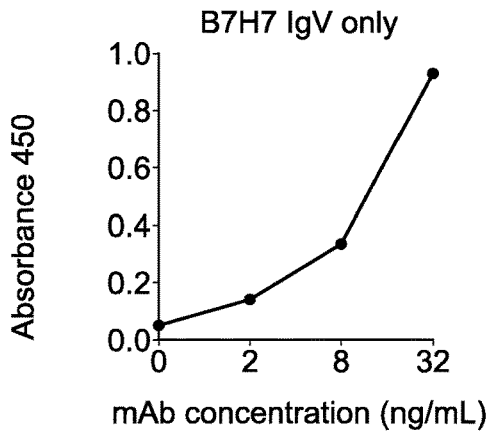
FIGS. 14A-14B show the epitope recognition site of anti-human B7-H5 antibodies (2D3 and 18C3).
Figure 14B:
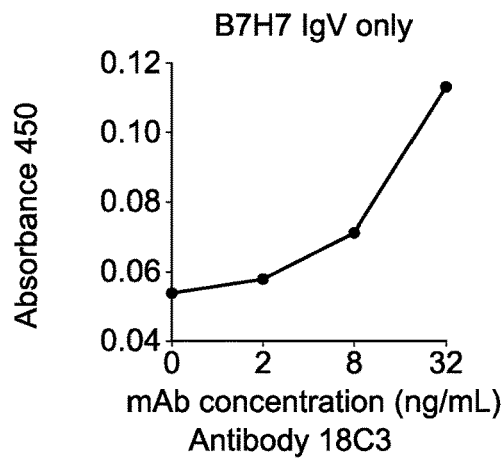
Figure 14C:
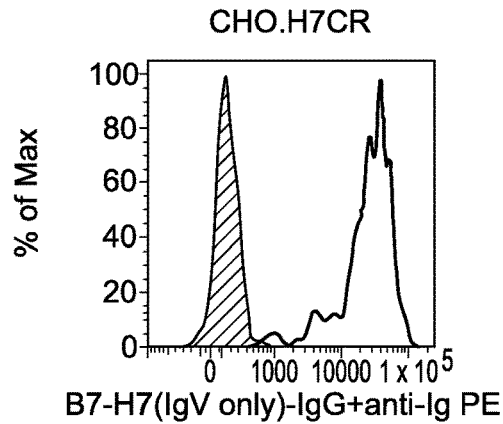
FIG. 14C shows B7-H5 IgV domain mediates B7-H5's interaction with CD28H.
Figure 15:
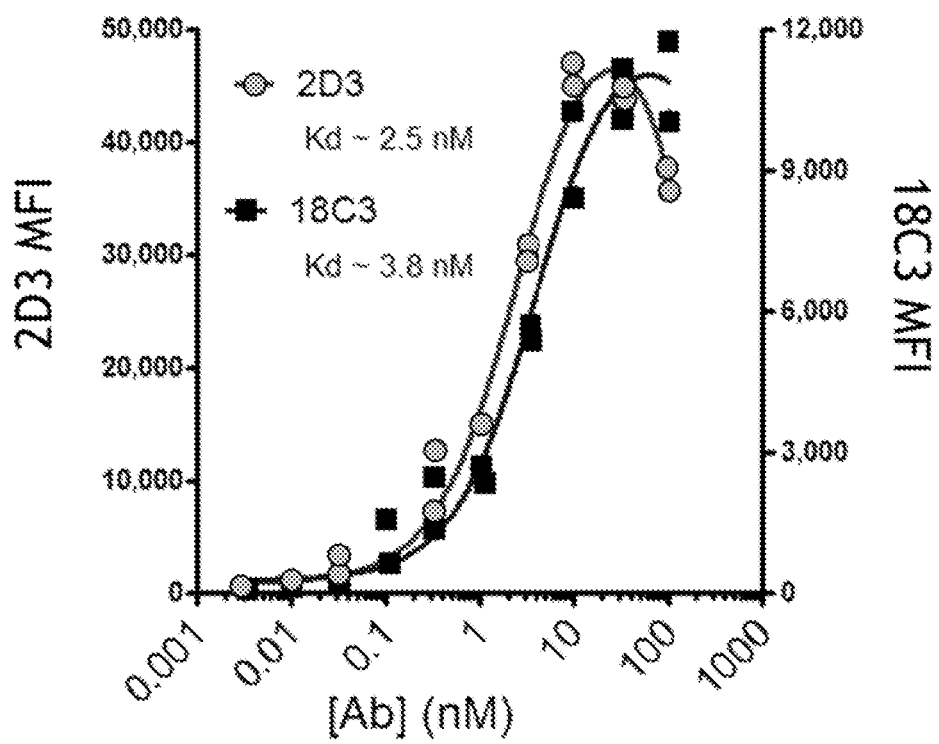
FIG. 15 compares the affinities of antibodies 2D3 and 18C3 for binding to human B7-H5 as expressed on the surface of CHO cells.

The human B7-H5-binding antibodies of the present invention (antibodies 2D3 and 18C3) were recombinantly converted to a human IgG4P isotype from their native hamster isotype. CHO transfectants that express human B7-H5 were then incubated in the presence of the recombinant antibodies. As shown in FIGS. 12A-C, both human IgG4P derivative antibodies were found to retain their immunospecific binding ability toward human B7-H5 and blocking capability disrupting the B7-H5-CD28H interaction (FIG. 13, Panels A-C). FIGS. 14A-14B show that antibodies 2D3 and 18C3 recognize the first IgV domain of B7-H5, which mediates B7-H5's interaction with CD28H (FIG. 14C). FIG. 15 compares the affinities of antibodies 2D3 and 18C3 for binding to human B7-H5 as expressed on the surface of CHO cells.

Example 4

Blockade of B7-H5:CD28H Interaction Inhibits Tetanus Toxoid (TT)-Specific T Cell Response In order to determine the effect of the B7-H5:CD28H interaction on the recall of memory-specific T cells, NSG mice reconstituted with human PBMCs plus autologous dendritic cells were immunized with a tetanus toxoid ("TT") vaccine. At the same day, mice were treated with control Ig, or anti-human B7-H5 antibody 2D3. Seven days later, cells in the peritoneal cavity were harvested, and re-stimulated with the TT antigen. T cell division was analyzed by BrdU incorporation. Cytokines in the culture supernatant were examined by a human Th1/Th2 CBA kit.

Figure 16B:
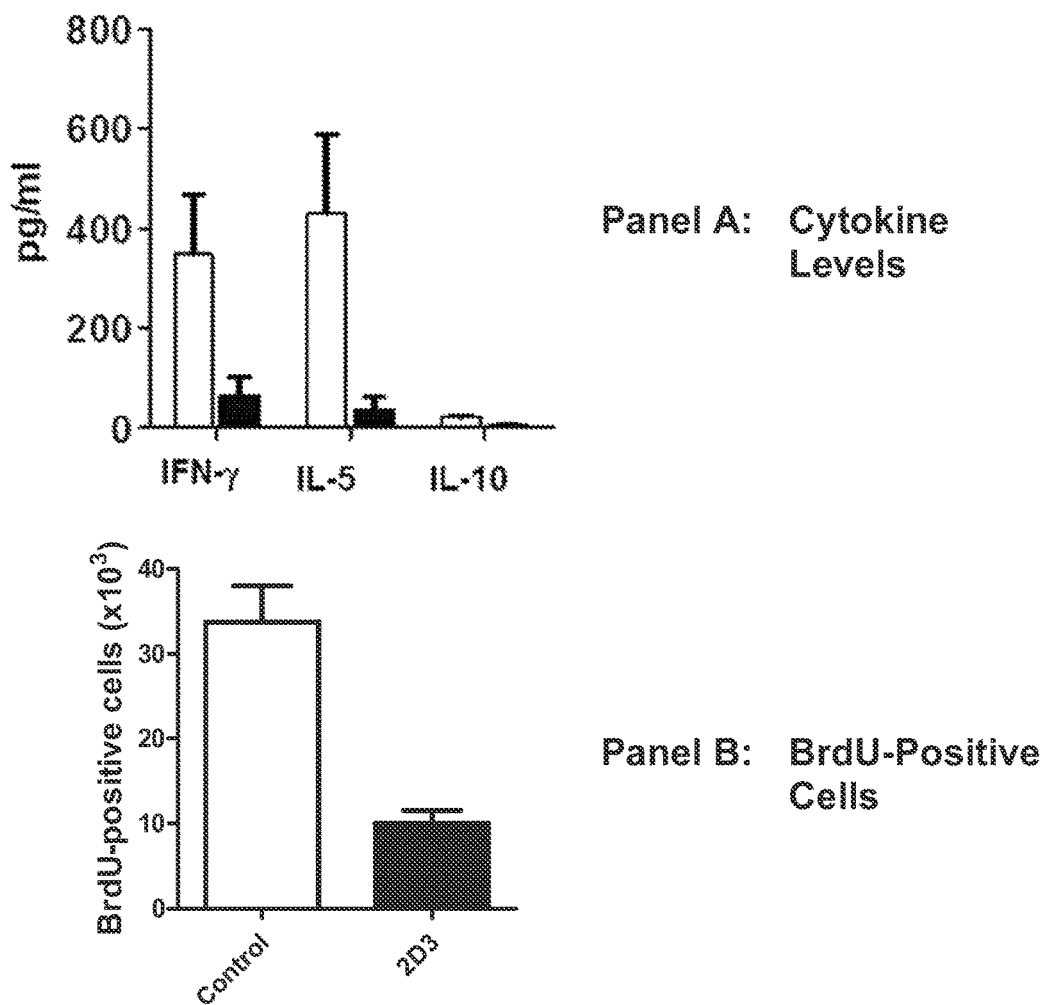

The results of such investigations are shown in FIGS. 16A-16B. As shown in these Figures, the endogenous B7-H5:CD28H interaction appears to be important for the recall of TT-specific memory T cells because injection of the mice with B7-H5 blocking mAb 2D3 significantly inhibited TT vaccine-elicited T cell proliferation, as indicated by BrdU incorporation (FIG. 16A, Panels A-B). As a result, cytokines in the culture supernatant including IFN-γ, IL-5 and IL-10 were all substantially reduced by the 2D3 mAb (FIG. 16B, Panels A-B). Taken together, the results indicate that the B7-H5:CD28H interaction plays an important role in the recall of memory T cells.

Example 5

Blockade of B7-H5:CD28H Interaction Inhibits Allogeneic T Cell Response

In order to determine the effect of the B7-H5:CD28H interaction on the allogeneic response in vivo, humanized NSG mice were challenged with allogeneic human macrophages. On the same day, each mouse was inoculated with control or 2D3 mAb. On day 7, splenocytes were harvested and allogeneic CD4 and CD8 T cell proliferations were evaluated by Ki-67 expression by intracellular staining.

The results of such investigations are shown in FIG. 17. As shown in FIG. 17, the endogenous B7-H5:CD28H interaction appears to be important for the allogeneic T cell response because injection of the mice with B7-H5 blocking mAb 2D3 significantly inhibited both CD8+(FIG. 17A) and CD4+(FIG. 17B) T cell proliferation, as indicated by Ki-67 expression.

Example 6

Blockade of B7-H5:CD28H Interaction Inhibits AKT Activation in Human T Cells

Figure 18:
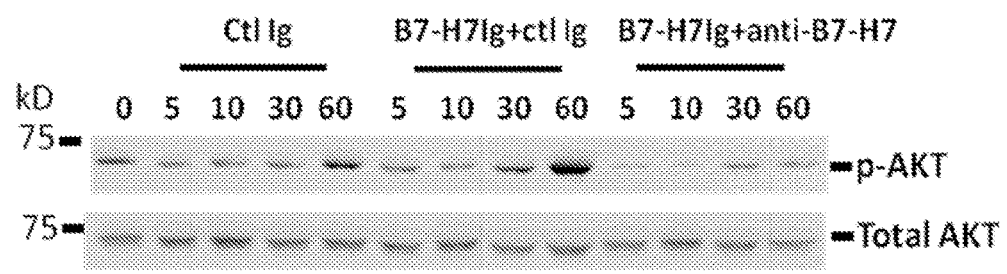
FIG. 18 shows simultaneous cross-linking of TCR and B7-H5 fusion protein induced AKT phosphorylation 30 min after stimulation, while TCR cross-linking alone induced minimal AKT phosphorylation. Importantly, inclusion of B7-H5 antibody 2D3 prevented AKT activation, indicating B7-H5 co-stimulation utilizes the AKT pathway to promote T cell response.

The results of such investigations are shown in FIG. 18. As shown in FIG. 18, the endogenous B7-H5:CD28H interaction appears to be important for AKT pathway activation in the presence of TCR signal. Simultaneous Cross-linking of TCR and B7-H5 fusion protein induced AKT phosphorylation 30 min after stimulation, while TCR cross-linking alone induced minimal AKT phosphorylation. Inclusion of B7-H5 blocking antibody 2D3 prevented AKT activation, indicating B7-H5 blockade could block T cell AKT pathway activation.

Example 7

Figure 19:
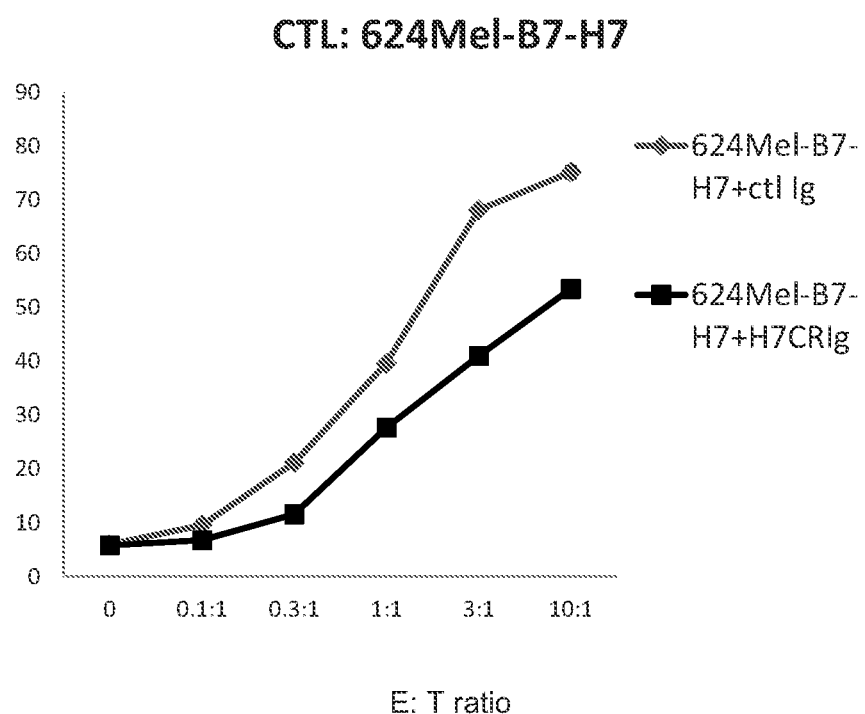
FIG. 19 shows B7-H5-CD28H pathway blockade by decoy receptor fusion protein CD28HIg suppressed the cytotoxic killing activity of allogeneic CD8 T cell against B7-H5 transfected 624Mel melanoma cell line, indicating B7-H5-CD28H pathway promotes cytotoxic killing activity of CD8 T cells on target cells.

Blockade of B7-H5:CD28H Interaction Suppress Cytotoxic T Lymphocyte Killing Against Tumor Cells The results of such investigations are shown in FIG. 19. As shown in FIG. 19, the interaction of tumor associated B7-H5 to cytotoxic T cell expressed CD28H costimulates the cytotoxic killing activity, as the blockade of B7-H5-CD28H pathway by decoy receptor fusion protein inhibits the CTL killing at several effector to target (E:T) ratio conditions.

Example 8

Blockade of B7-H5:CD28H Interaction Suppress Natural Killer Cell Activation

Figure 20A:
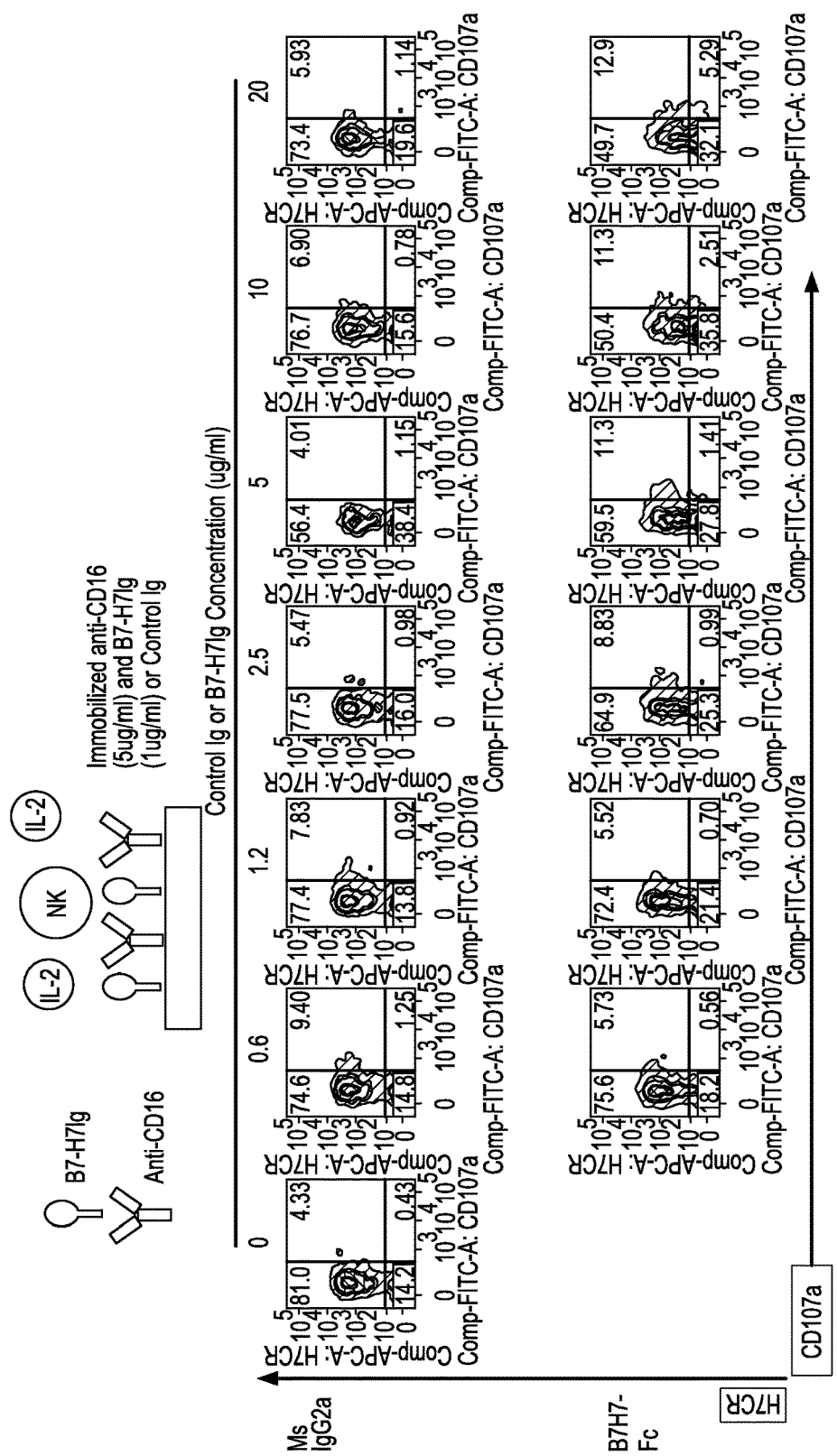
FIG. 20A-B show simultaneous cross-linking of CD16 and B7-H5 fusion protein on Natural Killer cells (NK) in the presence of soluble recombinant human IL-2 induced NK activation and degranulation (CD107a surface upregulation), whereas CD16 engagement alone did not induce significant NK degranulation. A B7-H5 fusion protein dose dependent NK activation was observed (FIG. 20A). Importantly, inclusion of B7-H5 antibody 2D3 prevented NK activation (FIG. 20B), indicating B7-H5 co-stimulates NK activation.
Figure 20B:
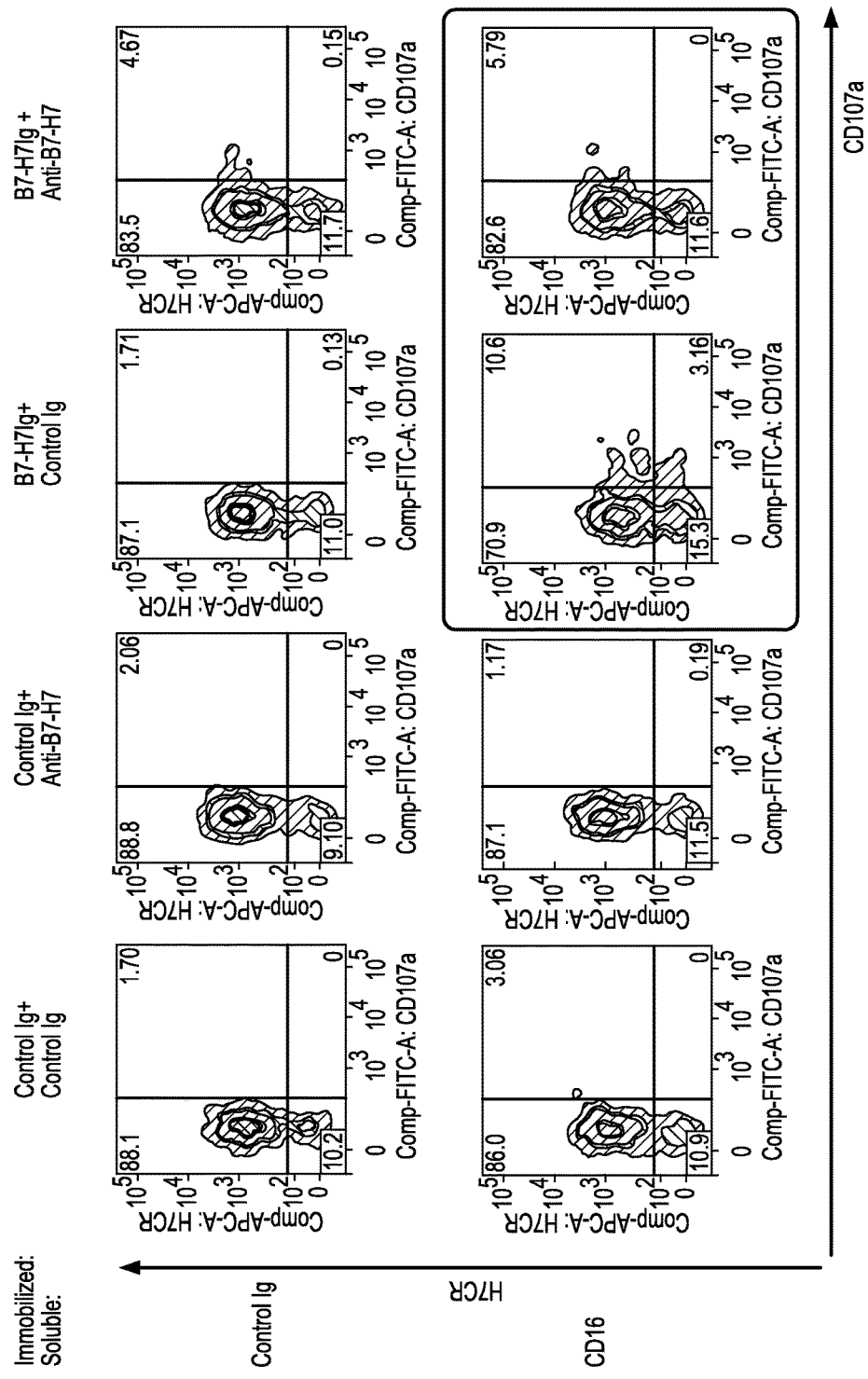

The results of such investigations are shown in FIG. 20A-B. As shown in FIG. 20A, simultaneous cross-linking of CD16 and B7-H5 fusion protein on Natural Killer cells (NK) in the presence of soluble recombinant human IL-2 induced NK activation and degranulation (CD107a surface upregulation), whereas CD16 engagement alone did not induce significant NK degranulation. B7-H5-CD28H pathway blockade by B7-H5 antibody 2D3 suppressed NK degranulation (FIG. 20B), indicating B7-H5 co-stimulates NK activation.

All publications and patents mentioned in this specification are herein incorporated by reference to the same extent as if each individual publication or patent application was specifically and individually indicated to be incorporated by reference in its entirety. While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth.

We claim:

1. An antibody or antigen binding fragment thereof comprising six complementarity determining regions (CDRs), wherein the CDRs comprise
   (1) the three light chain CDRs of SEQ ID NO: 11 and the three heavy chain CDRs of SEQ ID NO: 9, or
   (2) the three light chain CDRs of SEQ ID NO: 15 and the three heavy chain CDRs of SEQ ID NO: 13, and
   wherein the antibody or antigen binding fragment thereof binds to human B7-H5 as set forth in SEQ ID NO: 1.

2. The antibody or antigen binding fragment thereof of claim 1, wherein the three light chain CDRs comprise a first light chain CDR comprising amino acids 27-38 of SEQ ID NO: 11, a second light chain CDR comprising amino acids 56-58 of SEQ ID NO: 11, and a third light chain CDR comprising amino acids 95-102 of SEQ ID NO: 11;
   wherein the three heavy chain CDRs comprise a first heavy chain CDR comprising amino acids 26-33 of SEQ ID NO: 9, a second heavy chain CDR comprising amino acids 51-58 of SEQ ID NO: 9, and a third heavy chain CDR comprising amino acids 97-106 of SEQ ID NO: 9;
   wherein the three light chain CDRs comprise a first light chain CDR comprising amino acids 27-38 of SEQ ID NO: 15, a second light chain CDR comprising amino acids 56-58 of SEQ ID NO: 15, and a third light chain CDR comprising amino acids 95-102 of SEQ ID NO: 15; or
   wherein the three heavy chain CDRs comprise a first heavy chain CDR comprising amino acids 26-33 of SEQ ID NO: 13, a second heavy chain CDR comprising amino acids 51-58 of SEQ ID NO: 13, and a third heavy chain CDR comprising amino acids 97-106 of SEQ ID NO: 13.

3. The antibody or antigen binding fragment thereof of claim 1 comprising a light chain variable region comprising the amino acid sequence of SEQ ID NO: 11 and a heavy chain variable region comprising the amino acid sequence of SEQ ID NO: 9; or comprising a light chain variable region comprising the amino acid sequence of SEQ ID NO: 15 and a heavy chain variable region comprising the amino acid sequence of SEQ ID NO: 13.

4. The antibody or antigen binding fragment thereof of claim 1, wherein the bound B7-H5 is arrayed on the surface of a live cell or expressed at an endogenous or transfected concentration.

5. The antibody or antigen binding fragment thereof of claim 1, wherein the antibody or antigen binding fragment thereof
   (A) attenuates the ability of B7-H5 to bind to CD28H;
   (B) antagonizes signal transduction that occurs as a consequence of B7-H5 binding to CD28H;
   (C) inhibits an allogeneic T cell response;
   (D) a combination thereof.

6. The antibody or antigen binding fragment thereof of claim 1, wherein the antibody or antigen binding fragment thereof is detectably labeled or comprises a conjugated toxin, drug, receptor, enzyme, or receptor ligand.

7. A humanized antibody or antigen binding fragment thereof comprising one or more human IgG4 constant domains and
   a light chain variable region comprising the amino acid sequence of SEQ ID NO: 11, a heavy chain variable region comprising the amino acid sequence of SEQ ID NO: 9, or
   a light chain variable region comprising the amino acid sequence of SEQ ID NO: 15, a heavy chain variable region comprising the amino acid sequence of SEQ ID NO: 13.

8. A pharmaceutical composition comprising the antibody or an antigen binding fragment thereof of claim 1, and a physiologically acceptable carrier or excipient.

9. A method of down-modulating the immune system of a subject who has an autoimmune or inflammatory disease, or has received or will receive a transplant, the method comprising administering the pharmaceutical composition of claim 8 in an effective amount to down-modulate the subject's immune system via binding of the antibody or an antigen binding fragment thereof to human B7-H5.

10. The method of claim 9, wherein the subject has is an autoimmune disease.

11. The method of claim 9, wherein the subject has is an inflammatory disease.

12. The method of claim 9, wherein the subject has received or will receive a transplant.

* * * * *

UNITED STATES PATENT AND TRADEMARK OFFICE
CERTIFICATE OF CORRECTION

PATENT NO. : 10,316,092 B2
APPLICATION NO. : 14/893463
DATED : June 11, 2019
INVENTOR(S) : Yao et al.

It is certified that error appears in the above-identified patent and that said Letters Patent is hereby corrected as shown below:

In the Specification

Column 1, Line 15-22, Replace the first paragraph as follows:
STATEMENT OF GOVERNMENTAL INTEREST
This invention was made with government support under CA097085, AI072592 and CA113341 awarded by the National Institutes of Health. The government has certain rights in the invention.

Signed and Sealed this
Sixth Day of July, 2021

Drew Hirshfeld
*Performing the Functions and Duties of the*
*Under Secretary of Commerce for Intellectual Property and*
*Director of the United States Patent and Trademark Office*

SEQUENCE LISTING

<160> NUMBER OF SEQ ID NOS: 29

<210> SEQ ID NO 1
<211> LENGTH: 414
<212> TYPE: PRT
<213> ORGANISM: Homo sapiens

<400> SEQUENCE: 1

```
Met Lys Ala Gln Thr Ala Leu Ser Phe Phe Leu Ile Leu Ile Thr Ser
1               5                   10                  15

Leu Ser Gly Ser Gln Gly Ile Phe Pro Leu Ala Phe Phe Ile Tyr Val
            20                  25                  30

Pro Met Asn Glu Gln Ile Val Ile Gly Arg Leu Asp Glu Asp Ile Ile
        35                  40                  45

Leu Pro Ser Ser Phe Glu Arg Gly Ser Glu Val Val Ile His Trp Lys
    50                  55                  60

Tyr Gln Asp Ser Tyr Lys Val His Ser Tyr Tyr Lys Gly Ser Asp His
65                  70                  75                  80

Leu Glu Ser Gln Asp Pro Arg Tyr Ala Asn Arg Thr Ser Leu Phe Tyr
                85                  90                  95

Asn Glu Ile Gln Asn Gly Asn Ala Ser Leu Phe Phe Arg Arg Val Ser
            100                 105                 110

Leu Leu Asp Glu Gly Ile Tyr Thr Cys Tyr Val Gly Thr Ala Ile Gln
        115                 120                 125

Val Ile Thr Asn Lys Val Val Leu Lys Val Gly Val Phe Leu Thr Pro
130                 135                 140

Val Met Lys Tyr Glu Lys Arg Asn Thr Asn Ser Phe Leu Ile Cys Ser
145                 150                 155                 160

Val Leu Ser Val Tyr Pro Arg Pro Ile Ile Thr Trp Lys Met Asp Asn
                165                 170                 175

Thr Pro Ile Ser Glu Asn Asn Met Glu Glu Thr Gly Ser Leu Asp Ser
            180                 185                 190

Phe Ser Ile Asn Ser Pro Leu Asn Ile Thr Gly Ser Asn Ser Ser Tyr
        195                 200                 205

Glu Cys Thr Ile Glu Asn Ser Leu Leu Lys Gln Thr Trp Thr Gly Arg
    210                 215                 220

Trp Thr Met Lys Asp Gly Leu His Lys Met Gln Ser Glu His Val Ser
225                 230                 235                 240

Leu Ser Cys Gln Pro Val Asn Asp Tyr Phe Ser Pro Asn Gln Asp Phe
                245                 250                 255

Lys Val Thr Trp Ser Arg Met Lys Ser Gly Thr Phe Ser Val Leu Ala
            260                 265                 270

Tyr Tyr Leu Ser Ser Ser Gln Asn Thr Ile Ile Asn Glu Ser Arg Phe
        275                 280                 285

Ser Trp Asn Lys Glu Leu Ile Asn Gln Ser Asp Phe Ser Met Asn Leu
    290                 295                 300

Met Asp Leu Asn Leu Ser Asp Ser Gly Glu Tyr Leu Cys Asn Ile Ser
305                 310                 315                 320

Ser Asp Glu Tyr Thr Leu Leu Thr Ile His Thr Val His Val Glu Pro
                325                 330                 335

Ser Gln Glu Thr Ala Ser His Asn Lys Gly Leu Trp Ile Leu Val Pro
            340                 345                 350

Ser Ala Ile Leu Ala Ala Phe Leu Leu Ile Trp Ser Val Lys Cys Cys
        355                 360                 365
```

```
Arg Ala Gln Leu Glu Ala Arg Arg Ser Arg His Pro Ala Asp Gly Ala
        370                 375                 380
Gln Gln Glu Arg Cys Cys Val Pro Pro Gly Arg Cys Pro Ser Ala
385                 390                 395                 400
Pro Asp Asn Gly Glu Glu Asn Val Pro Leu Ser Gly Lys Val
                405                 410
```

<210> SEQ ID NO 2
<211> LENGTH: 1242
<212> TYPE: DNA
<213> ORGANISM: Artificial Sequence
<220> FEATURE:
<223> OTHER INFORMATION: Synthetic Polynucleotide - human B7-H5 cDNA

<400> SEQUENCE: 2

```
atgaaggcac agacagcact gtctttcttc ctcattctca taacatctct gagtggatct      60
caaggcatat tccctttggc tttcttcatt tatgttccta tgaatgaaca aatcgtcatt     120
ggaagacttg atgaagatat aattctccct tcttcatttg agaggggatc cgaagtcgta     180
atacactgga agtatcaaga tagctataag gttcatagtt actacaaagg cagtgaccat     240
ttggaaagcc aagatcccag atatgcaaac aggacatccc ttttctataa tgagattcaa     300
aatgggaatg cgtcactatt tttcagaaga gtaagccttc tggacgaagg aatttacacc     360
tgctatgtag aacagcaat tcaagtgatt acaaacaaag tggtgctaaa ggtgggagtt     420
tttctcacac ccgtgatgaa gtatgaaaag aggaacacaa acagcttctt aatatgcagc     480
gtgttaagtg tttatcctcg tccaattatc acgtggaaaa tggacaacac acctatctct     540
gaaaacaaca tggaagaaac agggtctttg gattcttttt ctattaacag cccactgaat     600
attacaggat caaattcatc ttatgaatgt acaattgaaa attcactgct gaagcaaaca     660
tggacagggc gctggacgat gaaagatggc cttcataaaa tgcaaagtga acacgtttca     720
ctctcatgtc aacctgtaaa tgattatttt tcaccaaacc aagacttcaa agttacttgg     780
tccagaatga aaagtgggac tttctctgtc ctggcttact atctgagctc ctcacaaaat     840
acaattatca tgaatcccg attctcatgg aacaaagagc tgataaacca gagtgacttc     900
tctatgaatt tgatggatct taatctttca gacagtgggg aatatttatg caatatttct     960
tcggatgaat atactttact taccatccac acagtgcatg tagaaccgag ccaagaaaca    1020
gcttcccata caaaggctt atggattttg gtgccctctg cgattttggc agcttttctg    1080
ctgatttgga gcgtaaaatg ttgcagagcc agctagaag ccaggaggag cagacaccct    1140
gctgatggag cccaacaaga aagatgttgt gtccctcctg gtgagcgctg tcccagtgca    1200
cccgataatg gcgaagaaaa tgtgcctctt tcaggaaaag ta                      1242
```

<210> SEQ ID NO 3
<211> LENGTH: 356
<212> TYPE: PRT
<213> ORGANISM: Artificial Sequence
<220> FEATURE:
<223> OTHER INFORMATION: Synthetic Polypeptide - B7-H5 fusion protein

<400> SEQUENCE: 3

```
Ile Phe Pro Leu Ala Phe Phe Ile Tyr Val Pro Met Asn Glu Gln Ile
1                5                  10                  15

Val Ile Gly Arg Leu Asp Glu Asp Ile Ile Leu Pro Ser Ser Phe Glu
            20                  25                  30

Arg Gly Ser Glu Val Val Ile His Trp Lys Tyr Gln Asp Ser Tyr Lys
        35                  40                  45
```

Val His Ser Tyr Tyr Lys Gly Ser Asp His Leu Glu Ser Gln Asp Pro
    50                  55                  60

Arg Tyr Ala Asn Arg Thr Ser Leu Phe Tyr Asn Glu Ile Gln Asn Gly
65                  70                  75                  80

Asn Ala Ser Leu Phe Phe Arg Arg Val Ser Leu Leu Asp Glu Gly Ile
                85                  90                  95

Tyr Thr Cys Tyr Val Gly Thr Ala Ile Gln Val Ile Thr Asn Lys Val
            100                 105                 110

Val Leu Lys Val Gly Val Phe Leu Thr Pro Val Met Lys Tyr Glu Lys
        115                 120                 125

Glu Ser Lys Tyr Gly Pro Pro Cys Pro Pro Cys Pro Ala Pro Glu Phe
    130                 135                 140

Leu Gly Gly Pro Ser Val Phe Leu Phe Pro Pro Lys Pro Lys Asp Thr
145                 150                 155                 160

Leu Met Ile Ser Arg Thr Pro Glu Val Thr Cys Val Val Val Asp Val
                165                 170                 175

Ser Gln Glu Asp Pro Glu Val Gln Phe Asn Trp Tyr Val Asp Gly Val
            180                 185                 190

Glu Val His Asn Ala Lys Thr Lys Pro Arg Glu Glu Gln Phe Asn Ser
        195                 200                 205

Thr Tyr Arg Val Val Ser Val Leu Thr Val Leu His Gln Asp Trp Leu
    210                 215                 220

Asn Gly Lys Glu Tyr Lys Cys Lys Val Ser Asn Lys Gly Leu Pro Ser
225                 230                 235                 240

Ser Ile Glu Lys Thr Ile Ser Lys Ala Lys Gly Gln Pro Arg Glu Pro
                245                 250                 255

Gln Val Tyr Thr Leu Pro Pro Ser Gln Glu Glu Met Thr Lys Asn Gln
            260                 265                 270

Val Ser Leu Thr Cys Leu Val Lys Gly Phe Tyr Pro Ser Asp Ile Ala
        275                 280                 285

Val Glu Trp Glu Ser Asn Gly Gln Pro Glu Asn Asn Tyr Lys Thr Thr
    290                 295                 300

Pro Pro Val Leu Asp Ser Asp Gly Ser Phe Phe Leu Tyr Ser Arg Leu
305                 310                 315                 320

Thr Val Asp Lys Ser Arg Trp Gln Glu Gly Asn Val Phe Ser Cys Ser
                325                 330                 335

Val Met His Glu Ala Leu His Asn His Tyr Thr Gln Lys Ser Leu Ser
            340                 345                 350

Leu Ser Pro Gly
        355

<210> SEQ ID NO 4
<211> LENGTH: 22
<212> TYPE: PRT
<213> ORGANISM: Artificial Sequence
<220> FEATURE:
<223> OTHER INFORMATION: Synthetic Polypeptide - signal sequence

<400> SEQUENCE: 4

Met Lys Ala Gln Thr Ala Leu Ser Phe Phe Leu Ile Leu Ile Thr Ser
1               5                   10                  15

Leu Ser Gly Ser Gln Gly
            20

<210> SEQ ID NO 5

```
<211> LENGTH: 66
<212> TYPE: DNA
<213> ORGANISM: Artificial Sequence
<220> FEATURE:
<223> OTHER INFORMATION: Synthetic Polynucleotide - nucleic acid
      encoding a signal sequence

<400> SEQUENCE: 5
atgaaggccc agaccgccct gtccttcttc ctgatcctga tcacctccct gtccggcagc    60
caggga                                                               66

<210> SEQ ID NO 6
<211> LENGTH: 1068
<212> TYPE: DNA
<213> ORGANISM: Artificial Sequence
<220> FEATURE:
<223> OTHER INFORMATION: Synthetic Polynucleotide - Sequence encoding a
      fusion protein

<400> SEQUENCE: 6
atcttccctc tggccttctt catctacgtg cccatgaacg agcagatcgt gatcggccgg    60
ctggacgagg atattatcct gccctccagc ttcgagcggg gctccgaggt cgtgatccac   120
tggaagtacc aggactccta caaggtgcac tcctactaca agggctccga ccacctggaa   180
tcccaggacc ccagatacgc caaccggacc agcctgttct acaacgagat ccagaacggc   240
aacgcctccc tgttcttccg cgagtgtccc tgctggatg agggcatcta cacctgttac   300
gtgggcaccg ccatccaagt gatcaccaac aaggtggtgc tgaaagtggg cgtgttcctg   360 accccgtga tgaagtacga aagagtct aagtacggcc ctccctgccc ccttgtcct    420 gccctgaat ttctgggcgg accctctgtg ttcctgttcc ccccaaagcc caggacacc    480 ctgatgatct cccggacccc cgaagtgacc tgcgtggtgg tggatgtgtc ccaggaagat   540
cccgaggtgc agttcaattg gtacgtggac ggcgtggaag tgcacaacgc caagaccaag   600
cccagagagg aacagttcaa ctccacctac cgggtggtgt ccgtgctgac cgtgctgcac   660
caggattggc tgaacggcaa agagtacaag tgcaaggtgt ccaacaaggg cctgcccagc   720
tccatcgaaa agaccatctc caaggccaag ggccagcccc gggaaccca ggtgtacaca   780 ctgcctccaa gccaggaaga gatgaccaag aaccaggtgt ccctgacctg tctcgtgaag   840
ggcttctacc cctccgatat cgccgtggaa tgggagtcca acggccagcc tgagaacaac   900
tacaagacca ccccccctgt gctggactcc gacggctctt tcttcctgta ctcccgcctg   960
accgtggaca gtccagatg gcaggaaggc aacgtgttct cctgctccgt gatgcacgag  1020
gccctgcaca accactacac ccagaagtcc ctgtccctga gccccggc               1068

<210> SEQ ID NO 7
<211> LENGTH: 282
<212> TYPE: PRT
<213> ORGANISM: Homo sapiens

<400> SEQUENCE: 7

Met Gly Ser Pro Gly Met Val Leu Gly Leu Leu Val Gln Ile Trp Ala
1               5                   10                  15

Leu Gln Glu Ala Ser Ser Leu Ser Val Gln Gln Gly Pro Asn Leu Leu
            20                  25                  30

Gln Val Arg Gln Gly Ser Gln Ala Thr Leu Val Cys Gln Val Asp Gln
        35                  40                  45

Ala Thr Ala Trp Glu Arg Leu Arg Val Lys Trp Thr Lys Asp Gly Ala
    50                  55                  60
```

Ile Leu Cys Gln Pro Tyr Ile Thr Asn Gly Ser Leu Ser Leu Gly Val
65                  70                  75                  80

Cys Gly Pro Gln Gly Arg Leu Ser Trp Gln Ala Pro Ser His Leu Thr
                85                  90                  95

Leu Gln Leu Asp Pro Val Ser Leu Asn His Ser Gly Ala Tyr Val Cys
            100                 105                 110

Trp Ala Ala Val Glu Ile Pro Glu Leu Glu Glu Ala Glu Gly Asn Ile
            115                 120                 125

Thr Arg Leu Phe Val Asp Pro Asp Pro Thr Gln Asn Arg Asn Arg
            130                 135             140

Ile Ala Ser Phe Pro Gly Phe Leu Phe Val Leu Leu Gly Val Gly Ser
145                 150                 155                 160

Met Gly Val Ala Ala Ile Val Trp Gly Ala Trp Phe Trp Gly Arg Arg
                165                 170                 175

Ser Cys Gln Gln Arg Asp Ser Gly Asn Ser Pro Gly Asn Ala Phe Tyr
                180                 185                 190

Ser Asn Val Leu Tyr Arg Pro Arg Gly Ala Pro Lys Lys Ser Glu Asp
                195                 200                 205

Cys Ser Gly Glu Gly Lys Asp Gln Arg Gly Gln Ser Ile Tyr Ser Thr
210                 215                 220

Ser Phe Pro Gln Pro Ala Pro Arg Gln Pro His Leu Ala Ser Arg Pro
225                 230                 235                 240

Cys Pro Ser Pro Arg Pro Cys Pro Ser Pro Arg Pro Gly His Pro Val
                245                 250                 255

Ser Met Val Arg Val Ser Pro Arg Pro Ser Pro Thr Gln Gln Pro Arg
                260                 265                 270

Pro Lys Gly Phe Pro Lys Val Gly Glu Glu
                275                 280

<210> SEQ ID NO 8
<211> LENGTH: 846
<212> TYPE: DNA
<213> ORGANISM: Artificial Sequence
<220> FEATURE:
<223> OTHER INFORMATION: Synthetic Polynucleotide - cDNA encoding human
      CD28H

<400> SEQUENCE: 8

```
atggggtccc cgggcatggt gctgggcctc ctggtgcaga tctgggccct gcaagaagcc      60
tcaagcctga gcgtgcagca ggggcccaac ttgctgcagg tgaggcaggg cagtcaggcg     120
accctggtct gccaggtgga ccaggccaca gcctgggaac ggctccgtgt taagtggaca     180
aaggatgggg ccatcctgtg tcaaccgtac atcaccaacg gcagcctcag cctgggggtc     240
tgcgggcccc agggacggct ctcctggcag gcacccagcc atctcaccct gcagctggac     300
cctgtgagcc tcaaccacag cggggcgtac gtgtgctggg cggccgtaga gattcctgag     360
ttggaggagg ctgagggcaa cataacaagg ctctttgtgg acccagatga ccccacacag     420
aacagaaacc ggatcgcaag cttcccagga ttcctcttcg tgctgctggg ggtgggaagc     480
atgggtgtgg ctgcgatcgt gtggggtgcc tggttctggg gccgcgcag ctgccagcaa      540 agggactcag gtaacagccc aggaaatgca ttctacagca acgtcctata ccggccccgg     600
ggggccccaa agaagagtga ggactgctct ggagagggga aggaccagag ggccagagc      660 atttattcaa cctccttccc gcaaccggcc cccgccagc cgcacctggc gtcaagaccc      720
tgccccagcc cgagaccctg cccagccc aggcccggcc acccgtctc tatggtcagg        780
```
gtctctccta gaccaagccc cacccagcag ccgaggccaa aagggttccc caaagtggga    840
gaggag                                                              846

<210> SEQ ID NO 9
<211> LENGTH: 117
<212> TYPE: PRT
<213> ORGANISM: Artificial Sequence
<220> FEATURE:
<223> OTHER INFORMATION: Synthetic Polynucleotide - Heavy Chain Variable
      Region Anti-Human B7-H5 Clone 2D3

<400> SEQUENCE: 9

Gln Val Gln Leu Gln Gln Ser Gly Ala Glu Leu Val Lys Pro Gly Ala
1               5                   10                  15

Ser Val Lys Leu Ser Cys Lys Ala Ser Gly Tyr Thr Phe Thr Ser His
            20                  25                  30

Asp Ile Asn Trp Val Arg Gln Arg Pro Glu Leu Gly Leu Glu Trp Ile
        35                  40                  45

Gly Trp Ile Phe Pro Gly Asp Gly Ser Thr Lys Phe Asn Glu Lys Phe
    50                  55                  60

Lys Gly Lys Ala Thr Leu Thr Thr Asp Lys Ser Ser Thr Ala Tyr
65                  70                  75                  80

Ile Gln Leu Ser Arg Leu Thr Ser Glu Asp Ser Ala Val Tyr Phe Cys
                85                  90                  95

Ala Arg Asn Ser Phe Tyr Ser Met Asp Tyr Trp Gly Gln Gly Thr Ser
            100                 105                 110

Val Thr Val Ser Ser
        115

<210> SEQ ID NO 10
<211> LENGTH: 351
<212> TYPE: DNA
<213> ORGANISM: Artificial Sequence
<220> FEATURE:
<223> OTHER INFORMATION: Synthetic Polynucleotide - Polynucleotide
      Encoding Heavy Chain Variable Region Anti-Human B7-H5 Clone 2D3

<400> SEQUENCE: 10
caggttcaac tgcaacagtc tggagctgaa ctggtaaagc ctggggcttc agtgaagttg    60
tcctgcaagg cttctggcta caccttcaca agccatgata taaactgggt gaggcagagg   120
cctgaactgg gacttgagtg gattggatgg attttttcctg gggatggtag tactaagttc   180
aatgagaagt tcaagggcaa ggccacactg actacagaca atcctccag cacagcctac    240 atacagctca gcaggctgac gtctgaggac tctgctgtct atttctgtgc aagaaactcc    300
ttctactcta tggactattg gggtcaagga acctcagtca ccgtctcctc a             351

<210> SEQ ID NO 11
<211> LENGTH: 112
<212> TYPE: PRT
<213> ORGANISM: Artificial Sequence
<220> FEATURE:
<223> OTHER INFORMATION: Synthetic Polypeptide - Light Chain Variable
      Region Anti-Human B7-H5 Clone 2D3

<400> SEQUENCE: 11

Asp Ile Val Met Ser Gln Ser Pro Ser Ser Leu Ala Val Ser Ala Gly
1               5                   10                  15

Glu Lys Val Thr Met Ser Cys Lys Ser Ser Gln Ser Leu Leu Asn Ser
            20                  25                  30

```
Arg Thr Arg Lys Asn Gln Leu Ala Trp Tyr Gln Gln Lys Pro Gly Gln
        35                  40                  45

Ser Pro Lys Leu Leu Ile Tyr Trp Ala Phe Ile Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Lys Gln
                85                  90                  95

Ser Tyr Asn Leu Arg Thr Phe Gly Gly Gly Thr Lys Leu Glu Ile Lys
            100                 105                 110

<210> SEQ ID NO 12
<211> LENGTH: 337
<212> TYPE: DNA
<213> ORGANISM: Artificial Sequence
<220> FEATURE:
<223> OTHER INFORMATION: Synthetic Polynucleotide - Polynucleotide
      Encoding Light Chain Variable Region Anti-Human B7-H5 Clone 2D3

<400> SEQUENCE: 12
gacattgtga tgtcacagtc tccatcctcc ctggctgtgt cagcaggaga gaaggtcact     60
atgagctgca atccagtca gagtctgctc aacagtagaa cccgaaagaa ccagttggct    120
tggtaccagc agaaaccagg acagtctcct aaattactga tctactgggc attcattagg    180
gaatctgggg tccctgatcg cttcacaggc agtggatctg gacagattt cactctcacc    240 atcagcagtg tgcaggctga agacctggca gtttattact gcaagcaatc ttataatctt    300
cggacgttcg gtggaggcac caagctggaa atcaaac                              337

<210> SEQ ID NO 13
<211> LENGTH: 117
<212> TYPE: PRT
<213> ORGANISM: Artificial Sequence
<220> FEATURE:
<223> OTHER INFORMATION: Synthetic Polypeptide - Heavy Chain Variable
      Region Anti-Human B7-H5 Clone 18C3

<400> SEQUENCE: 13

Gln Val Gln Leu Gln Gln Ser Gly Ala Glu Leu Val Lys Pro Gly Ala
1               5                   10                  15

Ser Val Lys Leu Ser Cys Lys Ala Ser Gly Tyr Thr Phe Thr Ser His
            20                  25                  30

Asp Ile Asn Trp Val Arg Gln Arg Pro Glu Gln Gly Leu Glu Trp Ile
        35                  40                  45

Gly Trp Ile Phe Pro Gly Asp Gly Ser Thr Lys Phe Asn Glu Lys Phe
    50                  55                  60

Lys Gly Lys Ala Thr Leu Thr Thr Asp Lys Ser Ser Thr Ala Tyr
65                  70                  75                  80

Ile Gln Leu Ser Arg Leu Thr Ser Glu Asp Ser Ala Val Tyr Phe Cys
                85                  90                  95

Ala Arg Asn Ser Phe Tyr Ser Met Asp Tyr Trp Gly Gln Gly Thr Ser
            100                 105                 110

Val Thr Val Ser Ser
        115

<210> SEQ ID NO 14
<211> LENGTH: 351
<212> TYPE: DNA
<213> ORGANISM: Artificial Sequence
```

```
<220> FEATURE:
<223> OTHER INFORMATION: Synthetic Polynucleotide - Polynucleotide
      Encoding Heavy Chain Variable Region Anti-Human B7-H5 Clone 18C3

<400> SEQUENCE: 14
caggttcaac tgcagcagtc tggagctgaa ctggtaaagc ctggggcttc agtgaagttg      60
tcctgcaagg cttctggcta caccttcaca agccatgata taaactgggt gaggcagagg     120
cctgaacagg gacttgagtg gattggatgg atttttcctg gggatggtag tactaagttc     180
aatgagaagt tcaagggcaa ggccacactg actacagaca atcctccag cacagcctac      240 atacagctca gcaggctgac atctgaggac tctgctgtct atttctgtgc aagaaactcc     300
ttctattcta tggactactg gggtcaagga acctcagtca ccgtctcctc a              351

<210> SEQ ID NO 15
<211> LENGTH: 112
<212> TYPE: PRT
<213> ORGANISM: Artificial Sequence
<220> FEATURE:
<223> OTHER INFORMATION: Synthetic Polypeptide - Light Chain Variable
      Region Anti-Human B7-H5 Clone 18C3

<400> SEQUENCE: 15

Asp Ile Val Met Ser Gln Ser Pro Ser Ser Leu Ala Val Ser Ala Gly
1               5                   10                  15

Glu Lys Val Thr Met Ser Cys Lys Ser Ser Gln Ser Leu Leu Asn Ser
            20                  25                  30

Arg Thr Arg Lys Asn Gln Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Lys Gln
                85                  90                  95

Ser Tyr Asn Leu Arg Thr Phe Gly Gly Gly Thr Lys Leu Glu Ile Lys
            100                 105                 110

<210> SEQ ID NO 16
<211> LENGTH: 4
<212> TYPE: PRT
<213> ORGANISM: Artificial Sequence
<220> FEATURE:
<223> OTHER INFORMATION: Synthetic Polypeptide - linker

<400> SEQUENCE: 16

Gly Ser Gly Ser
1

<210> SEQ ID NO 17
<211> LENGTH: 4
<212> TYPE: PRT
<213> ORGANISM: Artificial Sequence
<220> FEATURE:
<223> OTHER INFORMATION: Synthetic Polypeptide - Linker

<400> SEQUENCE: 17

Gly Gly Gly Ser
1

<210> SEQ ID NO 18
<211> LENGTH: 15
```

```
<212> TYPE: PRT
<213> ORGANISM: Artificial Sequence
<220> FEATURE:
<223> OTHER INFORMATION: Synthetic Polypeptide - linker

<400> SEQUENCE: 18

Gly Gly Gly Gly Ser Gly Gly Gly Gly Ser Gly Gly Gly Gly Ser
1               5                   10                  15

<210> SEQ ID NO 19
<211> LENGTH: 20
<212> TYPE: PRT
<213> ORGANISM: Artificial Sequence
<220> FEATURE:
<223> OTHER INFORMATION: Synthetic Polypeptide - Linker

<400> SEQUENCE: 19

Gly Gly Gly Gly Ser Gly Gly Gly Gly Ser Gly Gly Gly Gly Ser Gly
1               5                   10                  15

Gly Gly Gly Ser
            20

<210> SEQ ID NO 20
<211> LENGTH: 347
<212> TYPE: PRT
<213> ORGANISM: Artificial Sequence
<220> FEATURE:
<223> OTHER INFORMATION: Synthetic Polypeptide - CD28H-hIgG4 fusion
      protein

<400> SEQUENCE: 20

Leu Ser Val Gln Gln Gly Pro Asn Leu Leu Gln Val Arg Gln Gly Ser
1               5                   10                  15

Gln Ala Thr Leu Val Cys Gln Val Asp Gln Ala Thr Ala Trp Glu Arg
            20                  25                  30

Leu Arg Val Lys Trp Thr Lys Asp Gly Ala Ile Leu Cys Gln Pro Tyr
        35                  40                  45

Ile Thr Asn Gly Ser Leu Ser Leu Gly Val Cys Gly Pro Gln Gly Arg
    50                  55                  60

Leu Ser Trp Gln Ala Pro Ser His Leu Thr Leu Gln Leu Asp Pro Val
65                  70                  75                  80

Ser Leu Asn His Ser Gly Ala Tyr Val Cys Trp Ala Ala Val Glu Ile
                85                  90                  95

Pro Glu Leu Glu Glu Ala Glu Gly Asn Ile Thr Arg Leu Phe Val Asp
            100                 105                 110

Pro Asp Asp Pro Thr Gln Glu Ser Lys Tyr Gly Pro Pro Cys Pro Pro
        115                 120                 125

Cys Pro Ala Pro Glu Phe Leu Gly Gly Pro Ser Val Phe Leu Phe Pro
    130                 135                 140

Pro Lys Pro Lys Asp Thr Leu Met Ile Ser Arg Thr Pro Glu Val Thr
145                 150                 155                 160

Cys Val Val Val Asp Val Ser Gln Glu Asp Pro Glu Val Gln Phe Asn
                165                 170                 175

Trp Tyr Val Asp Gly Val Glu Val His Asn Ala Lys Thr Lys Pro Arg
            180                 185                 190

Glu Glu Gln Phe Asn Ser Thr Tyr Arg Val Val Ser Val Leu Thr Val
        195                 200                 205

Leu His Gln Asp Trp Leu Asn Gly Lys Glu Tyr Lys Cys Lys Val Ser
    210                 215                 220
```

-continued

Asn Lys Gly Leu Pro Ser Ser Ile Glu Lys Thr Ile Ser Lys Ala Lys
225                 230                 235                 240

Gly Gln Pro Arg Glu Pro Gln Val Tyr Thr Leu Pro Pro Ser Gln Glu
            245                 250                 255

Glu Met Thr Lys Asn Gln Val Ser Leu Thr Cys Leu Val Lys Gly Phe
        260                 265                 270

Tyr Pro Ser Asp Ile Ala Val Glu Trp Glu Ser Asn Gly Gln Pro Glu
            275                 280                 285

Asn Asn Tyr Lys Thr Thr Pro Pro Val Leu Asp Ser Asp Gly Ser Phe
290                 295                 300

Phe Leu Tyr Ser Arg Leu Thr Val Asp Lys Ser Arg Trp Gln Glu Gly
305                 310                 315                 320

Asn Val Phe Ser Cys Ser Val Met His Glu Ala Leu His Asn His Tyr
                325                 330                 335

Thr Gln Lys Ser Leu Ser Leu Ser Pro Gly Lys
            340                 345

<210> SEQ ID NO 21
<211> LENGTH: 20
<212> TYPE: PRT
<213> ORGANISM: Artificial Sequence
<220> FEATURE:
<223> OTHER INFORMATION: Synthetic Polypeptide - signal sequence

<400> SEQUENCE: 21

Met Ser Val Pro Thr Gln Val Leu Gly Leu Leu Leu Leu Trp Leu Thr
1               5                   10                  15

Asp Ala Arg Cys
            20

<210> SEQ ID NO 22
<211> LENGTH: 22
<212> TYPE: PRT
<213> ORGANISM: Artificial Sequence
<220> FEATURE:
<223> OTHER INFORMATION: Synthetic Polypeptide - signal sequence

<400> SEQUENCE: 22

Met Gly Ser Pro Gly Met Val Leu Gly Leu Leu Val Gln Ile Trp Ala
1               5                   10                  15

Leu Gln Glu Ala Ser Ser
            20

<210> SEQ ID NO 23
<211> LENGTH: 1104
<212> TYPE: DNA
<213> ORGANISM: Artificial Sequence
<220> FEATURE:
<223> OTHER INFORMATION: Synthetic Polynucleotide - Polynucleotide
      encoding a CD28H-Ig

<400> SEQUENCE: 23
atgtccgtgc ccacccaggt gctgggattg ctgctgctgt ggctgaccga cgccagatgc    60
ctgtctgtgc agcagggccc taacctgctg caagtgcggc agggctctca ggctacactc   120
gtgtgtcagg tggaccaggc caccgcctgg gagagactga gtgaagtga ccaaggac      180 ggcgccatcc tgtgccagcc ctacatcacc aacggctccc tgtccctggg cgtgtgtgga   240
cctcagggca gactgtcttg gcaggcccct ctcacctga cctgcagct ggaccctgtg     300 tccctgaatc actccggcgc ctacgtgtgt tgggccgctg tggaaatccc cgagctggaa   360

-continued

```
gaggccgagg gcaacatcac ccggctgttc gtggaccctg acgaccctac ccaggaatct    420
aagtacggcc ctccctgccc tccttgccca gccctgaat ttctgggcgg accctccgtg    480
ttcctgttcc ccccaaagcc caaggacacc ctgatgatct cccggacccc cgaagtgacc    540
tgcgtggtgg tggatgtgtc ccaggaagat cccgaggtgc agttcaattg gtacgtggac    600
ggcgtggaag tgcacaacgc caagaccaag cccagagagg aacagttcaa ctccacctac    660
cgggtggtgt ccgtgctgac cgtgctgcac caggattggc tgaacggcaa agagtacaag    720
tgcaaggtgt ccaacaaggg cctgcccagc tccatcgaaa agaccatctc caaggccaag    780
ggccagcccc gggaaccca ggtgtacaca ctgcctccaa gccaggaaga tgaccaag     840
aaccaggtgt cactgacctg tctcgtgaag ggcttctacc cctccgatat cgccgtggaa    900
tgggagtcca acggccagcc tgagaacaac tacaagacca ccccccctgt gctggactcc    960
gacggctcct tcttcctgta ctcccgcctg accgtggaca agtccagatg gcaggaaggc   1020
aacgtgttct cctgctccgt gatgcacgag gccctgcaca accactacac ccagaagtcc   1080
ctgagcctgt cccccggcaa gtga                                          1104
```

<210> SEQ ID NO 24
<211> LENGTH: 546
<212> TYPE: PRT
<213> ORGANISM: Artificial Sequence
<220> FEATURE:
<223> OTHER INFORMATION: Synthetic Polypeptide - B7-H5ECD-hIgG4P fusion
      protein

<400> SEQUENCE: 24

```
Ile Phe Pro Leu Ala Phe Phe Ile Tyr Val Pro Met Asn Glu Gln Ile
1               5                   10                  15

Val Ile Gly Arg Leu Asp Glu Asp Ile Ile Leu Pro Ser Ser Phe Glu
            20                  25                  30

Arg Gly Ser Glu Val Val Ile His Trp Lys Tyr Gln Asp Ser Tyr Lys
        35                  40                  45

Val His Ser Tyr Tyr Lys Gly Ser Asp His Leu Glu Ser Gln Asp Pro
    50                  55                  60

Arg Tyr Ala Asn Arg Thr Ser Leu Phe Tyr Asn Glu Ile Gln Asn Gly
65                  70                  75                  80

Asn Ala Ser Leu Phe Phe Arg Arg Val Ser Leu Leu Asp Glu Gly Ile
                85                  90                  95

Tyr Thr Cys Tyr Val Gly Thr Ala Ile Gln Val Ile Thr Asn Lys Val
            100                 105                 110

Val Leu Lys Val Gly Val Phe Leu Thr Pro Val Met Lys Tyr Glu Lys
        115                 120                 125

Arg Asn Thr Asn Ser Phe Leu Ile Cys Ser Val Leu Ser Val Tyr Pro
    130                 135                 140

Arg Pro Ile Ile Thr Trp Lys Met Asp Asn Thr Pro Ile Ser Glu Asn
145                 150                 155                 160

Asn Met Glu Glu Thr Gly Ser Leu Asp Ser Phe Ser Ile Asn Ser Pro
                165                 170                 175

Leu Asn Ile Thr Gly Ser Asn Ser Ser Tyr Glu Cys Thr Ile Glu Asn
            180                 185                 190

Ser Leu Leu Lys Gln Thr Trp Thr Gly Arg Trp Thr Met Lys Asp Gly
        195                 200                 205

Leu His Lys Met Gln Ser Glu His Val Ser Leu Ser Cys Gln Pro Val
    210                 215                 220
```

```
Asn Asp Tyr Phe Ser Pro Asn Gln Asp Phe Lys Val Thr Trp Ser Arg
225                 230                 235                 240

Met Lys Ser Gly Thr Phe Ser Val Leu Ala Tyr Tyr Leu Ser Ser
                245                 250                 255

Gln Asn Thr Ile Ile Asn Glu Ser Arg Phe Ser Trp Asn Lys Glu Leu
            260                 265                 270

Ile Asn Gln Ser Asp Phe Ser Met Asn Leu Met Asp Leu Asn Leu Ser
        275                 280                 285

Asp Ser Gly Glu Tyr Leu Cys Asn Ile Ser Ser Asp Glu Tyr Thr Leu
    290                 295                 300

Leu Thr Ile His Thr Val His Val Glu Pro Ser Gln Glu Thr Glu Ser
305                 310                 315                 320

Lys Tyr Gly Pro Pro Cys Pro Pro Cys Pro Ala Pro Glu Phe Leu Gly
                325                 330                 335

Gly Pro Ser Val Phe Leu Phe Pro Pro Lys Pro Lys Asp Thr Leu Met
            340                 345                 350

Ile Ser Arg Thr Pro Glu Val Thr Cys Val Val Val Asp Val Ser Gln
        355                 360                 365

Glu Asp Pro Glu Val Gln Phe Asn Trp Tyr Val Asp Gly Val Glu Val
370                 375                 380

His Asn Ala Lys Thr Lys Pro Arg Glu Glu Gln Phe Asn Ser Thr Tyr
385                 390                 395                 400

Arg Val Val Ser Val Leu Thr Val Leu His Gln Asp Trp Leu Asn Gly
                405                 410                 415

Lys Glu Tyr Lys Cys Lys Val Ser Asn Lys Gly Leu Pro Ser Ser Ile
            420                 425                 430

Glu Lys Thr Ile Ser Lys Ala Lys Gly Gln Pro Arg Glu Pro Gln Val
        435                 440                 445

Tyr Thr Leu Pro Pro Ser Gln Glu Glu Met Thr Lys Asn Gln Val Ser
    450                 455                 460

Leu Thr Cys Leu Val Lys Gly Phe Tyr Pro Ser Asp Ile Ala Val Glu
465                 470                 475                 480

Trp Glu Ser Asn Gly Gln Pro Glu Asn Asn Tyr Lys Thr Thr Pro Pro
                485                 490                 495

Val Leu Asp Ser Asp Gly Ser Phe Phe Leu Tyr Ser Arg Leu Thr Val
            500                 505                 510

Asp Lys Ser Arg Trp Gln Glu Gly Asn Val Phe Ser Cys Ser Val Met
        515                 520                 525

His Glu Ala Leu His Asn His Tyr Thr Gln Lys Ser Leu Ser Leu Ser
    530                 535                 540

Pro Gly
545

<210> SEQ ID NO 25
<211> LENGTH: 1707
<212> TYPE: PRT
<213> ORGANISM: Artificial Sequence
<220> FEATURE:
<223> OTHER INFORMATION: Synthetic Polynucleotide - Polynucleotide
      encoding a B7-H5ECD-hIgG4P

<400> SEQUENCE: 25

Ala Thr Gly Ala Ala Gly Gly Cys Cys Ala Gly Ala Cys Cys Gly
1               5                   10                  15

Cys Cys Cys Thr Gly Thr Cys Cys Thr Cys Thr Cys Thr Cys Cys Thr
            20                  25                  30
```

-continued

```
Gly Ala Thr Cys Cys Thr Gly Ala Thr Cys Ala Cys Cys Thr Cys Cys
        35                  40                  45

Cys Thr Gly Thr Cys Cys Gly Gly Cys Ala Gly Cys Cys Ala Gly Gly
    50                  55                  60

Gly Ala Ala Thr Cys Thr Thr Cys Cys Cys Thr Cys Thr Gly Gly Cys
65                  70                  75                  80

Cys Thr Thr Cys Thr Thr Cys Ala Thr Cys Thr Ala Cys Gly Thr Gly
                85                  90                  95
Cys Cys Cys Ala Thr Gly Ala Ala Cys Gly Ala Gly Cys Ala Gly Ala
            100                 105                 110

Thr Cys Gly Thr Gly Ala Thr Cys Gly Gly Cys Cys Gly Gly Cys Thr
        115                 120                 125

Gly Gly Ala Cys Gly Ala Gly Gly Ala Thr Ala Thr Thr Ala Thr Cys
    130                 135                 140
Cys Thr Gly Cys Cys Cys Thr Cys Cys Ala Gly Cys Thr Thr Cys Gly
145                 150                 155                 160
Ala Gly Cys Gly Gly Gly Gly Cys Thr Cys Cys Gly Ala Gly Gly Thr
                165                 170                 175

Cys Gly Thr Gly Ala Thr Cys Cys Ala Cys Thr Gly Gly Ala Ala Gly
            180                 185                 190

Thr Ala Cys Cys Ala Gly Gly Ala Cys Thr Cys Cys Thr Ala Cys Ala
        195                 200                 205

Ala Gly Gly Thr Gly Cys Ala Cys Thr Cys Cys Thr Ala Cys Thr Ala
    210                 215                 220

Cys Ala Ala Gly Gly Gly Cys Thr Cys Cys Gly Ala Cys Cys Ala Cys
225                 230                 235                 240

Cys Thr Gly Gly Ala Ala Thr Cys Cys Cys Ala Gly Gly Ala Cys Cys
                245                 250                 255

Cys Cys Ala Gly Ala Thr Ala Cys Gly Cys Cys Ala Ala Cys Cys Gly
            260                 265                 270

Gly Ala Cys Cys Ala Gly Cys Cys Thr Gly Thr Thr Cys Thr Ala Cys
        275                 280                 285

Ala Ala Cys Gly Ala Gly Ala Thr Cys Cys Ala Gly Ala Ala Cys Gly
    290                 295                 300

Gly Cys Ala Ala Cys Gly Cys Cys Thr Cys Cys Cys Thr Gly Thr Thr
305                 310                 315                 320

Cys Thr Thr Cys Cys Gly Gly Cys Gly Ala Gly Thr Gly Thr Cys Cys
                325                 330                 335

Cys Thr Gly Cys Thr Gly Gly Ala Thr Gly Ala Gly Gly Gly Cys Ala
            340                 345                 350

Thr Cys Thr Ala Cys Ala Cys Cys Thr Gly Thr Thr Ala Cys Gly Thr
        355                 360                 365

Gly Gly Gly Cys Ala Cys Cys Gly Cys Cys Ala Thr Cys Cys Ala Ala
    370                 375                 380

Gly Thr Gly Ala Thr Cys Ala Cys Cys Ala Ala Cys Ala Ala Gly Gly
385                 390                 395                 400

Thr Gly Gly Thr Gly Cys Thr Gly Ala Ala Ala Gly Thr Gly Gly Gly
                405                 410                 415

Cys Gly Thr Gly Thr Thr Cys Cys Thr Gly Ala Cys Cys Cys Cys Cys
            420                 425                 430

Gly Thr Gly Ala Thr Gly Ala Ala Gly Thr Ala Cys Gly Ala Gly Ala
        435                 440                 445
```

-continued

Ala Gly Cys Gly Gly Ala Ala Thr Ala Cys Cys Ala Ala Cys Thr Cys
450 455 460

Thr Thr Thr Cys Cys Thr Gly Ala Thr Cys Thr Gly Cys Thr Cys Cys
465 470 475 480

Gly Thr Gly Cys Thr Gly Thr Cys Cys Gly Thr Gly Thr Ala Cys Cys
485 490 495

Cys Thr Cys Gly Gly Cys Cys Cys Ala Thr Cys Ala Thr Cys Ala Cys
500 505 510

Cys Thr Gly Gly Ala Ala Gly Ala Thr Gly Gly Ala Cys Ala Ala Cys
515 520 525

Ala Cys Cys Cys Cys Cys Ala Thr Cys Thr Cys Cys Gly Ala Gly Ala
530 535 540

Ala Cys Ala Ala Cys Ala Thr Gly Gly Ala Ala Gly Ala Gly Ala Cys
545 550 555 560

Ala Gly Gly Cys Thr Cys Cys Cys Thr Gly Gly Ala Cys Thr Cys Cys
565 570 575

Thr Thr Cys Thr Cys Cys Ala Thr Cys Ala Ala Cys Thr Cys Cys Cys
580 585 590

Cys Cys Cys Thr Gly Ala Ala Cys Ala Thr Thr Ala Cys Cys Gly Gly
595 600 605

Cys Thr Cys Cys Ala Ala Cys Thr Cys Cys Thr Cys Cys Thr Ala Cys
610 615 620

Gly Ala Gly Thr Gly Cys Ala Cys Cys Ala Thr Cys Gly Ala Gly Ala
625 630 635 640

Ala Cys Thr Cys Cys Cys Thr Gly Cys Thr Gly Ala Ala Gly Cys Ala
645 650 655

Gly Ala Cys Cys Thr Gly Gly Ala Cys Cys Gly Gly Cys Ala Gly Ala
660 665 670

Thr Gly Gly Ala Cys Thr Ala Thr Gly Ala Ala Gly Gly Ala Cys Gly
675 680 685

Gly Cys Cys Thr Gly Cys Ala Cys Ala Ala Gly Ala Thr Gly Cys Ala
690 695 700

Gly Thr Cys Cys Gly Ala Gly Cys Ala Cys Gly Thr Gly Thr Cys Cys
705 710 715 720

Cys Thr Gly Thr Cys Cys Thr Gly Cys Cys Ala Gly Cys Cys Cys Gly
725 730 735

Thr Gly Ala Ala Cys Gly Ala Cys Thr Ala Cys Thr Thr Cys Ala Gly
740 745 750

Cys Cys Cys Cys Ala Ala Cys Cys Ala Gly Gly Ala Cys Thr Thr Cys
755 760 765

Ala Ala Ala Gly Thr Gly Ala Cys Cys Thr Gly Gly Thr Cys Cys Cys
770 775 780

Gly Gly Ala Thr Gly Ala Ala Gly Thr Cys Cys Gly Gly Cys Ala Cys
785 790 795 800

Cys Thr Thr Cys Ala Gly Cys Gly Thr Gly Cys Thr Gly Gly Cys Cys
805 810 815

Thr Ala Cys Thr Ala Cys Cys Thr Gly Thr Cys Cys Ala Gly Cys Thr
820 825 830

Cys Cys Cys Ala Gly Ala Ala Cys Ala Cys Cys Ala Thr Cys Ala Thr
835 840 845

Cys Ala Ala Cys Gly Ala Gly Thr Cys Cys Cys Gly Gly Thr Thr Cys
850 855 860

Thr Cys Cys Thr Gly Gly Ala Ala Cys Ala Ala Ala Gly Ala Gly Cys

-continued

```
                865                 870                 875                 880
        Thr Gly Ala Thr Cys Ala Ala Cys Cys Ala Gly Thr Cys Cys Gly Ala
                            885                 890                 895
        Cys Thr Thr Cys Thr Cys Cys Ala Thr Gly Ala Ala Cys Cys Thr Gly
                                900                 905                 910
        Ala Thr Gly Gly Ala Cys Cys Thr Gly Ala Ala Cys Cys Thr Gly Thr
                                915                 920                 925
        Cys Cys Gly Ala Cys Ala Gly Cys Gly Gly Cys Gly Ala Gly Thr Ala
                                930                 935                 940
        Cys Cys Thr Gly Thr Gly Cys Ala Ala Cys Ala Thr Cys Thr Cys Cys
        945                 950                 955                 960
        Ala Gly Cys Gly Ala Cys Gly Ala Gly Thr Ala Cys Ala Cys Cys Cys
                                965                 970                 975
        Thr Gly Cys Thr Gly Ala Cys Cys Ala Thr Cys Thr Cys Ala Cys Ala Cys
                            980                 985                 990
        Cys Gly Thr Gly Cys Ala Cys Gly  Thr Gly Gly Ala Ala  Cys Cys Cys
                            995                 1000                1005
        Thr Cys  Cys Cys Ala Gly Gly  Ala Ala Ala Cys Cys  Gly Ala Gly
            1010                1015                1020
        Thr Cys  Thr Ala Ala Gly Thr  Ala Cys Gly Gly Cys  Cys Cys Thr
            1025                1030                1035
        Cys Cys  Cys Thr Gly Cys Cys  Cys Ala Cys Cys Thr  Thr Gly Thr
            1040                1045                1050
        Cys Cys  Cys Gly Cys Cys Cys  Cys Thr Gly Ala Ala  Thr Thr Thr
            1055                1060                1065
        Cys Thr  Gly Gly Gly Cys Gly  Gly Ala Cys Cys Cys  Thr Cys Thr
            1070                1075                1080
        Gly Thr  Gly Thr Thr Cys Cys  Thr Gly Thr Thr Cys  Cys Cys Cys
            1085                1090                1095
        Cys Cys  Ala Ala Ala Gly Cys  Cys Cys Ala Ala Gly  Gly Ala Cys
            1100                1105                1110
        Ala Cys  Cys Cys Thr Gly Ala  Thr Gly Ala Thr Cys  Thr Cys Cys
            1115                1120                1125
        Cys Gly  Gly Ala Cys Cys Cys  Cys Cys Gly Ala Ala  Gly Thr Gly
            1130                1135                1140
        Ala Cys  Ala Thr Gly Cys Gly  Thr Gly Gly Thr Gly  Gly Thr Gly
            1145                1150                1155
        Gly Ala  Thr Gly Thr Gly Thr  Cys Cys Cys Ala Gly  Gly Ala Ala
            1160                1165                1170
        Gly Ala  Thr Cys Cys Cys Gly  Ala Gly Gly Thr Gly  Cys Ala Gly
            1175                1180                1185
        Thr Thr  Cys Ala Ala Thr Thr  Gly Gly Thr Ala Cys  Gly Thr Gly
            1190                1195                1200
        Gly Ala  Cys Gly Gly Cys Gly  Thr Gly Gly Ala Ala  Gly Thr Gly
            1205                1210                1215
        Cys Ala  Cys Ala Ala Cys Gly  Cys Cys Ala Ala Gly  Ala Cys Cys
            1220                1225                1230
        Ala Ala  Gly Cys Cys Cys Ala  Gly Ala Gly Ala Gly  Gly Ala Ala
            1235                1240                1245
        Cys Ala  Gly Thr Thr Cys Ala  Ala Cys Thr Cys Cys  Ala Cys Cys
            1250                1255                1260
        Thr Ala  Cys Cys Gly Gly Gly  Thr Gly Gly Thr Gly  Thr Cys Thr
            1265                1270                1275
```

```
Gly Thr Gly Cys Thr Gly Ala Cys Cys Gly Thr Gly Cys Thr Gly
            1280                1285                1290

Cys Ala Cys Cys Ala Gly Gly Ala Cys Thr Gly Gly Cys Thr Gly
            1295                1300                1305

Ala Ala Cys Gly Gly Cys Ala Ala Ala Gly Ala Gly Thr Ala Cys
            1310                1315                1320

Ala Ala Gly Thr Gly Cys Ala Ala Gly Gly Thr Gly Thr Cys Cys
            1325                1330                1335

Ala Ala Cys Ala Ala Gly Gly Gly Cys Cys Thr Gly Cys Cys Cys
            1340                1345                1350

Ala Gly Cys Thr Cys Cys Ala Thr Cys Gly Ala Ala Ala Ala Gly
            1355                1360                1365

Ala Cys Cys Ala Thr Cys Thr Cys Cys Ala Ala Gly Gly Cys Cys
            1370                1375                1380

Ala Ala Gly Gly Gly Cys Cys Ala Gly Cys Cys Cys Cys Gly Gly
            1385                1390                1395

Gly Ala Ala Cys Cys Cys Ala Gly Gly Thr Gly Thr Ala Cys
            1400                1405                1410

Ala Cys Ala Cys Thr Gly Cys Cys Thr Cys Cys Ala Ala Gly Cys
            1415                1420                1425

Cys Ala Gly Gly Ala Ala Gly Ala Gly Ala Thr Gly Ala Cys Cys
            1430                1435                1440

Ala Ala Gly Ala Ala Cys Cys Ala Gly Gly Thr Gly Thr Cys Cys
            1445                1450                1455

Cys Thr Gly Ala Cys Thr Thr Gly Cys Cys Thr Cys Gly Thr Gly
            1460                1465                1470

Ala Ala Gly Gly Gly Cys Thr Thr Cys Thr Ala Cys Cys Cys Cys
            1475                1480                1485

Thr Cys Cys Gly Ala Thr Ala Thr Cys Gly Cys Cys Gly Thr Gly
            1490                1495                1500

Gly Ala Ala Thr Gly Gly Gly Ala Gly Thr Cys Cys Ala Ala Cys
            1505                1510                1515

Gly Gly Cys Cys Ala Gly Cys Cys Thr Gly Ala Gly Ala Ala Cys
            1520                1525                1530

Ala Ala Cys Thr Ala Cys Ala Ala Gly Ala Cys Cys Ala Cys Cys
            1535                1540                1545

Cys Cys Cys Cys Cys Thr Gly Thr Gly Cys Thr Gly Gly Ala Cys
            1550                1555                1560

Thr Cys Cys Gly Ala Cys Gly Gly Cys Thr Cys Thr Thr Thr Cys
            1565                1570                1575

Thr Thr Cys Cys Thr Gly Thr Ala Cys Thr Cys Cys Cys Gly Cys
            1580                1585                1590

Cys Thr Gly Ala Cys Cys Gly Thr Gly Gly Ala Cys Ala Ala Gly
            1595                1600                1605

Thr Cys Cys Ala Gly Ala Thr Gly Gly Cys Ala Gly Gly Ala Ala
            1610                1615                1620

Gly Gly Cys Ala Ala Cys Gly Thr Gly Thr Thr Cys Thr Cys Cys
            1625                1630                1635

Thr Gly Cys Ala Gly Cys Gly Thr Gly Ala Thr Gly Cys Ala Cys
            1640                1645                1650

Gly Ala Gly Gly Cys Cys Cys Thr Gly Cys Ala Cys Ala Ala Cys
            1655                1660                1665
```

Cys Ala Cys Thr Ala Cys Ala Cys Cys Cys Ala Gly Ala Ala Gly
        1670                1675                1680

Thr Cys Cys Cys Thr Gly Ala Gly Cys Cys Thr Gly Thr Cys Cys
    1685                1690                1695

Cys Cys Cys Gly Gly Cys Thr Gly Ala
    1700                1705

<210> SEQ ID NO 26
<211> LENGTH: 318
<212> TYPE: PRT
<213> ORGANISM: Artificial Sequence
<220> FEATURE:
<223> OTHER INFORMATION: Artificial Polypeptide - extracellular domain

<400> SEQUENCE: 26

Ile Phe Pro Leu Ala Phe Phe Ile Tyr Val Pro Met Asn Glu Gln Ile
1               5                   10                  15

Val Ile Gly Arg Leu Asp Glu Asp Ile Ile Leu Pro Ser Ser Phe Glu
            20                  25                  30

Arg Gly Ser Glu Val Val Ile His Trp Lys Tyr Gln Asp Ser Tyr Lys
        35                  40                  45

Val His Ser Tyr Tyr Lys Gly Ser Asp His Leu Glu Ser Gln Asp Pro
    50                  55                  60

Arg Tyr Ala Asn Arg Thr Ser Leu Phe Tyr Asn Glu Ile Gln Asn Gly
65                  70                  75                  80

Asn Ala Ser Leu Phe Phe Arg Arg Val Ser Leu Leu Asp Glu Gly Ile
                85                  90                  95

Tyr Thr Cys Tyr Val Gly Thr Ala Ile Gln Val Ile Thr Asn Lys Val
            100                 105                 110

Val Leu Lys Val Gly Val Phe Leu Thr Pro Val Met Lys Tyr Glu Lys
        115                 120                 125

Arg Asn Thr Asn Ser Phe Leu Ile Cys Ser Val Leu Ser Val Tyr Pro
    130                 135                 140

Arg Pro Ile Ile Thr Trp Lys Met Asp Asn Thr Pro Ile Ser Glu Asn
145                 150                 155                 160

Asn Met Glu Glu Thr Gly Ser Leu Asp Ser Phe Ser Ile Asn Ser Pro
                165                 170                 175

Leu Asn Ile Thr Gly Ser Asn Ser Ser Tyr Glu Cys Thr Ile Glu Asn
            180                 185                 190

Ser Leu Leu Lys Gln Thr Trp Thr Gly Arg Trp Thr Met Lys Asp Gly
        195                 200                 205

Leu His Lys Met Gln Ser Glu His Val Ser Leu Ser Cys Gln Pro Val
    210                 215                 220

Asn Asp Tyr Phe Ser Pro Asn Gln Asp Phe Lys Val Thr Trp Ser Arg
225                 230                 235                 240

Met Lys Ser Gly Thr Phe Ser Val Leu Ala Tyr Tyr Leu Ser Ser Ser
                245                 250                 255

Gln Asn Thr Ile Ile Asn Glu Ser Arg Phe Ser Trp Asn Lys Glu Leu
            260                 265                 270

Ile Asn Gln Ser Asp Phe Ser Met Asn Leu Met Asp Leu Asn Leu Ser
        275                 280                 285

Asp Ser Gly Glu Tyr Leu Cys Asn Ile Ser Ser Asp Glu Tyr Thr Leu
    290                 295                 300

Leu Thr Ile His Thr Val His Val Glu Pro Ser Gln Glu Thr
305                 310                 315

<210> SEQ ID NO 27
<211> LENGTH: 233
<212> TYPE: PRT
<213> ORGANISM: Artificial Sequence
<220> FEATURE:
<223> OTHER INFORMATION: Synthetic Polypeptide - murine IgG2a domain

<400> SEQUENCE: 27

```
Glu Pro Arg Gly Pro Thr Ile Lys Pro Cys Pro Pro Cys Lys Cys Pro
1               5                   10                  15

Ala Pro Asn Leu Leu Gly Gly Pro Ser Val Phe Ile Phe Pro Pro Lys
            20                  25                  30

Ile Lys Asp Val Leu Met Ile Ser Leu Ser Pro Ile Val Thr Cys Val
        35                  40                  45

Val Val Asp Val Ser Glu Asp Asp Pro Asp Val Gln Ile Ser Trp Phe
    50                  55                  60

Val Asn Asn Val Glu Val His Thr Ala Gln Thr Gln Thr His Arg Glu
65                  70                  75                  80

Asp Tyr Asn Ser Thr Leu Arg Val Val Ser Ala Leu Pro Ile Gln His
                85                  90                  95

Gln Asp Trp Met Ser Gly Lys Glu Phe Lys Cys Lys Val Asn Asn Lys
            100                 105                 110

Asp Leu Pro Ala Pro Ile Glu Arg Thr Ile Ser Lys Pro Lys Gly Ser
        115                 120                 125

Val Arg Ala Pro Gln Val Tyr Val Leu Pro Pro Pro Glu Glu Glu Met
    130                 135                 140

Thr Lys Lys Gln Val Thr Leu Thr Cys Met Val Thr Asp Phe Met Pro
145                 150                 155                 160

Glu Asp Ile Tyr Val Glu Trp Thr Asn Asn Gly Lys Thr Glu Leu Asn
                165                 170                 175

Tyr Lys Asn Thr Glu Pro Val Leu Asp Ser Asp Gly Ser Tyr Phe Met
            180                 185                 190

Tyr Ser Lys Leu Arg Val Glu Lys Lys Asn Trp Val Glu Arg Asn Ser
        195                 200                 205

Tyr Ser Cys Ser Val Val His Glu Gly Leu His Asn His His Thr Thr
    210                 215                 220

Lys Ser Phe Ser Arg Thr Pro Gly Lys
225                 230
```

<210> SEQ ID NO 28
<211> LENGTH: 337
<212> TYPE: DNA
<213> ORGANISM: Artificial Sequence
<220> FEATURE:
<223> OTHER INFORMATION: Synthetic Polynucleotide - Polynucleotide
        Encoding Light Chain Variable Region Anti-Human B7-H5 Clone 18C3

<400> SEQUENCE: 28

```
gacattgtga tgtcacagtc tccatcctcc ctggctgtgt cagcaggaga gaaggtcact    60
atgagctgca aatccagtca gagtctgctc aacagtagaa cccgaaagaa ccagttggct   120
tggtaccagc agaaaccagg gcagtctcct aaactgctga tctactgggc atccactagg   180
gaatctgggg tccctgatcg cttcacaggc agtggatctg gacagattt cactctcacc    240 atcagcagtg tgcaggctga agacctggca gtttattact gcaagcaatc ttataatctt   300
cggacgttcg gtggaggcac caagctggaa atcaaac                            337
```

```
<210> SEQ ID NO 29
<211> LENGTH: 22
<212> TYPE: PRT
<213> ORGANISM: Artificial Sequence
<220> FEATURE:
<223> OTHER INFORMATION: Synthetic Polypeptide - signal sequence

<400> SEQUENCE: 29

Met Lys Ala Gln Thr Ala Leu Ser Phe Phe Leu Ile Leu Ile Thr Ser
1               5                   10                  15

Leu Ser Gly Ser Gln Gly
            20
```